US012685863B2

(12) United States Patent
Yeniel et al.

(10) Patent No.: US 12,685,863 B2
(45) Date of Patent: Jul. 21, 2026

(54) SYSTEMS AND METHODS FOR TRANSCUTANEOUS POSTERIOR TIBIAL NERVE STIMULATION

(71) Applicant: Soranus Arge Ve Danismanlik Hizmetleri Sanayi Ticaret Anonim Sirketi, Izmir (TR)

(72) Inventors: Ahmet Ozgur Yeniel, Izmir (TR); Ahmet Mete Ergenoglu, Izmir (TR); Serdal Temel, Izmir (TR); Ilker Basaran, Izmir (TR); Gokhan Bulunur, Izmir (TR); Ozgun Selim Germiyan, Izmir (TR); Engin Kocak, Izmir (TR)

(73) Assignee: Soranus Arge Ve Danismanlik Hizmetleri Sanayi Ticaret Anonim Sirketi, Izmir (TR)

( * ) Notice: Subject to any disclaimer, the term of this patent is extended or adjusted under 35 U.S.C. 154(b) by 313 days.

(21) Appl. No.: 18/371,924

(22) Filed: Sep. 22, 2023

(65) Prior Publication Data

US 2024/0157142 A1 May 16, 2024

Related U.S. Application Data

(63) Continuation of application No. PCT/TR2022/050268, filed on Mar. 24, 2022.

(30) Foreign Application Priority Data

Mar. 24, 2021 (TR) ................................ 2021/005358
Sep. 14, 2021 (TR) ................................ 2021/014395

(51) Int. Cl.
A61N 1/36 (2006.01)
A61N 1/04 (2006.01)
G16H 40/67 (2018.01)

(52) U.S. Cl.
CPC ....... *A61N 1/36034* (2017.08); *A61N 1/0456* (2013.01); *A61N 1/0492* (2013.01); *A61N 1/36031* (2017.08); *G16H 40/67* (2018.01)

(58) Field of Classification Search
None
See application file for complete search history.

(56) References Cited

U.S. PATENT DOCUMENTS 10,765,856 B2 * 9/2020 Wong ................. A61N 1/36067

FOREIGN PATENT DOCUMENTS

WO 2019143790 A1 7/2019
WO 2020006048 A1 1/2020
(Continued)

OTHER PUBLICATIONS

International Search Report; PCT/TR2022/050268; Date: Aug. 8, 2022; By: Authorized Officer: Scheffler, Arnaud.

*Primary Examiner* — Carl H Layno
*Assistant Examiner* — Bryan McAllister Lee
(74) *Attorney, Agent, or Firm* — Greenberg Traurig LLP; Roman Fayerberg; Jaime Burke

(57) ABSTRACT

A system for nerve stimulation can include a neuromodulation device configured to be worn by a patient, the neuromodulation device configured for transcutaneous delivery of electrical stimulation to the tibial nerve; a mobile application executing on a mobile device in communication with the neuromodulation device, the mobile application configured to monitor the transcutaneous delivery of the electrical stimulation by the neuromodulation device and cause the mobile device to display information about the transcutaneous delivery of the electrical stimulation to the tibial nerve; and a web service in communication with the mobile application, the web service configured to transmit, to the mobile application, a treatment protocol and notifications defining (Continued)

Neuromodulation Device 1

4A

Mobile Application 2

4B

Web Service 3 the transcutaneous delivery of the electrical stimulation to the tibial nerve and receive, from the mobile application, the information about the transcutaneous delivery of the electrical stimulation to the tibial nerve.

22 Claims, 61 Drawing Sheets

(56) References Cited

FOREIGN PATENT DOCUMENTS

| WO | 2020086726 | A2 | 4/2020 |
|----|------------|-----|--------|
| WO | 2020185601 | A1 | 9/2020 |
| WO | 2022203640 | A1 | 9/2022 |

* cited by examiner

Web Service
3

4B

Mobile
Application 2

4A

Neuromodulation
Device
1 frequency = (1/T) [Hz] ( from 1 HZ to 50 Hz )

Current [mA]

T [us]

w [us]

0 - 60 mA

Time [us]

A. REPRESENTATION OF IMPEDANCE DUE TO CONNECTIONS

B. CURRENT PULSE MEASUREMENT BETWEEN 59 AND 60

Patient turns on the neuromodulation device by provided button 161

Light indicator flashes and buzzer blips while neuromodulation device turns on 162

When patient opens the mobile app, "treatment take" screen welcomes the patients 163

Once the patient presses the "Start" button, mobile application tries to connect web service to take the treatment protocol assigned by health professional 164

Patient adheres the device according to instructions provided on the mobile application and/or help of Virtual Reality Camera interface that illustrates the device on the patient's leg 160

Patient puts batteries into device and adheres the hydrogels on both electrodes of device 159

Mobile application notifies patient of the treatment session dates 158

Results are communicated to healthcare professional and stored on web service 157

Diagnosis of Syndrome 151

Patient purchases the neuro modulation device 152

Healthcare provider registers patient identifier and device identifier from the web interface via web service 153

Healthcare provider assigns treatment protocol to the patient 154

Patient logs into mobile application and mobile application redirects patient to assessment screen 155

Patient fills in validated assessment tools on mobile application to assess severity of disease 156

3000

1

SYSTEMS AND METHODS FOR TRANSCUTANEOUS POSTERIOR TIBIAL NERVE STIMULATION

RELATED APPLICATIONS

This application is a continuation of International PCT Application No. PCT/TR2022/050268, filed Mar. 24, 2022, and claims the benefit of and priority to Turkish Patent Application No. 2021/005358, filed on Mar. 24, 2021, and priority to Turkish Patent Application No. 2021/014395, filed on Sep. 14, 2021, the entirety of this applications are hereby incorporated herein by reference.

FIELD

This disclosure relates to a transcutaneous posterior tibial nerve stimulation systems and data driven methods that can be remotely monitored and that can monitor the course of treatment in the treatment of urinary incontinence, fecal incontinence, pelvic pain, or sexual dysfunction.

BACKGROUND

Posterior tibial neuromodulation (PTNS) can help treat pelvic floor disorders (e.g., overactive bladder, urinary incontinence, fecal incontinence, chronic pelvic pain, or sexual dysfunction). However, it is difficult to keep the patient compliant with a treatment plan.

SUMMARY

In some aspects, the techniques described herein relate to a system for nerve stimulation, the system including: a neuromodulation device configured to be worn and adhered to a patient in proximity to a tibial nerve of the patient, the neuromodulation device configured for transcutaneous delivery of electrical stimulation to the tibial nerve; a mobile application executing on a mobile device in communication with the neuromodulation device, the mobile application configured to monitor the transcutaneous delivery of the electrical stimulation by the neuromodulation device and cause the mobile device to display information about the transcutaneous delivery of the electrical stimulation to the tibial nerve; and a web service in communication with the mobile application, the web service configured to transmit, to the mobile application, a treatment protocol and notifications defining the transcutaneous delivery of the electrical stimulation to the tibial nerve and receive, from the mobile application, the information about the transcutaneous delivery of the electrical stimulation to the tibial nerve.

In some aspects, the techniques described herein relate to a system, further including a plurality of positioning devices positioned in a treatment area and a tracker device worn by the patient, the web service configured to communicate with the plurality of positioning devices and the tracker device to identify a location of the tracker device for the web service to modify the treatment protocol based on the location of the tracker device.

In some aspects, the techniques described herein relate to a system, wherein the mobile application is further configured to: identify, based on communications received from the tracker device or the plurality of positioning devices positioned in the treatment area, the location of the mobile device; generate, based on the location of the mobile device or the tracker device, a prompt for input of treatment activities; detect selected treatment activities associated with the treatment protocol responsive to the prompt; and transmit the location and the selected treatment activities to the web service.

In some aspects, the techniques described herein relate to a system, wherein the neuromodulation device further includes at least one light-emitting diode (LED) configured to emit light responsive to the transcutaneous delivery of the electrical stimulation to the tibial nerve.

In some aspects, the techniques described herein relate to a system, wherein the neuromodulation device further includes an buzzer configured to generate audio signals responsive to the transcutaneous delivery of the electrical stimulation to the tibial nerve.

In some aspects, the techniques described herein relate to a system, wherein the neuromodulation device further includes a voltage controller configured to modulate supply voltage for the transcutaneous delivery of the electrical stimulation to the tibial nerve.

In some aspects, the techniques described herein relate to a system, wherein the neuromodulation device further including: a first electrode and a second electrode configured for the transcutaneous delivery of the electrical stimulation to the tibial nerve; and a strap configured to couple to strap connectors extending from the neuromodulation device to secure the neuromodulation device to the patient. 8.

In some aspects, the techniques described herein relate to a system, wherein the neuromodulation device is further configured to: store, responsive to termination of communications with the mobile device executing the mobile application, treatment activities to a memory of the neuromodulation device; and transmit, to the mobile device, the treatment activities upon re-establishing communications with the mobile device.

In some aspects, the techniques described herein relate to a system, wherein the mobile application is further configured to: receive an assigned device identifier of the neuromodulation device of the patient responsive to validating a patient identifier of the patient; receive a candidate device identifier of the neuromodulation device attempting to establish communications with the mobile application; and establish the communications with the neuromodulation device responsive to matching the assigned device identifier of the neuromodulation device to the candidate device identifier of the neuromodulation device.

In some aspects, the techniques described herein relate to a system, wherein the neuromodulation device further includes an accelerometer configured to measure mobility and activity of the patient.

In some aspects, the techniques described herein relate to a system, wherein the neuromodulation device further includes memory configured to store treatment activities about the transcutaneous delivery of the electrical stimulation to the tibial nerve.

In some aspects, the techniques described herein relate to a system, further including a sensor device configured to be worn by the patient, the sensor device further configured to: generate sensor measurements including oxygen concentration, pulse, electrical frequency, electrical voltage, and accelerometer movements; and transmit the sensor measurements to the mobile application or to the neuromodulation device.

In some aspects, the techniques described herein relate to a system, wherein the mobile application is further configured to: receive the sensor measurements from the sensor device; and generate a comparison between the sensor measurements and threshold measurements to verify proper placement of the neuromodulation device.

In some aspects, the techniques described herein relate to a system any one, wherein the mobile application is further configured to: generate an interface including a patient image of an extremity of the patient to which to apply the neuromodulation device; identify, in the patient image, a treatment site on the extremity to which to apply the neuromodulation device; and generate a virtual image of the neuromodulation device overlayed on the treatment site in the patient image of the extremity for display in the interface to indicate where to position the neuromodulation device.

In some aspects, the techniques described herein relate to a system, wherein the mobile application is further configured to: communicate with a virtual reality headset; and cause the virtual reality headset to display the interface.

In some aspects, the techniques described herein relate to a system, wherein the mobile application is further configured to: receive, from the virtual reality headset, modifications to the treatment protocol.

In some aspects, the techniques described herein relate to a system, wherein the neuromodulation device further includes feedback electrodes configured to generate electrical measurements for identifying a nerve threshold at which the patient reacts to neuromodulation; and wherein the neuromodulation device is further configured to transmit the electrical measurements to the mobile application.

In some aspects, the techniques described herein relate to a system, wherein the mobile application is further configured to adjust a treatment current based on the electrical measurements received from the feedback electrodes of the neuromodulation device.

In some aspects, the techniques described herein relate to a system, wherein the mobile application is further configured to modify the treatment protocol based on the electrical measurements received from the feedback electrodes of the neuromodulation device.

In some aspects, the techniques described herein relate to a method for a patient to apply neuromodulation with a neuromodulation device worn by the patient, the method including: establishing, by one or more processors, communications with a mobile device executing a mobile application for managing a treatment protocol applied by the neuromodulation device to the patient; and receiving, by the one or more processors, a treatment protocol to apply to the patient; causing, by the one or more processors, responsive to receiving a signal from the mobile application to begin applying the treatment protocol, the neuromodulation device to begin transcutaneous delivery to apply the neuromodulation to a tibial nerve of the patient.

In some aspects, the techniques described herein relate to a method, the method further including: selecting, by the one or more processors, a supply voltage and a treatment current for the neuromodulation device, the treatment current identified in the communications from the mobile device.

In some aspects, the techniques described herein relate to a method, the method further including: detecting, by the one or more processors, a treatment voltage applied by the neuromodulation device to the patient to apply the treatment protocol, the treatment voltage based on the supply voltage and the treatment current; increasing, by the one or more processors, the supply voltage responsive to a difference between the supply voltage and the treatment voltage satisfying a first threshold; or decreasing, by the one or more processors, the supply voltage responsive to the difference between the supply voltage and the treatment voltage satisfying a second threshold.

In some aspects, the techniques described herein relate to a method, the method further including: transmitting, by the one or more processors, to the mobile application, an identification of the treatment current and an identifier of the neuromodulation device; receiving, by the one or more processors, from the mobile application, an adjusted treatment current; and causing, by the one or more processors, a current source of the neuromodulation device to generate the adjusted treatment current. 25.

In some aspects, the techniques described herein relate to a method, the method further including: receiving, by the one or more processors, from feedback electrodes of the neuromodulation device, electrical measurements for identifying a nerve threshold at which the patient reacts to neuromodulation; and transmitting, by the one or more processors, the electrical measurements to the mobile application.

In some aspects, the techniques described herein relate to a method for managing neuromodulation on a mobile application to improve adherence to treatment, the method including: receiving, by one or more processors, from a web service, a treatment protocol to be applied by a neuromodulation device to a tibial nerve of a patient; detecting, by the one or more processors, a selection to increase a treatment current for applying the treatment protocol; and transmitting, by the one or more processors, treatment parameters included in the treatment protocol and the treatment current to the neuromodulation device.

In some aspects, the techniques described herein relate to a method, wherein the selection is a first selection and further including: detecting, by the one or more processors, a second selection to decrease the treatment current.

In some aspects, the techniques described herein relate to a method, wherein the selection is a first selection and further including: detecting, by the one or more processors, a second selection for the neuromodulation device to begin transcutaneous delivery to apply the neuromodulation to the tibial nerve; and transmitting, by the one or more processors, a signal to the neuromodulation device to begin the transcutaneous delivery to apply the neuromodulation to the tibial nerve.

In some aspects, the techniques described herein relate to a method, the method further including: identifying, by the one or more processors, the treatment current being applied by the neuromodulation device.

In some aspects, the techniques described herein relate to a method, wherein the selection is a first selection and the method further including: generating, by the one or more processors, a first interface to adjust the treatment current to be applied by the neuromodulation device to the patient; detecting, by the one or more processors, a second selection of an adjusted treatment current; transmitting, by the one or more processors, the adjusted treatment current to the neuromodulation device; and generating, by the one or more processors, a second interface to display the adjusted treatment current to the patient.

In some aspects, the techniques described herein relate to a method, wherein the mobile application is further configured to adjust the treatment current based on electrical measurements received from feedback electrodes of the neuromodulation device.

In some aspects, the techniques described herein relate to a method, wherein the mobile application is further configured to modify the treatment protocol based on electrical measurements received from feedback electrodes of the neuromodulation device.

In some aspects, the techniques described herein relate to a method, the method further including: generating, by the one or more processors, a prompt for input of treatment activities; detecting, by the one or more processors, selections of the treatment activities to refine the treatment protocol; transmitting, by the one or more processors, to the web service, the treatment activities; and receiving, by the one or more processors, from the web service, modifications to the treatment protocol based on the treatment activities.

In some aspects, the techniques described herein relate to a method, the method further including: generating, by the one or more processors, a prompt for input of treatment activities; detecting, by the one or more processors, selections of the treatment activities to refine the treatment protocol; identifying, by the one or more processors, based on communications received from a plurality of positioning devices positioned in a treatment area and a tracker device worn by the patient, a location of the patient; transmitting, by the one or more processors, to the web service, the location and the treatment activities; and receiving, by the one or more processors, from the web service, modifications to the treatment protocol based on the location and the treatment activities.

In some aspects, the techniques described herein relate to a method, the method further including: identifying, by the one or more processors, a patient identifier of the patient from a detected input of authentication information; receiving, by the one or more processors, an assigned device identifier of the neuromodulation device assigned to the patient identifier; receiving, by the one or more processors, a candidate device identifier from the neuromodulation device for applying the treatment protocol to the patient; and establishing, by the one or more processors, communications with the neuromodulation device responsive to verifying a match between the candidate device identifier and the assigned device identifier.

In some aspects, the techniques described herein relate to a method, the method further including: identifying, by the one or more processors, termination of communications with the neuromodulation device; and receiving, by the one or more processors, the treatment protocol upon re-establishing communications with the neuromodulation device.

In some aspects, the techniques described herein relate to a method, the method further including: generating, by the one or more processors, an interface including a patient image of an extremity of the patient to which to apply the neuromodulation device; identifying, by the one or more processors, in the patient image, a treatment site on the extremity to which to apply the neuromodulation device; and generating, by the one or more processors, a virtual image of the neuromodulation device overlayed on the treatment site in the patient image of the extremity for display in the interface to indicate where to position the neuromodulation device.

In some aspects, the techniques described herein relate to a method, the method further including: communicating, by the one or more processors, with a virtual reality headset; and causing, by the one or more processors, the virtual reality headset to display the interface.

In some aspects, the techniques described herein relate to a method, the method further including: receiving, by the one or more processors, from the virtual reality headset, modifications to the treatment protocol.

In some aspects, the techniques described herein relate to a method for administering neuromodulation by a web service, the method including: generating, by one or more processors, a selectable menu for a healthcare provider to configure treatment parameters defining a treatment protocol to be applied to a patient by a neuromodulation device; and transmitting, by the one or more processors, the selectable menu to a web application for display to the healthcare provider receiving, by the one or more processors, the treatment parameters from the web application; and transmitting, by the one or more processors, the treatment parameters to a mobile device executing a mobile application associated with the neuromodulation device, the mobile application causing the neuromodulation device to apply the treatment protocol.

In some aspects, the techniques described herein relate to a method, wherein transmitting the treatment parameters includes: receiving, by the one or more processors, an assigned device identifier of the neuromodulation device assigned to a patient identifier; and transmitting, by the one or more processors, the treatment parameters and the assigned device identifier to the mobile device executing the mobile application associated with the patient identifier, the mobile application causing the neuromodulation device to apply the treatment protocol responsive to the mobile application matching the assigned device identifier to a candidate device identifier received from the neuromodulation device.

In some aspects, the techniques described herein relate to a method, the method further including: receiving, by the one or more processors, treatment activities from the mobile application, the treatment activities including a treatment current being applied by the neuromodulation device, a timestamp of when the treatment current was applied, and a location of the mobile device or a tracker device; generating, by the one or more processors, a modified treatment protocol based on the treatment activities; and transmitting, by the one or more processors, the modified treatment protocol to the mobile application.

In some aspects, the techniques described herein relate to a method, the method further including: generating, by the one or more processors, a report for display by the web application to the healthcare provider, the report including the treatment activities.

In some aspects, the techniques described herein relate to a method, wherein generating the modified treatment protocol based on the treatment activities: establishing, by the one or more processors, communications with a plurality of positioning devices positioned in a treatment area and the tracker device worn by the patient; identifying, by the one or more processors, based on the communications, the location of the mobile device or the tracker device for the web service to modify the treatment protocol based on the location; and generating, by the one or more processors, the modified treatment protocol based on the location and the treatment activities.

In some aspects, the techniques described herein relate to a method, the method further including: generating, by the one or more processors, a notification to remind the patient about the modified treatment protocol; and transmitting, by the one or more processors, the notification to the mobile application for display to the patient.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 16-25 depict interfaces displayed by the web application for treatment management and monitoring.

Figure 1:
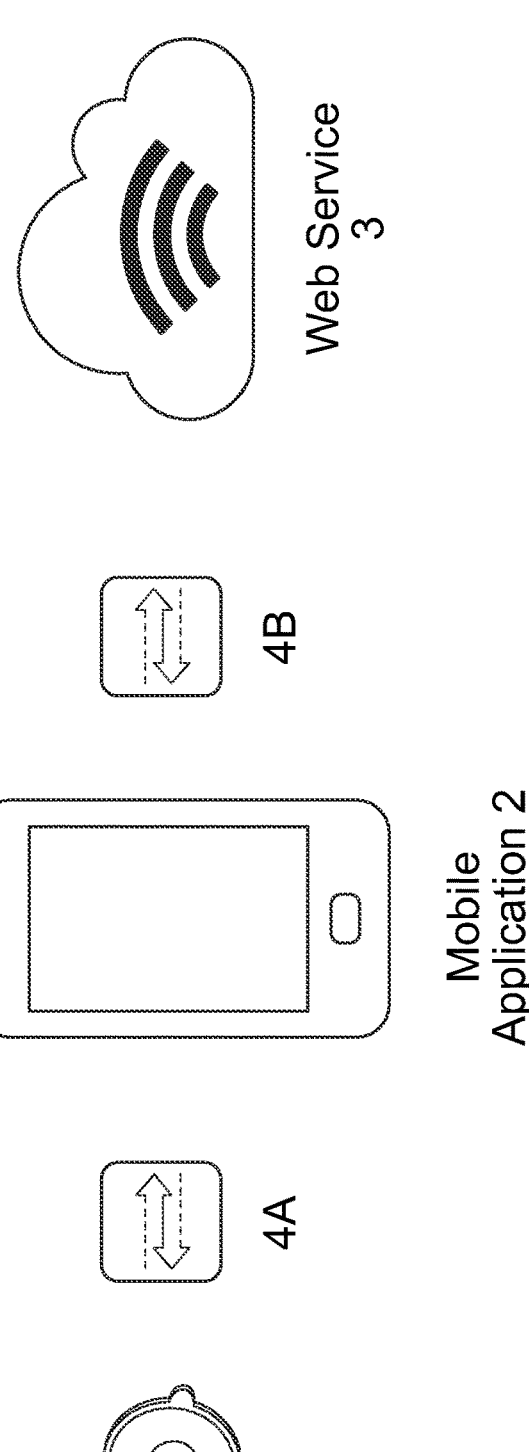
FIG. 1 depicts the neuromodulation device, the web service, and the mobile application.
Figure 1:
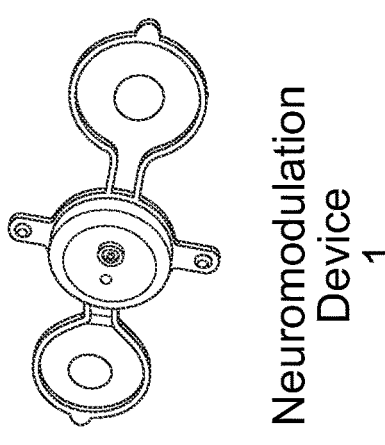

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The systems and methods described herein relate to a transcutaneous posterior tibial nerve neuromodulation device that can be remotely monitored and that can monitor the course of treatment in the treatment of urinary incontinence, fecal incontinence, sexual dysfunction pelvic pain. The present disclosure enables non-invasive treatment from anywhere with a mobile application. Mobile application-supported feedback, reward mechanisms, and audio-visual feedback on the neuromodulation device enable the patient to be aware of their condition for involvement with the treatment to improve compliance. Based on each treatment protocol, the quantitative recording of treatment efficacy (with urinary diary and validated questionnaires) from the web service enables for the generation of recommended treatment protocols. The mobile application interfaces with indoor positioning devices to provide notifications based on the location and time spent by the patient in places such as a kitchen, toilet, bathroom to increase the effective use of the urinary diary.

Transcutaneous posterior tibial neuromodulation (PTNS) treatment can be an effective, safe, and non-invasive treatment for an overactive bladder. PTNS can be applied with a needle, or it can also be applied non-invasively through the skin by the healthcare personnel in the hospital via electrodes. Treatments can include creating a neuromodulation effect with intermittent and multiple sessions on the sacral roots that enable the bladder innervation via the tibial nerve. The sacral nerve roots are in a main central position in bladder, bowel and genital organ innervations. For example, a treatment scheme of between 10 and 15 (for example, 12) sessions can be applied with the aim of delivering stimulation to the sacral roots via the posterior tibial nerve as a peripheral nerve tract. The weekly sessions are the commonly prescribed treatment schemes, but another regimen can also be prescribed.

In the PTNS treatment, the application can be made after the nerve stimulation (for example, by electrical stimulation) has been shown to be delivered to the right point. This may require a test period that involves obtaining a motor or sensory response when the stimulation is delivered. The test period may be desired since the intensity of the stimulation reaching the nerve may change in each session. The test period is tracked by the healthcare personnel asking the patient about their motor or sensory response, and the session can be started after accessing the nerve.

A healthcare personnel in a hospital can perform a 30-minute treatment with a re-determined intensity for each session from an explicitly described location for reaching the tibial nerve with a fine needle. The sessions can be started at the end of a test period since the electrical intensity of the stimulation reaching the nerve may change in each session. The healthcare personnel can start the session after verifying access to the nerve by tracking the motor or sensory response. During the test and treatment, the patient waits for the session to end while keeping their leg stable on a chair. Since the management of this treatment is carried out in the hospital, compliance with multiple treatments is limited, especially in elderly cases with more disease frequency.

The rate of dropout of the treatment after the beginning of the treatment is around 50%. Even though a treatment process at home with devices for PTNS treatment with electrodes through the skin seems theoretically possible, it is not possible for the patient to make dose adjustments that are carried out in each session to start the treatment, and the health care provider cannot determine whether these treatments are done or whether they are done properly. If the patient receives a two-way application of treatment, then treatment time is doubled and the patient will have to come to the hospital twice a day (e.g., morning and evening). Moreover, while treatments with needles are minimally invasive, the patient will still require two needle injections. In some of the patients who recovered after PTNS treatment, the disease relapses in the long term. In this case, fewer and more intermittent reinforcement sessions can be used. In this case, the treatment will have to be continued in the hospital and by the healthcare personnel, which further complicates treatment for the patient.

Existing treatments are also challenged by a placebo effect and a nocebo effect. Without involvement of the patient, the placebo and nocebo effects are completely under the control of the healthcare personnel and cannot be predicted. Since the PTNS devices do not contain urinary diaries and the treatment device is used by the healthcare personnel, the patient might erroneously think that the treatment is working without understanding the link between the urinary diary practice, the treatment apparatus, and the patient. The nocebo effect, which is opposite of the placebo effect, relates to reports about side effects or the fact that the treatment is not working. The nocebo effect can negatively affect the treatment results if the patient erroneously thinks that the treatment is not working.

The systems and methods described herein address the challenges described herein and provide a wearable "data driven system solution" for home-remote treatment with transcutaneous electrical nerve stimulation to treat overactive bladder, fecal incontinence, pelvic pain, sexual dysfunction indications, a combination of such conditions or similar conditions.

In some embodiments, the system includes a neuromodulation device, a mobile application, and a web service. The neuromodulation device is provided to the patient as a wearable technology, without any cables, to allow for patient's mobility. The neuromodulation device is non-implantable but can be attached to the skin of the patient to stimulate the nerves transcutaneously. The neuromodulation device can output energy to stimulate the nerves (e.g., tibial nerve) of the patient. The neuromodulation device can be any nerve stimulation device for stimulating the nerves of the patient by application of energy, such as, electrical, magnetic or thermal energy. In some embodiments, the neuromodulation devices can stimulate the nerves of the patient by applying electrical energy. The mobile application or the web service can apply the operations described herein to monitor and control the stimulation provided by the device.

The treatment electrodes can be on the neuromodulation device itself. The neuromodulation device does not require a separate connection with a cable. Thus, the patients can continue their treatments from home, which advantageously provides the benefit of being monitored by the physician via the web service. The patient can adhere the neuromodulation device to the treatment site on their body without a healthcare professional. The implementation of the treatment can occur remotely under the control of the healthcare professional. The system enables the treatment to be done remotely and at home without a healthcare professional to monitor the treatment and its effectiveness. The system can provide validated assessment tools, such as the OAB-V8 (e.g., Overactive Bladder-Validated 8-question) questionnaire and the urinary diary for the treatment of urinary incontinence in the mobile application. The system enables the remote monitoring of the delivery of the adequate treatment dose during the treatment and it ensures the effectiveness of the treatment.

The present disclosure provides numerous technical advantages. One technical advantage of the present disclosure includes providing visual and auditory feedback to increase the effectiveness of the treatment. Another technical advantage is that the system provides a personalized system solution that can be operated if the identifier of the neuromodulation device matches the patient's identifier as registered in the web service. The present disclosure can utilize indoor positioning devices (e.g., beacons and trackers) and the mobile device executing the mobile application to determine the location of the patient during treatment to provide notifications according to the location of the patient in places such as kitchen, toilet, bathroom, and the time they spend in those locations. The present disclosure can use the location information with the information provided in the urinary diary to optimize the treatment plan for the patient. The location information can be used to help the patient answer the urinary diary questions accurately. As the urinary diary is the validated assessment tool to measure treatment outcome at the beginning (as reference), middle, and end of treatment, it is important that the data provided by patient is as accurate as possible. The accuracy will help the health care professional better assess treatment success data and base their treatment adjustment decisions on correct data.

Another technical advantage is the ability for the neuromodulation device to operate independently of the mobile application. For example, the neuromodulation device and the mobile application can communicate via Bluetooth or any other communication protocol. During the treatment, even if the connection between the neuromodulation device and the mobile application disconnect (e.g., the mobile device is far away or the battery of the mobile device runs out), the neuromodulation device can continue to deliver the treatment by operating in a stand-alone mode. While the neuromodulation device is disconnected, the neuromodulation device can store information about treatment activities in a volatile or nonvolatile memory (e.g., EEPROM). upon reconnecting with the neuromodulation device, the neuromodulation device can transfer previously completed treatment activities from the memory to the mobile application.

Another technical advantage is that a neuromodulation device of the present disclosure can include a DC/DC step-up converter. The output voltage of the DC/DC step-up converter can be automatically increased or decreased according to the total impedance of body the neuromodulation device is adhered as well as the treatment current need. Changing the voltage allows for more efficient battery use, instead of simply providing constant current and at maximum voltage.

Another technical advantage is that in response to each treatment protocol, the efficacy of the treatment can be recorded quantitatively, such as with urinary diary and validated questionnaires, as a data set stored in the web service. Based on the data set, the web service can generate or provide artificial intelligence-assisted recommendation protocols for future treatments.

Another technical advantage includes the mobile application instructing the patient on how to apply the neuromodulation device to their body. For example, the patient can press the "start" button on the mobile application to see the location of where the neuromodulation device will be placed on the leg with the help of visual animation and/or video and/or augmented reality. These instructions can increase the repeatability of positioning for the patient.

Another technical advantage is that the transcutaneous posterior tibial nerve stimulation device and the mobile application can be remotely monitored by a web service. The web service can monitor the course of treatment in the treatment of urinary incontinence, fecal incontinence, pelvic pain, and sexual dysfunction. The web service can manage the registration of the patient to the system, the registration of the neuromodulation device, the remote treatment, and the information input and displayed via the web service. The web service, monitors and controls the neuromodulation device and the mobile application. The web service monitors the neuromodulation device and mobile application by collecting and receiving treatment activities from the neuromodulation device or mobile application. The treatment activities can be generated by the neuromodulation device or mobile application (e.g., location or treatment current) or provided by the patient (urinary diary, validated questionnaires). The web service controls the neuromodulation device by transmitting the treatment protocol assigned by the healthcare professional via mobile application to the neuromodulation device. The web service controls the mobile application by managing which notification can be sent and when. The web service also sends notifications (such as e-mails, SMS, etc.) to the healthcare professional regarding the efficacy of the treatment.

The present disclosure enables the patient to be an active participant of the treatment process in the treatment application. The fact that the treatment is monitored and that the patient knows and feels assured that the treatment is monitored increases adherence to the treatment.

One advantageous component of the present disclosure is the mobile application that enables for the communication of the patient with the web service and the neuromodulation device.

Another advantageous component of the present disclosure is that the neuromodulation device includes a constant current source that is adjusted based on the opposing impedance and regulates the current constantly. Another advantageous component of the present disclosure is that the neuromodulation device includes an adjustable DC/DC converter that feeds the constant current source and that is a voltage boost type converter. Another advantageous component of the present disclosure is that the neuromodulation device includes a controller that runs the desired algorithm. Another advantageous component of the present disclosure is that the neuromodulation device includes a "−" electrode and a "+" electrode that enable the electrical pulses of the neuromodulation device to be transmitted to the skin with hydrogels. Another advantageous component of the present disclosure is that the neuromodulation device communicates with tracker device to track the patient for enhancing the urinary diary. Another advantageous component of the present disclosure is that the neuromodulation device includes an audio and visual communication circuit that indicates that the treatment has started and continues to provide visual and audible notifications.

FIG. 1 depicts a neuromodulation system comprising a neuromodulation device 1, a mobile application 2, and a web service 3. The system can be a wearable "system solution" for home-remote treatment with transcutaneous delivery of electrical nerve stimulation of overactive bladder, fecal incontinence, pelvic pain, and sexual dysfunction indications. The neuromodulation device 1, the mobile application 2, and the web service 3 can communicate via connection 4A (e.g., Bluetooth connection) or connection 4B (e.g., Wi-Fi connection). The web service 3 can be for registration, follow-up, and monitoring of treatment. The web service 3 can maintain or assign the ID of the neuromodulation device to the ID of the patient 6.

The neuromodulation device 1 (also referred to as a transcutaneous posterior tibial nerve neuromodulation device or a nerve stimulating device), can be used at home and can be monitored remotely. The neuromodulation device 1 is wearable, which enables remote treatment.

The mobile application 2 can provide instructions that allow the patients to follow the treatment plan themselves without requiring supervision by the healthcare provider 7. The mobile application 2 can provide the patient with validated assessment tools such as OAB-V8 questionnaire and a urinary diary for urinary incontinence to measure, monitor, and intervene with the effectiveness of the neuromodulation device 1 and the treatment. In some embodiments, the questionnaires can be assessment tools for female sexual function index (FSFI) for sexual dysfunction, Wexner score for fecal incontinence, or SF-36 Short Form for pelvic pain.

The web service 3 can enable the healthcare provider 7 to configure the treatment. For example, the healthcare professional can select a neuromodulation device 1 for the patient 6 and configure a treatment plan for the patient 6. The web service 3 can provide a notification that the treatment has been completed to be sent to the healthcare provider 7 of the patient 6. For example, the healthcare provider 7 can evaluate the treatment efficacy by accessing the validated questionnaires and urinary diaries provided by the patient 6 via the mobile application 2.

When the patient 6 applies the neuromodulation device 1 and interacts with the mobile application 2, the neuromodulation device 1 can apply the treatment protocol assigned to the patient 6 by the healthcare professional via the web service 3. The patient does not need to make any adjustments (except to the treatment current for the treatment session). By monitoring the treatment, the patient 6 knows and feels assured that they are being treated, which can increase adherence to the treatment.

Section A: Neuromodulation Device

Figure 2A:
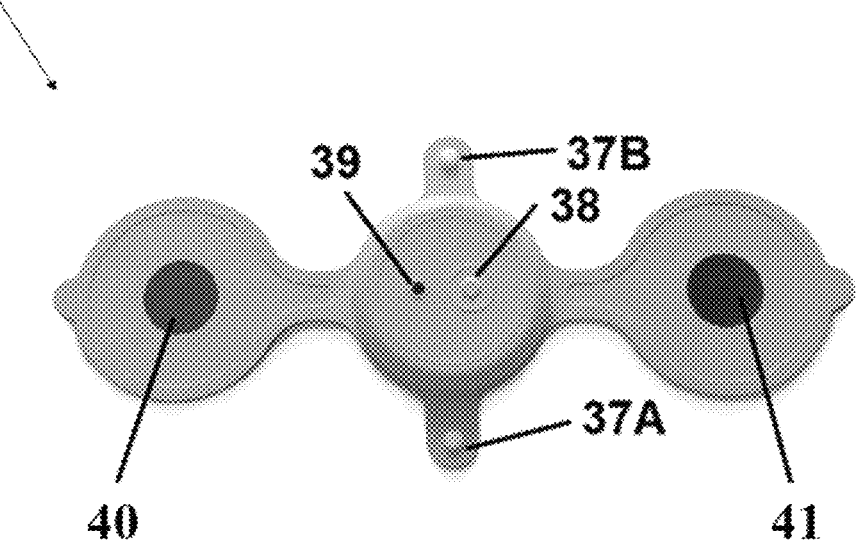
FIG. 2A depicts a view of the neuromodulation device for applying to a patient.
Figure 2B:
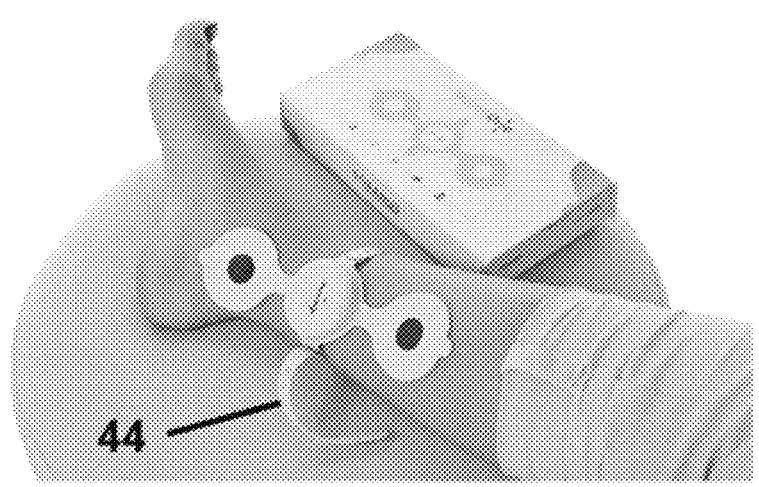
FIG. 2B depict a view of the neuromodulation device applied to a patient.

FIGS. 2A and 2B depict views of the neuromodulation device 1 for applying electrical stimulation to a patient.

As noted above, the neuromodulation device 1 can output energy to stimulate the nerves (e.g., tibial nerve) of the patient 6. In some embodiments, the stimulation is applied transcutaneously. The neuromodulation device can be any nerve stimulation device for stimulating the nerves of the patient 6 by application of energy, such as, electrical, magnetic or thermal energy. In some embodiments, the neuromodulation devices can stimulate the nerves of the patient by applying electrical energy, but it should be noted that while the instant methods and systems are discussed in reference to electrical stimulation, other types of energy can also be used.

The neuromodulation device 1 can include a positive treatment electrode 41 and a negative treatment electrode 40. The neuromodulation device 1 can include a light indicator 39. The neuromodulation device 1 can include a button 38. The neuromodulation device 1 can include strap connectors 37A and 37B. The neuromodulation device 1 can include a strap 44.

The neuromodulation device 1 can include the positive treatment electrode 41 and the negative treatment electrode 40. The distance between the positive treatment electrode 41 and negative treatment electrode 40 can make the treatment effective over the posterior tibial nerve and anatomically in accordance with the general patient profile. It is also possible to make an adjustable version of the distance of the electrodes while keeping them on the neuromodulation device 1. The positive treatment electrode 41 and the negative treatment electrode 40 enable the neuromodulation device 1 to be wearable and usable by the patient without the direct supervision of a healthcare professional.

The neuromodulation device 1 can include at least one light indicator 39 for generating visual indicators. The light indicator can be an LED (e.g., red and green). The neuromodulation device 1 can turn the light indicator 39 on and off to indicate visual warnings. In some embodiments, the neuromodulation device 1 can receive a signal from the mobile application 2 to turn the light indicator 39 on and off. The mobile application 2 can receive the signal from the web service 3. The signal can specify a pattern (e.g., blink every 3 seconds) or color of the light indicator 39 (e.g., turn on red LED).

The neuromodulation device 1 can include the button 38 to turn the neuromodulation device 1 on and off. For example, the neuromodulation device 1 can be turned on by pressing the button 38. Responsive to toggling of the power button, the neuromodulation device 1 can turn on or off. For example, the neuromodulation device 1 is turned on by keeping the button 38 on the neuromodulation device 1 pressed for a minimum of 3 seconds to turn on the neuromodulation device 1.

The neuromodulation device 1 can include strap connectors 37A and 37B for coupling to the strap 44 to secure the neuromodulation device 1 to the patient. As shown in FIG. 2B, the neuromodulation device 1 can be positioned on the leg for treatment and fixed with the strap 44. The neuromodulation device 1 is can start the treatment when the negative treatment electrode 40 of the tibial nerve region is placed just above the tarsal tunnel, and the positive electrode 41 is placed parallel to the orientation of the nerve.

Figure 2C:
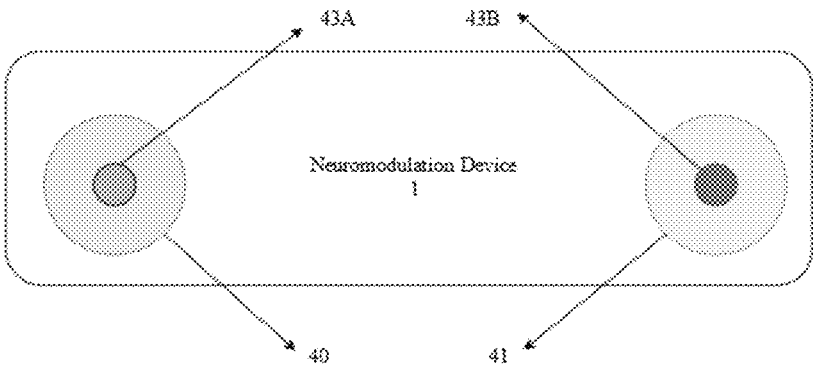
FIG. 2C depicts views of feedback electrodes of the neuromodulation device.

FIG. 2C depicts feedback electrodes 43A and 43B adjacent to the treatment electrodes 40 and 41 of the neuromodulation device 1. The feedback electrodes 43 can be adhered to the patient 6 when the neuromodulation device 1 is positioned on the patient 6. The neuromodulation device 1 can use the feedback electrodes 43 to generate electrical feedback measurements (e.g., voltage or current) for identifying the nerve threshold at which the patient 6 reacts to neuromodulation. The neuromodulation device 1 can use the feedback electrodes 43A and 43B to measure electrical signal (voltage) in order to keep track of the changes at a nerve threshold and estimate values such as the time for the nerve (excitability) threshold level to return to rest level. The neuromodulation device 1 can transmit the feedback measurements to the mobile application 2 or the web service 3

(via the mobile application 2). The mobile application 2 or the web services 3 can receive the feedback measurements.

Once the nerve threshold is identified, the neuromodulation device 1 can use the feedback electrodes 43 to measure the feedback measurements after administering neuromodulation. With the feedback electrodes 43 placed on the neuromodulation device, the mobile application 2 or the web services 3 can receive electrical signals and impedance as a response to the administration of neuromodulation. For example, the neuromodulation device 1 can use the feedback electrodes 43 to generate the feedback measurements at five minutes after administering neuromodulation or on an hourly basis.

Figure 2D:
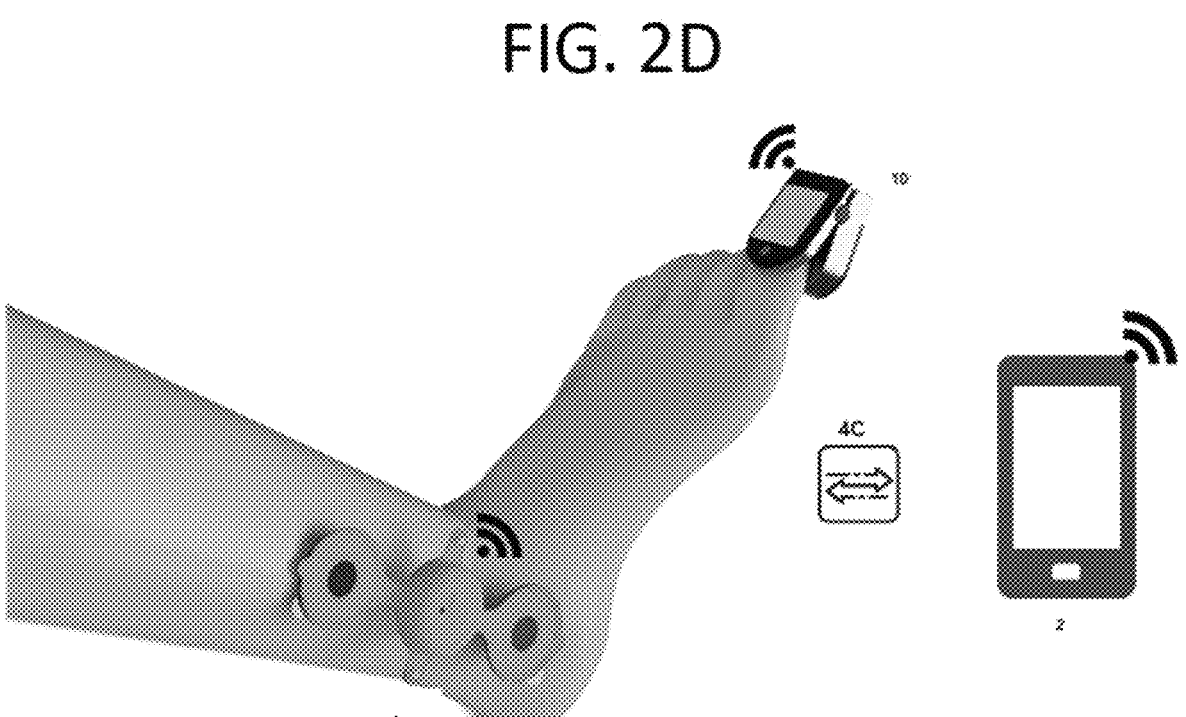
FIGS. 2D and 2E depict views of the sensor device for verifying adherence of the neuromodulation device.
Figure 2E:
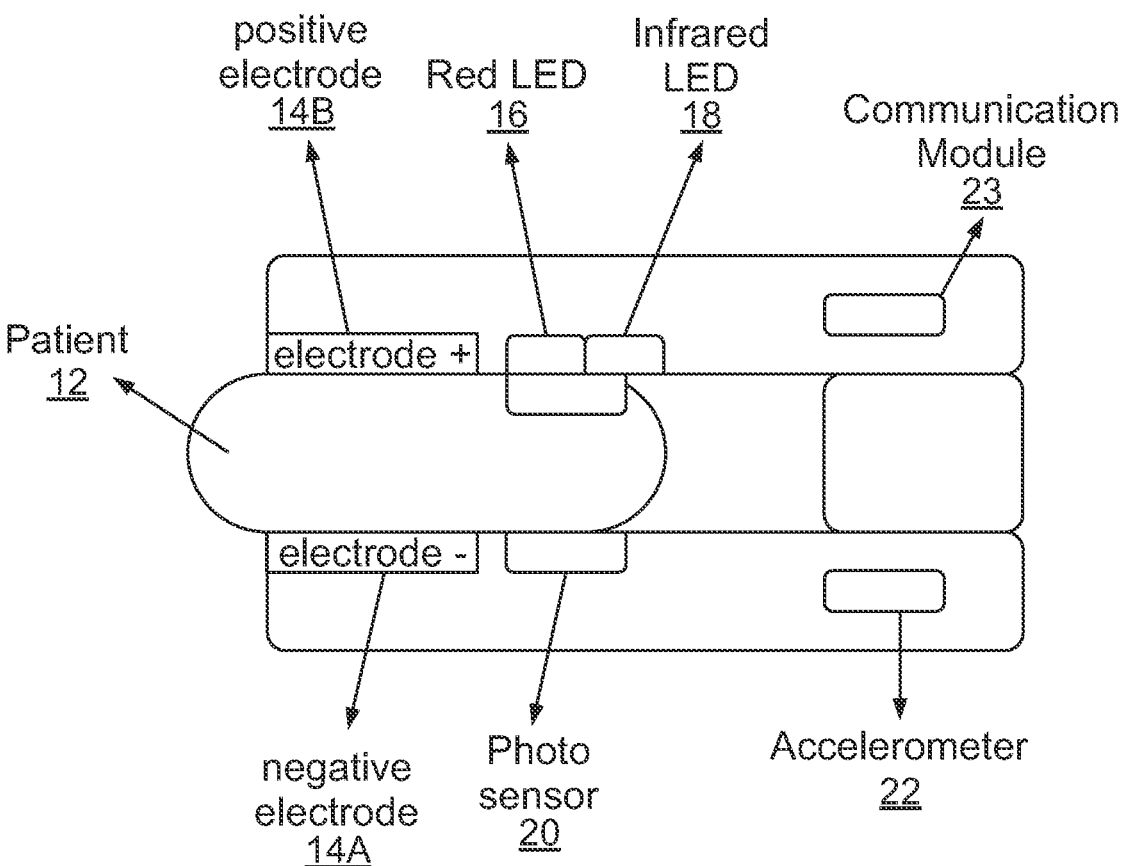

FIGS. 2D and 2E depict views of the sensor device 10 for verifying adherence of the neuromodulation device 1. The sensor device 10 can generate measurements of the patient. The sensor device 10 can generate measurements such as electrical signals, oxygen concentration, and tickling movements. The measurements can be indicative of the changes in blood flow and transmit the measurements to the mobile application 2. For example, a neuromodulation device 1 that is correctly positioned on the patient will causes changes in the patient's blood flow by stimulating the tibial nerve. The sensor device 10 can transmit the measurements to the mobile application 2, which can analyze the measurements to verify correct placement of the neuromodulation device 1. The sensor device 10 is configured to be attached to the patient's extremity 12. For example, the sensor device 10 can be attached to the patient's toe of the leg to which the neuromodulation device 1 is adhered.

The sensor device 10 and the neuromodulation device 1 can establish and maintain a connection 4C for communications. For example, the neuromodulation device 1 and the sensor device 10 can establish a Bluetooth connection. It is contemplated that the sensor device 10 can be connected to the neuromodulation device 1 via a wired connection. The sensor device can include a communications module 23 for establishing communications. In some embodiments, the communication circuit is a Bluetooth circuit. In some embodiments, different communication circuits can be used. The sensor device 10 can use the communications circuit to exchange treatment activities by communicating with the neuromodulation device 1 or the mobile application 2. The communications circuit can be a Bluetooth circuit that can establish or maintain a Bluetooth connection to the mobile device via the Bluetooth protocol. This unit can be a communication circuit such as Bluetooth, wireless. Indoor positioning is calculated based on TX power in accordance with beacon technology.

The sensor device 10 and the mobile application 2 can establish and maintain a connection (e.g., connection 4B) for communications. For example, the mobile device executing the mobile application 2 and the sensor device 10 can establish a Bluetooth connection or an NFC connection. It is contemplated that the sensor device 10 can be connected to the mobile device via a wired connection. In some embodiments, the sensor device 10 communicates with the mobile device via the neuromodulation device 1. For example, the sensor device 10 can transmit packets to the neuromodulation device 1, which forwards the packets to the mobile application 2. In some embodiments, the sensor device 10 communicates with the neuromodulation device 1 via the mobile device. For example, the sensor device 10 can transmit packets to the mobile device, which forwards the packets to the neuromodulation device 1. Such communications via an intermediary device can be beneficial when one of the devices is unavailable (e.g., too far away) for a direct connection.

The sensor device 10 can include sensing electrodes 14A and 14B to be attached to the patient's toe. The sensing electrodes 14A and 14B can be a pair of electrodes such that sensing electrode 14A is the negative (−) terminal and the sensing electrode 14B is the positive (+) terminal. The sensor device 10 can detect electrical signals via the electrodes coupled to the patient. The sensor device 10 can detect the frequency and amplitude of the electrical signals. The sensor device 10 can generate packets identifying the detected frequency and amplitude of the electric signals. The sensor device 10 can transmit the packets to the mobile application 2 or the neuromodulation device 1 via the connection.

The sensor device 10 can include a pulse oximeter for measuring oxygen concentration of the patient. The pulse oximeter can include a red LED 16 and an infra-red LED 18 that faces a photo sensor 20. The pulse oximeter can cause the red LED 16 to emit red light (e.g., wavelength of 660 nm), and the infra-red LED 18 to emit infra-red light (e.g., wavelength of 940 nm). The absorption of light at these wavelengths differs between blood loaded with oxygen and blood lacking oxygen: oxygenated blood absorbs infrared light and allows red light to pass whereas deoxygenated blood allows infrared light to pass through while absorbing red light. The pulse oximeter can cause the photo sensor 20 to measure the light that is passed through the patient's blood. Based on the light measurements, the pulse oximeter can distinguish oxyhemoglobin to calculate the oxygen concentration of the patient. The pulse oximeter can identify pulse sequences in the light measurements to identify the pulse of the patient. The sensor device 10 can generate packets identifying the calculated oxygen concentration and pulse. For example, the sensor device 10 can generate packets identifying an oxygen concentration of 99% and a pulse of 65 BPM. The sensor device 10 can transmit the packets via the connection to the mobile application 2 or the neuromodulation device 1.

The sensor device 10 can include an accelerometer 22 for measuring acceleration to detect movements of the patient. For example, the accelerometer can be a micro-electro-mechanical system (MEMS). The sensor device 10 can use the accelerometer to detect movements of the patient. For example, the sensor device 10 can use the accelerometer to detect a motor response such as toe movements caused by tingling or tickling sensations from neuromodulation. The sensor device 10 can generate packets identifying the detected movements. For example, the sensor device 10 can generate packets identifying that the patient moved their toe towards the leg. The sensor device 10 can transmit the packets via the connection. The sensor device 10 can transmit the packets via the connection to the mobile application 2 or the neuromodulation device 1.

The neuromodulation device 1 or the mobile application 2 can identify or verify proper placement of the neuromodulation device 1 based on the measurements generated by the sensor device 10. The neuromodulation device 1 or the mobile application 2 can receive the packets that include the measurements from the electrodes, accelerometer, and pulse oximeter of the sensor device 10. The neuromodulation device 1 or the mobile application 2 can identify the frequency and amplitude values, movement values, pulse value, and oxygen concentration of the patient 6 from the measurements in the packets. The neuromodulation device 1 or the mobile application 2 can identify or verify proper placement if the measurements indicate that the patient 6 is moving their toe or if the electrical frequency and amplitude, pulse, or oxygen concentration are elevated.

The neuromodulation device 1 or the mobile application 2 can maintain threshold values indicative of proper placement of the neuromodulation device 1. The mobile application 2 can maintain a threshold oxygen concentration, threshold pulse value, threshold movement values, or a threshold frequency and threshold amplitude that indicate that the neuromodulation device 1 is properly positioned on the patient to provide neuromodulation. For example, the threshold movement values can be indicative of movements caused by tingling or tickling caused by a neuromodulation device 1 that is properly positioned on the patient. In another example, the threshold oxygen concentration can be indicative of increased oxygen concentration caused by a neuromodulation device 1 that is properly positioned on the patient. In another example, the threshold pulse value can be indicative of increased pulse caused by a neuromodulation device 1 that is properly positioned. In another example, the threshold frequency and amplitude value can be indicative of the frequency and amplitude of electrical signals (e.g., treatment current) output by the neuromodulation device 1. In some embodiments, the threshold amplitude value can be indicative of the amplitude of electrical signals (e.g., treatment current) output by the neuromodulation device 1. In some embodiments, the mobile application 2 can receive, from the neuromodulation device 1, the frequency and amplitude of the treatment current applied by the neuromodulation device 1 to the patient. In some embodiments, the mobile application 2 can store the frequency and amplitude of the treatment current applied by the neuromodulation device 1 to the patient. In some embodiments, the mobile application 2 can identify (e.g., from a stored lookup table) the frequency and amplitude of the treatment current based on the treatment current selected by the patient via the mobile application 2.

The neuromodulation device 1, the mobile application 2, or the web service 3 can modify or update the threshold values. The mobile application 2 or the web service 3 can receive updates to the threshold values. In some embodiments, the neuromodulation device 1 or the mobile application 2 can receive the updates from the web service 3. In some embodiments, the neuromodulation device 1, the mobile application 2, or the web service 3 can receive the updates via selections made by the patient on the mobile application 2. In some embodiments, the mobile application 2 or the web service 3 can generate the updates based on historical measurements. The mobile application 2 or the web service 3 can use machine learning or artificial learning techniques to update or modify the threshold values. For example, the mobile application 2 or the web service 3 can identify that the patient has a lower-than-average increase in oxygen concentration level caused by neuromodulation, and the mobile application 2 or the web service 3 can decrease the threshold oxygen concentration level accordingly.

In some embodiments, the measured movement values might be caused by the patient 6 moving around or walking around. To avoid falsely classifying walking movements as tingling caused by neuromodulation, the neuromodulation device 1 or the mobile application 2 can compare movements of the toe (e.g., likely caused by neuromodulation) to the movements of the leg (e.g., likely caused by the patient 6 moving around).

The neuromodulation device 1 or the mobile application 2 can compare movement measurements generated by the accelerometer 22 of the sensor device 10 and movement measurements generated by the accelerometer 71 of the neuromodulation device 1. The neuromodulation device 1 or the mobile application 2 can receive, from the sensor device 10, the movement measurements generated by the accelerometer 22. In some embodiments, the sensor device 10 can transmit the movement measurements generated by the accelerometer 22 to the neuromodulation device 1. The neuromodulation device 1 can forward the movement measurements generated by the accelerometer 22 to the mobile application 2. In some embodiments, the neuromodulation device 1 can transmit the movement measurements generated by the accelerometer 71 to the mobile application 2. In some embodiments, the mobile application 2 can receive, from the neuromodulation device 1 or the sensor device 10, the movement measurements generated by the accelerometer 22. In some embodiments, the mobile application 2 can receive, from the neuromodulation device 1, the movement measurements generated by the accelerometer 71.

The neuromodulation device 1 or the mobile application 2 can compare the movement measurements from the accelerometer 22 and the accelerometer 71. If the difference between both movement measurements is less than a threshold (e.g., the movements are similar since the patient 6 is moving their leg and thus their toe), then the neuromodulation device 1 or the mobile application 2 can generate a request for the patient 6 to keep their leg still for the measurement of their toe movements to be more accurate. If the neuromodulation device 1 generated the comparison, then the neuromodulation device 1 can transmit the comparison to the mobile application 2 or the web service 3. The mobile application 2 can receive the request and generate an interface requesting the patient 6 to keep their leg still for the measurement of their toe movements to be more accurate. If the mobile application 2 generated the comparison, then the mobile application 2 can generate an interface to request the patient 6 to keep their leg still for the measurement of their toe movements to be more accurate. In some embodiments, the mobile application 2 can transmit, to the web service 3, an indication that the interface was generated. In some embodiments, the neuromodulation device 1, mobile application 2, or the web service 3 can set a flag indicating that the neuromodulation device 1 is not properly positioned if the difference between both movement measurements is less than the threshold.

The neuromodulation device 1 or the mobile application 2 can identify or verify proper placement of the neuromodulation device 1 by identifying that the received measurements satisfy the threshold values. The neuromodulation device 1 or the mobile application 2 can identify that the measured movement values satisfy the threshold movement values by comparing the measured movement values and the threshold movement values. For example, the mobile application 2 can identify that measured movements caused by tickling or tingling sensations satisfy the threshold movement values. The mobile application 2 can identify that the measured oxygen concentration satisfies the threshold oxygen concentration by comparing the measured oxygen concentration and the threshold oxygen concentration. For example, the mobile application 2 can identify that a measured oxygen concentration that is elevated due to increased oxygen saturation in the blood satisfies the threshold oxygen concentration. The mobile application 2 can identify that the measured pulse value satisfies the threshold pulse value by comparing the measured pulse value and the threshold pulse value. For example, the mobile application 2 can identify that a measured pulse value that is elevated due to increased blood flow satisfies the threshold pulse value. The mobile application 2 can compare the measured frequency and amplitude values to the frequency and amplitude of the treatment current applied by the neuromodulation device 1 to the patient. The mobile application 2 can identify, based on the comparison, that the measured frequency and amplitude values are within a threshold frequency and amplitude value of the frequency and amplitude of the treatment current applied by the neuromodulation device 1 to the patient.

The mobile application 2 can identify or verify proper placement of the neuromodulation device 1 responsive to identifying that several of the received measurements satisfy the threshold values. For example, the mobile application 2 can identify or verify proper placement of the neuromodulation device 1 responsive to identifying that both the measured oxygen concentration and measured pulse value satisfy the threshold oxygen concentration and threshold pulse value. In another example, the mobile application 2 can identify or verify proper placement of the neuromodulation device 1 responsive to identifying that the measured oxygen concentration, measured pulse value, measured movement values, and measured voltage values all satisfy their respective thresholds.

The web service 3 can identify or verify proper placement of the neuromodulation device 1 by identifying that the measurements received from the neuromodulation device 1 satisfy the threshold values. The mobile application 2 can transmit the received measurements to the web service 3. The web service 3 can receive the measurements and compare them to the threshold values to identify or verify proper placement of the neuromodulation device 1.

Referring to FIGS. 2C-2E, in some embodiments, the nerve threshold is based on the measurements from the sensor device 10 and the feedback electrodes 43. In some embodiments, the neuromodulation device 1, mobile application 2, or the web services 3 identifies the nerve threshold based on the measurements from the sensor device 10. In some embodiments, the neuromodulation device 1, mobile application 2, or the web services 3 can identify the changing sensitivity based on the measurements from the sensor device 10 satisfying their respective measurement thresholds. For example, as described herein, the measurements from the sensor device 10 can indicate when the toe of the patient 6 starts moving. The neuromodulation device 1, mobile application 2, or the web services 3 can update the nerve threshold to the treatment current at which measurements from the sensor device 10 indicate that the patient 6 is moving their toe in a tickling movement.

The mobile application 2 or the web service 3 can use the nerve threshold to generate treatment schedules for the patient 6. The neuromodulation device 1, mobile application 2, or the web services 3 can identify changes in the nerve threshold to optimize the treatment schedules and treatment current. For example, the patient 6 can become more sensitive to neuromodulation over time and the nerve threshold would decrease, so the neuromodulation device 1 could apply less treatment current. In another example, the patient 6 can become less sensitive to neuromodulation over time and the nerve threshold would increase, so the neuromodulation device 1 could apply increased treatment current.

The web service 3 can use the nerve threshold to modify the treatment protocol regarding session duration and the time interval set between sessions. For example, by measuring it for each patient 6, the web service 3 can identify that a patient A benefits from neuromodulation best, if he/she gets a 20-minute session followed by a 10-minute break then another 20 minutes of neuromodulation. Another change might be about the time between 2 sessions. For example, for a patient A this period may be 2 days (because their nerve's threshold level is returning to rest level in 2 days-time) but for a patient B it might be 4 days. The web service 3 can generate individualized treatment protocols based on each patient's specific assessment, data from the neuro-modulation device 1, sensor device 10, urinary diary, or feedback electrodes.

Figure 3A:
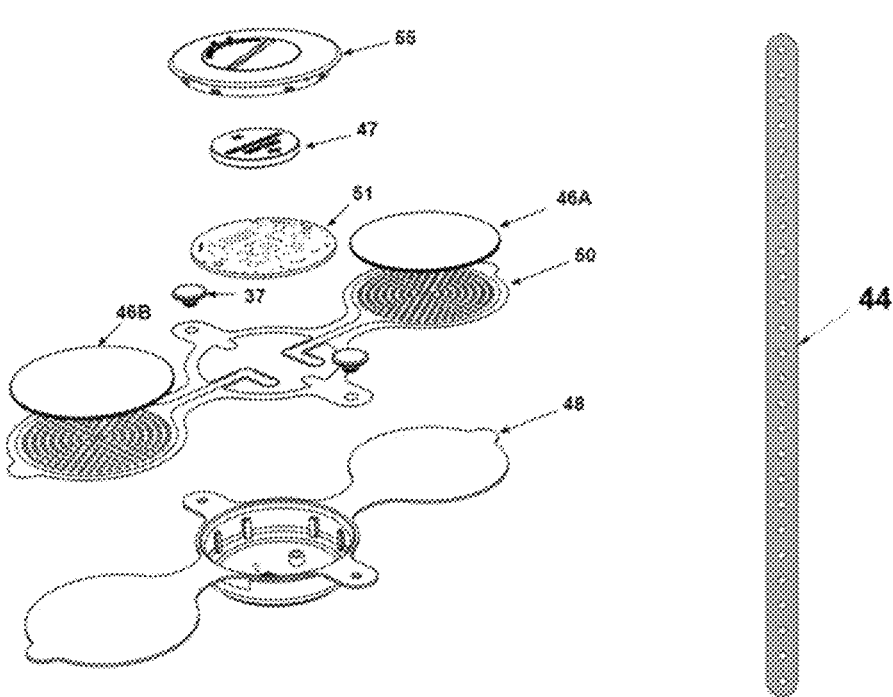
FIGS. 3A and 3B depict cross sectional views of the components of the neuromodulation device.
Figure 3B:
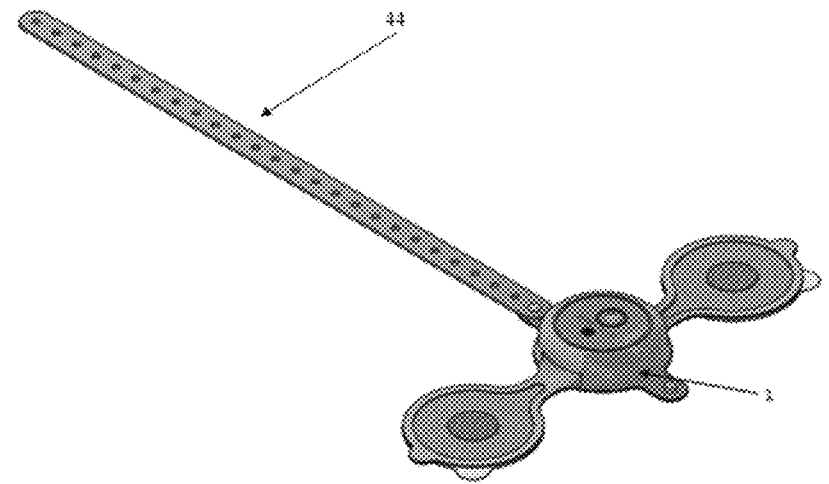

FIGS. 3A and 3B depict cross sectional views of the components of the neuromodulation device 1. The power source 47 enables the operation of the neuromodulator device 1. In some embodiments, the power source 47 is one or more batteries. For example, two CR2430 batteries. The batteries can be non-rechargeable and called primary bat-teries. In some embodiments, the neuromodulation device 1 can include one or more rechargeable batteries. The batteries can provide energy to the components described herein.

The neuromodulation device 1 can include a longitudinal body such as a silicone body 48. The silicone body 48 is a flexible structure that creates the integrity of the neuromodu-lation device 1 and all other components are assembled on this silicone body. The flexible body can include Liquid Silicon Rubber, or any other material generally used in medical applications. The material in the silicone body 48 can ensure that the neuromodulation device 1 is compatible with its wearable and flexible structure.

The neuromodulation device 1 can include a central body such as the plastic body, which can provide protection against external impact of the electronic components with the rigidity of the neuromodulation device 1. The plastic body can contribute to the functioning of the buzzer 73, button 38, and the light indicator 39.

The neuromodulation device 1 can include conductive printed film 50, which can be a symmetrical structure that couples to the treatment electrodes 40 and 41 by connecting to the electrode connection points on the printed circuit board 51. For example, the AgCl printing on PET film can form a conductive structure. The non-conductive surface that is contact to with the silicone body 48 is self-adhesive and is adhered to the silicone body 48 by applying pressure. The conductive printed film 50 can be thin, such as 50 µm PET film thickness, to avoid affecting the flexibility of the silicon body 48.

The conductive printed film 50 can enable the electric current to be applied to the body via the hydrogel 46A and 46B adhered on the conductive print. After the hydrogels 46A and 46B are adhered, the neuromodulation device 1 can be ready for use. Negative treatment electrode 40 and positive treatment electrode 41 are the conductive surfaces that enables the electrical current pulses of the neuromodu-lation device 1 to be transmitted to the skin via the hydrogels 46A and 46B.

The neuromodulation device 1 can include a printed circuit board (PCB-A) 51. The electronic components that provide the function of the neuromodulation device 1 can be assembled on the PCB-A 51 that provides the electrical connections between these electronic components. In addi-tion, the plastic body cover 55 can cover the battery 47 that provides the energy to the neuromodulation device 1. In some embodiments, the cover 55 can be opened to reveal internal electronics of the neuromodulation device 1. The neuromodulation device 1 can include plastic pins 37 that allow the silicon body 48 to be mounted on both sides to allow the neuromodulation device 1 to be used with a strap 44.

Figure 4:
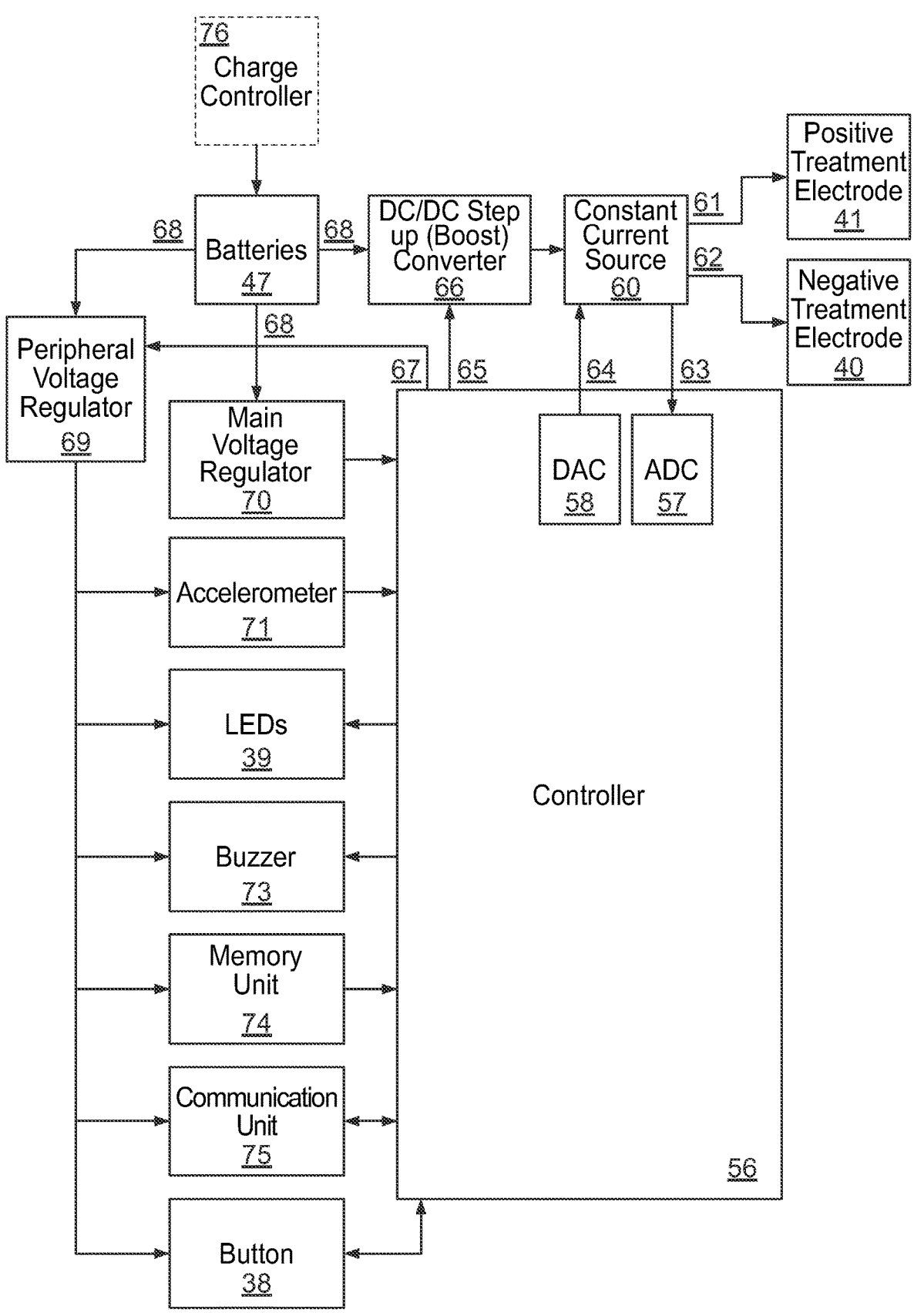
FIG. 4 is a block diagram of components of the printed circuit board inside the neuromodulation device.

FIG. 4 is a block diagram of components of the printed circuit board 51 inside the neuromodulation device 1. The functions of the neuromodulation device 1 can be provided or implemented by the controller 56, which can execute or run the desired algorithm. The controller 56 can interface with and manage the components of the neuromodulation device 1.

The microcontroller can include one or more processors configured to execute machine readable instructions for managing the neuromodulation device 1. The controller can include digital to analog (DAC) 58, analog to digital (ADC) 57, and digital input/output units.

The neuromodulation device 1 can include a current source 60. The current source can receive a signal from the microcontroller with instructions to generate the current according to the treatment protocol. The current source can administer the treatment protocol by generating an electric current according to the impedance of the surface to which it is adhered. The controller 56 can receive feedback pro-vided by the ADC 57 from the constant current source 60 to read the voltage difference 63 between the positive electrode terminal 41 and the negative electrode terminal 40 and the treatment current. The electrodes include the conductive (e.g., AgCl) print structure on the PET (e.g., plastic based) film 50. This conductive print can be mechanically con-nected to the constant current source 60 located on the electronic card inside the neuromodulation device 1.

Figure 5:
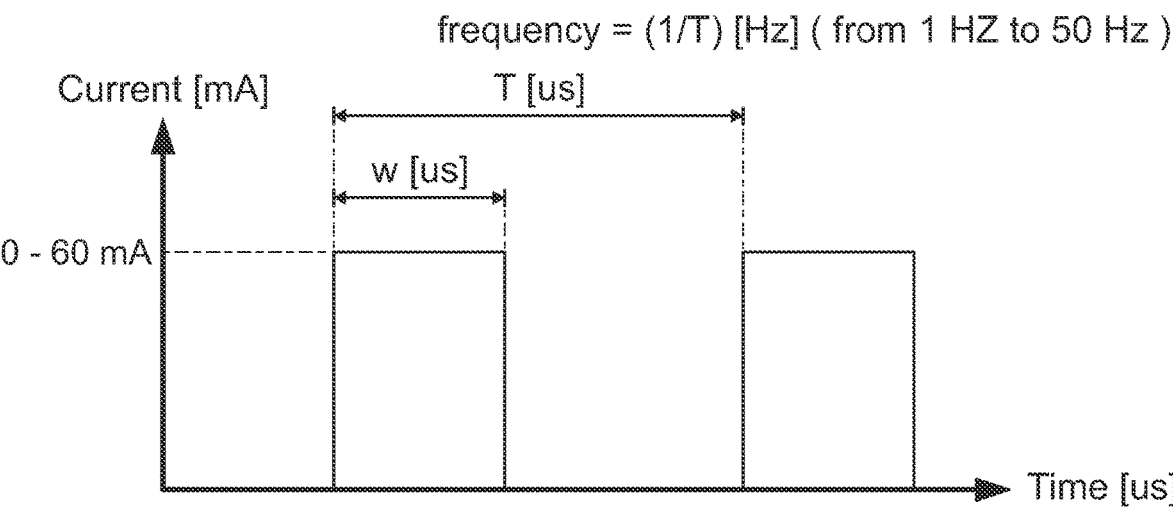
FIG. 5 depicts a time-varying waveform of the monophasic constant treatment current of the neuromodulation device.

FIG. 5 depicts a time-varying waveform of the monopha-sic constant treatment current of the neuromodulation device 1 transmitting electrical current pulses to the skin. The controller 56 can use the DAC 58 to provide the constant current pulse reference 64 such as the width, amplitude, and frequency of the targeted constant current pulses. As shown in FIG. 5, the controller 56 can cause the current source 60 to generate monophasic current pulses up to 60 mA (60 V at 1000-ohm load), pulse duration (40-400 us), and at frequen-cies from 1 Hz to 50 Hz for neuromodulation. The electrical pulse applied by the electrodes can be constant current—mono-phasic rectangular pulse. The current source 60 can provide monophasic constant electrical current pulses from 0 mA to 60 mA with 0.5 mA increments via electrodes 40 and 41 and hydrogel 46A to the body surface to which it is adhered for treatment.

Figure 6A:
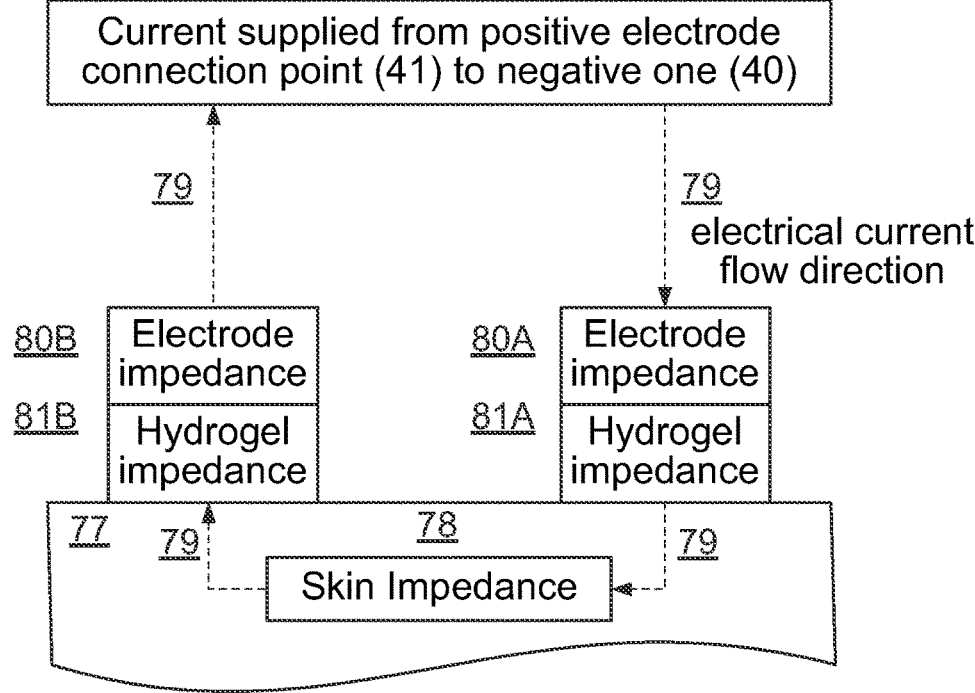
FIG. 6A depicts the skin impedance and the electrical impedance of the neuromodulation device.
Figure 6B:
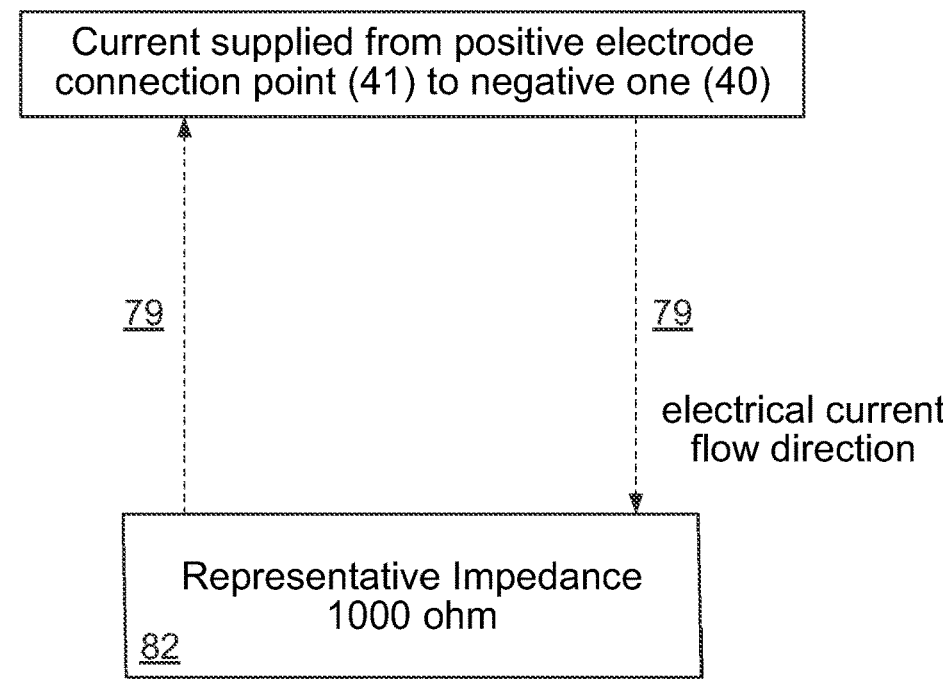
FIG. 6B depicts the current pulse measurement of the neuromodulation device.

Now referring to FIGS. 6A and 6B, FIG. 6A depicts the electrical impedance due to connections of the neuromodu-lation device 1 and FIG. 6B depicts the current pulse measurement of the neuromodulation device 1. The patient's skin 77 is the surface to which the current source 60 of the neuromodulation device 1 can transmit the electrical pulses of the treatment current 79 illustrated in FIG. 5. FIG. 6A shows the impedances encountered by the treatment current 79 that will flow between the electrodes 40 and 41 of the positive and negative electrodes when the neurostimulation device 1 is connected to the patient's skin 77. The constant current source 60 can provide a treatment current 79 accord-ing to the impedance connected between the positive and negative electrode electrodes 40 and 41. Equation 1 depicts how the total impedance can include the impedance of the electrodes (80A, 80B), the impedance of the hydrogels (81A, 81B), and the impedance of the body 78.

$$Z_{equivalent} = Z_{hydrogels} + Z_{electrodes} + Z_{skin} \qquad \text{Equation 1}$$

FIG. 6B depicts the reference impedance 82 connection of the neuromodulation device 1, which can be used to measure maximum electrical current rating of the neuromodulation device 1. The reference impedance value 82 can be 1000 ohms. When defining the current rating of the neuromodu-lation device 1 that the neuromodulation device 1 can apply between two electrodes, a 1000-ohm actual load 82 is referenced, which represents the impedance of the body surface 77 where the electrodes 40 and 41 connected with hydrogels 46A, as shown in FIG. 6B. For example, the neuromodulation device 1 can apply mono phasic current pulses up to 60 mA (at 1000-ohm load reference 82) for neuromodulation. The amplitude of the current that can be applied from the positive treatment electrode 41 and negative treatment electrode 40 connection points can be inversely proportional to the voltage (U) applied to these points and the impedance value (Z) connected to these points as shown in equation 2:

$$I[\text{mA}] = \frac{U_{between\ 40\ \&\ 41}}{Zref} \qquad \text{Equation 2}$$

As shown by equation 2, the maximum current rating of the neuromodulation device 1 can be directly proportional to the maximum output voltage of the DC/DC step-up converter 66. The maximum voltage that the DC/DC step-up convertor 66 can provide between the connection points of the positive treatment electrode 41 and negative treatment electrode 40 of the constant current source 60 is 60 V. According to Equation 2, the maximum current is 60 mA:

$$I\ \text{max} = \frac{60\ V}{1000\ \text{ohm}} = 60\ \text{mA}$$

The neuromodulation device 1 can include a step-up converter 66, such as an adjustable DC/DC step-up converter 66, which can be a voltage boost converter that feeds the constant current source 60. The step-up convertor can increase the voltage it receives from the battery. For example, the step-up convertor can increase the voltage up to 60V. In another example, the DC/DC step-up converter 66 increases the 6V DC voltage 68 it receives from the battery 47 to between a minimum 25V DC voltage and maximum 60V DC voltage. The output voltage of the step-up converter 66 can be the input of the constant current source 60.

Figure 7:
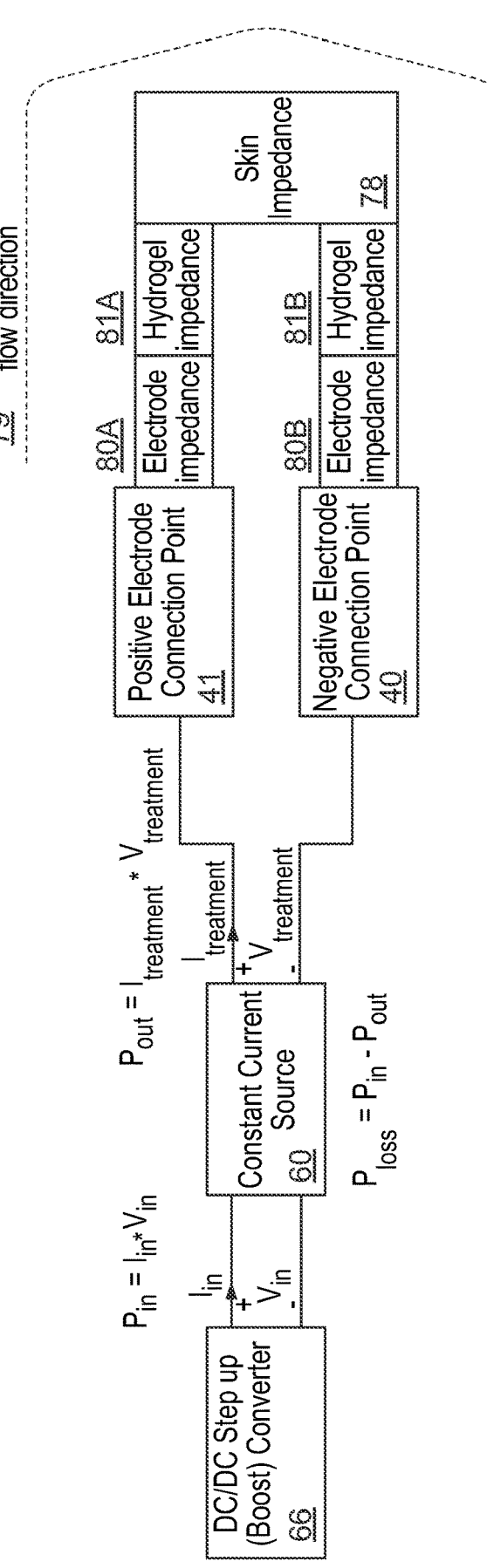
FIG. 7 depicts a DC/DC step up converter and constant current source work for regulation of output voltage for the neuromodulation device.

FIG. 7 depicts the DC/DC step-up converter 66 and constant current source 60 for regulation of output voltage for the neuromodulation device 1. The output voltage of the DC/DC step-up converter 66 can be automatically increased or decreased according to the impedance of the surface and human body the neuromodulation device 1 is adhered as well as the treatment current need. For instance, if the impedance encountered in the skin contact area is low, the voltage source of the stimulation current lowers the output voltage of the DC/DC step-up converter 66 to keep the current constant. The decrease in the output voltage of the DC/DC step-up converter 66 also contributes to the increase in the life cycle of the battery. This feature allows more efficient battery use. Changing the voltage can allow for more efficient battery use compared to simply providing constant current and at maximum the output voltage. The voltage modulation also enables the size of the neuromodulation device 1 to be reduced for adaptation as a comfortably wearable technology.

Referring to FIG. 4, the neuromodulation device 1 includes an auxiliary voltage regulator 69 that feeds the peripherals. The auxiliary voltage regulator 69 can be disabled by the controller 56 when the neuromodulation device 1 goes into sleep mode, during which the current drawn from the battery 47 decreases to extend standby life of the battery. For example, the current drawn can decrease from 14 uA and 40 uA to extend the standby life of the battery between 4 and 5 months. The neuromodulation device 1 includes the main voltage regulator 70 that feeds the controller 56.

Figure 8:
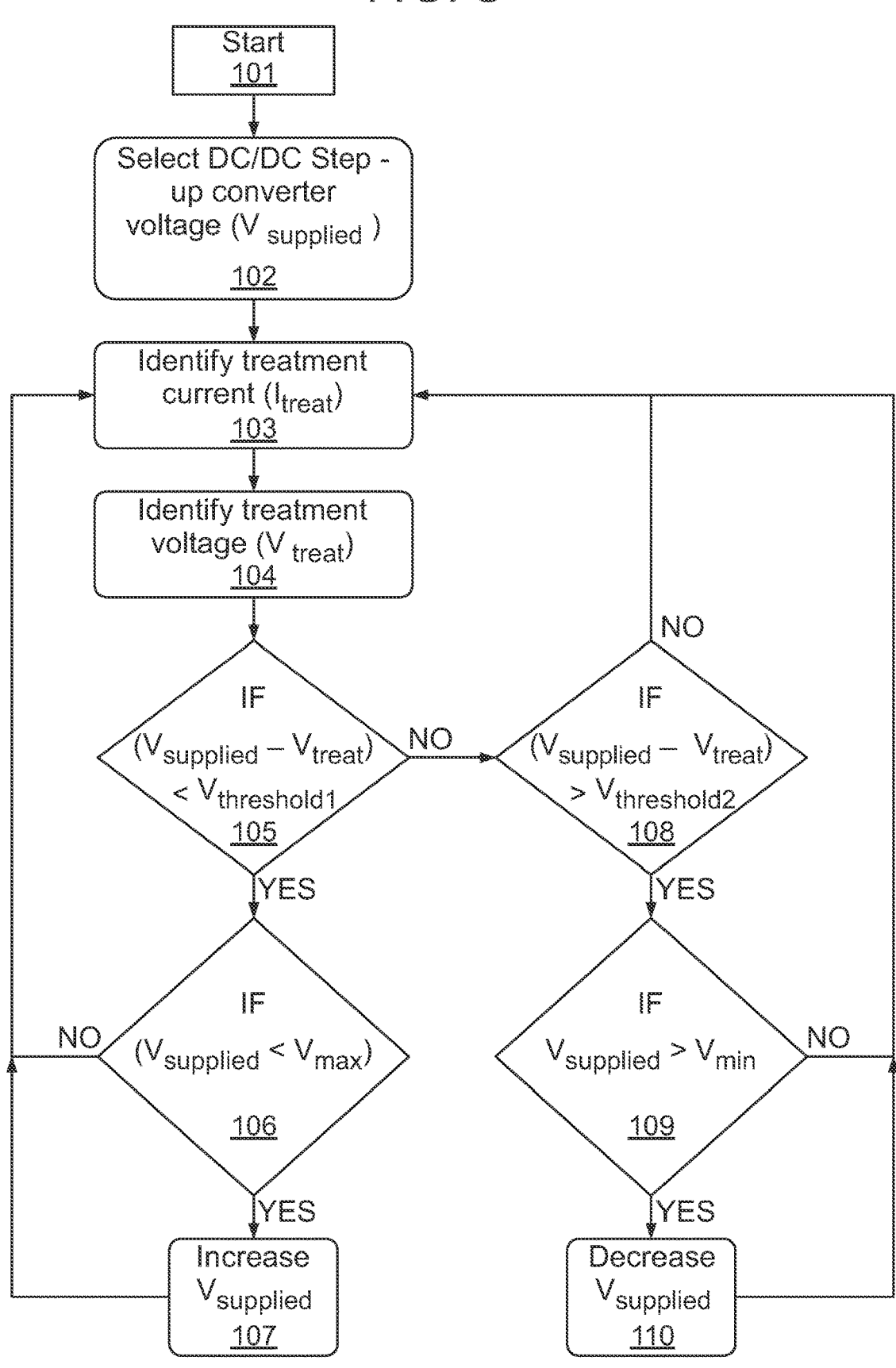
FIG. 8 is a flowchart for regulating output voltage of the DC/DC step up converter to regulate the output voltage of neuromodulation device.

FIG. 8 is a flowchart of a flow for regulating output voltage of the neuromodulation device 1. The neuromodulation device 1 powers on and begins regulating the output voltage (STEP 101). The neuromodulation device 1 causes the DC/DC step-up converter 66 to output a supply voltage ($V_{supplied}$) (STEP 102). For example, the supplied voltage can be set to a minimum (Venin) of 15 V. The output voltage of the DC/DC step-up converter 66 can be increased from the minimum level according to the voltage requirement as the treatment current is increased, and vice versa. The neuromodulation device 1 identifies the treatment current of ($I_{treat}$) (STEP 103). In some embodiments, the neuromodulation device 1 identifies the treatment current to the treatment current selected by the patient 6 via the mobile application 2.

The neuromodulation device 1 can identify the treatment voltage ($V_{treat}$) for providing the treatment current to the patient 6 (STEP 104). The neuromodulation device 1 can identify the treatment voltage by multiplying the treatment current by the impedance (e.g., V=I*R). The neuromodulation device 1 can identify the impedance (according to equation 2) of the electrode impedance 80A and 80B, hydrogel 81A and 81B, and skin impedance 78 connected between the electrodes 40 and 41. In some embodiments, the equivalent average impedance value and treatment current can be defined by selections received from the patient 6 via the mobile application 2. In some embodiments, the neuromodulation device 1 or the mobile application 2 calculates the equivalent average impedance value. For example, if the patient set the treatment current value to 15 mA and the value corresponding to the equivalent impedance (equation 2) is 2000 ohms. The voltage value to be created between the positive electrode terminal 41 and the negative electrode 40 terminal through a constant current source 60, according to equation 2, would be 30V.

The neuromodulation device 1 can select the supplied voltage to minimize power loss and maximize efficient use of the battery 47 while providing the selected treatment current to the patient (STEPS 105-110). The regulation of the supply voltage reduces consumption can reduce power consumption and improve energy efficiency. For example, if the supply voltage of the DC/DC step-up converter 66, and thus the supplied voltage to the input of the constant current source 60, remained constant at 60V while the treatment voltage was 30V, there would be power loss, which means additional consumption from the battery 47. The power loss is calculated in equation 3:

$$P_{loss} = P_{supplied} - P_{treatment}$$

$$P_{loss} = (I_{supplied} * V_{supplied}) - (I_{treatment} * V_{treatment})$$

$$P_{loss} = (15\ \text{mA} * 60\ V) - (15\ \text{mA} * 30\ V)$$

$$P_{loss} = 450\ \text{mW} \qquad \text{Equation 3:}$$

The closer the supplied voltage of the DC/DC step-up converter 66 is to the treatment voltage between the positive treatment electrode 41 and the negative treatment electrode 40 of the constant current source 60, the smaller the power loss while providing the treatment current, which enables efficient use of the battery 47.

The neuromodulation device 1 can subtract the treatment voltage from the supplied voltage (STEP 105). If the result is less than a lower voltage threshold ($V_{threshold1}$), then the flow can proceed to STEP 106. For example, if the supplied voltage is 45V and the treatment voltage is 50V, then the result of −5V is less than a lower voltage threshold of −1V and the supplied voltage can be increased to provide the desired treatment current to the patient 6. If the result is not less than the lower voltage threshold, then the flow can proceed to STEP 108. For example, if the supplied voltage is 55V and the treatment voltage is 50V, then the result of 5V is not less than the lower voltage threshold of −1V and the supplied voltage can be decreased to minimize power loss while providing the selected treatment current to the patient 6.

The neuromodulation device 1 can compare the supplied voltage to the maximum voltage ($V_{max}$) that can be output by the DC/DC step-up converter 66 (STEP 106). For example, the neuromodulation device 1 and the DC/DC step-up converter 66 might be able to output a max voltage of 60V (e.g., maximum safe voltage for neuromodulation). If the supplied voltage is already at the max voltage, then the flow proceeds to STEP 103 because the supplied voltage cannot be further increased. For example, if the supplied voltage is 60V and the max voltage is 60V, then the supplied voltage is at the max value and cannot be increased. If the supplied voltage is less than the max voltage, then the flow can proceed to STEP 107 because the supplied voltage can be increased. For example, if the supplied voltage is 45V and the max voltage is 60V, then the supplied voltage can be increased to provide the selected treatment current to the patient 6.

The neuromodulation device 1 can cause the DC/DC step-up converter 66 to increase the supply voltage (STEP 107). For example, if the supplied voltage is 45V and the treatment voltage is 50V, then the neuromodulation device 1 can cause the DC/DC step-up converter 66 to increase the supply voltage to 50V to provide the desired treatment current to the patient 6. The flow can proceed to STEP 103 to re-identify the treatment current and treatment voltage.

The neuromodulation device 1 can subtract the treatment voltage from the supplied voltage (STEP 108). If the result is greater than an upper voltage threshold ($V_{threshold2}$), then the flow can proceed to STEP 109. For example, if the supplied voltage is 55V and the treatment voltage is 50V, then the result of 5V is greater than the upper voltage threshold of 1V and the supplied voltage can be decreased to minimize power loss. If the result is not greater than the upper voltage threshold, then the flow can proceed to STEP 103. For example, if the supplied voltage is 50V and the treatment voltage is 50V, then the result of 0V is not less than the upper voltage threshold of −1V (STEP 105) and not greater than the upper voltage threshold of 1V, so the supplied voltage can remain unchanged while providing the desired treatment current to the patient 6.

The neuromodulation device 1 can compare the supplied voltage to the minimum voltage ($V_{min}$) that can be output by the DC/DC step-up converter 66 (STEP 109). For example, the neuromodulation device 1 and the DC/DC step-up converter 66 might be able to output a minimum voltage of 15V (e.g., minimum voltage that can be output because of inherent impedance). If the supplied voltage is already at the minimum voltage, then the flow proceeds to STEP 103 because the supplied voltage cannot be further decreased. For example, if the supplied voltage is 15V and the minimum voltage is 15V, then the supplied voltage is at the minimum value and cannot be decreased. If the supplied voltage is greater than the minimum voltage, then the flow can proceed to STEP 110 because the supplied voltage can be decreased. For example, if the supplied voltage is 45V and the minimum voltage is 15V, then the supplied voltage can be decreased to minimize power loss while providing the selected treatment current to the patient 6.

The neuromodulation device 1 can cause the DC/DC step-up converter 66 to decrease the supply voltage (STEP 110). For example, if the supplied voltage is 50V and the treatment voltage is 45V, then the neuromodulation device 1 can cause the DC/DC step-up converter 66 to decrease the supply voltage to 45V to minimize power loss while providing the selected treatment current to the patient 6. The flow can proceed to STEP 103 to re-identify the treatment current and treatment voltage.

The neuromodulation device 1 can include an accelerometer 71. The neuromodulation device 1 can use the accelerometer to measure the patient's mobility and activity level. The controller 56 can use the accelerometer 71 to measure the patient's level of activity during the treatment. In another example, the controller 56 can use of the accelerometer 71 is to detect a possible fall or impact in elderly individuals and use this data as an emergency notification. Another use is to enable certain functions (waking up from sleep mode and switching the neuromodulation device 1 to sleep mode by turning it on or off, etc.) by clicking on the top surface of the neuromodulation device 1.

The neuromodulation device 1 includes a buzzer 73, which can generate audible warnings. In some embodiments, the neuromodulation device 1 can receive a signal from the mobile application 2 to turn the buzzer 73 on and off. The mobile application 2 can receive the signal from the web service 3. The signal can specify a pattern (e.g., buzz every 3 seconds) for the buzzer 73. The buzzer 73 provides feedback while providing the basic functions of the neuromodulation device 11.

During treatment, the light indicator 39 provides visual feedback and the buzzer 73 provides auditory feedback for indicating to the patient that the treatment is being delivered. The audible feedback of the buzzer 73 is enhanced by visual feedback (e.g., green and red) of the light indicator 39. For example, the neuromodulation device 1 is awakened from sleep mode by pressing down the button 38 on it for a minimum of 3 seconds, and the buzzer 73 signals together with the green LED to inform the patient that the neuromodulation device 1 is turned on. Similarly, in an emergency or when the patient 6 wants to turn off the neuromodulation device 1, as the button 38 on it is pressed down for a minimum of 3 seconds, the light indicator 39 and the buzzer 73 will indicate that the neuromodulation device 1 has entered sleep mode. In addition, the buzzer keeps beeping every 10 seconds to indicate that the patient is getting their treatment.

This audible and visual feedback during the treatment can trigger a placebo effect in addition to the actual effect of the treatment to enhance the treatment outcome by working synergistically with the actual treatment effect. The placebo effect can cause the patient to increase adherence to treatment (as an addition to the actual treatment's effect) to enhance the treatment outcome by working synergistically with the actual treatment effect since OAB responds well to such placebo effect. The systems described herein can actively bring together features known to enhance adherence to treatment (such as patient navigation) and augment treatment success/clinical outcome. These features can be applied consistently, all in the same context, with consecutive repetition (such as the urinary diary at the beginning, middle and end of treatment—is not used only as an assessment tool, but as a treatment tool as well). The systems described herein can advantageously include self-navigation features and behavioral therapy tools in the treatment system.

The neuromodulation device 1 can include a memory unit 74, which can be non-volatile memory (e.g., EEPROM) or volatile memory. The memory unit 74 records the treatment activities such as the error states of the neuromodulation device 1, the number of sessions performed, the impedance and voltage changes experienced during the treatment, and the patient's mobility level. Logs of critical information (potential error codes) about the treatment and the neuromodulation device 1 can be kept in the memory of the neuromodulation device 1. The memory can store a unique identifier of the neuromodulation device 1.

The neuromodulation device 1 can include a communications unit 75. In some embodiments, the communication circuit is a Bluetooth circuit. In some embodiments, different communication circuits can be used. The neuromodulation device 1 can use the communications circuit to exchange treatment activities by communicating with the mobile application 2. The communications circuit can be a Bluetooth circuit that can establish or maintain a Bluetooth connection to the mobile device via the Bluetooth protocol. This unit can be a communication circuit such as Bluetooth, wireless. Indoor positioning is calculated based on TX power in accordance with beacon technology.

The communication unit 75 allows the neuromodulation device 1 to be used as an indoor positioning device and/or data exchange with a mobile application 2. The microcontroller can extract the voltage and current parameters from the treatment protocol information received via the communication unit 75 from the mobile application 2. The microcontroller can generate a signal for the constant current source based on the voltage and current parameters. The microcontroller can transmit the signal to the constant current source to apply the treatment current to the patient.

During the treatment, even if the connection between the neuromodulation device 1 and the mobile application 2 is lost (e.g., the phone's battery runs out, etc.), the neuromodulation device 1 continues to deliver the treatment. Upon reconnecting with the neuromodulation device 1, the previously completed treatment activities saved in a non-volatile memory unit (e.g., EEPROM) or a volatile memory unit (e.g., RAM) can be transferred to the mobile application 2.

The neuromodulation device 1 includes a charge controller 76. If a rechargeable battery is used, the charge controller 76 can provide the charge to the battery. The voltage of the battery can be a nominal 6V.

Section B: Mobile Application

Figure 9:
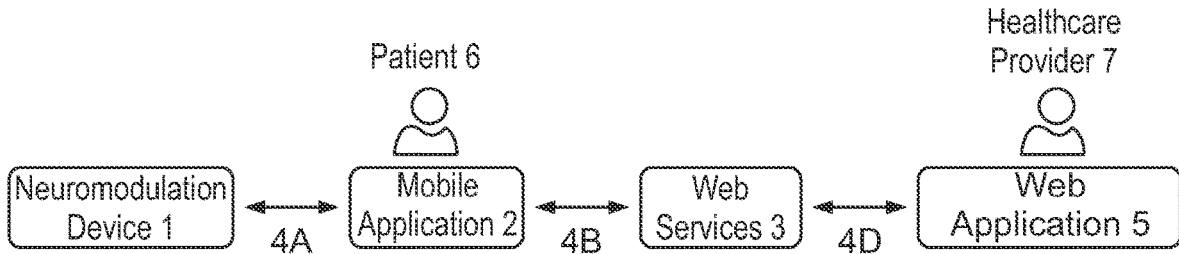
FIG. 9 is a block diagram depicting a data driven system solution that comprises the neuromodulation device, mobile application, and web service, web application, patient, and healthcare professional.

FIG. 9 is a block diagram depicting a data driven system that comprises the neuromodulation device 1, mobile application 2, and web service 3, web application 5, patient 6, and healthcare provider 7. The data driven system can receive and incorporate feedback to improve adherence info based on the location of the patient 6, a urinary diary, validated questionnaires (as neuromodulation device 1 is used for different indications validated questionnaires of those indications can be added), and info from calendar that shows actual adherence of the patient 6 to their assigned treatment calendar.

The mobile application 2 can monitor the patient 6 by managing the neuromodulation device 1 and receiving treatment activities from the patient 6. The mobile application 2 can transmit the treatment activities to the web service 3. The mobile application 2 can be executed by a mobile device, such as a phone or tablet that belongs to the patient 6. The web service 3 manages the information exchanged with the mobile application 2 and displayed via the web application 5. The web service 3 can communicate with the web application 5 via a connection 4D, such as the internet. The web application 5 is an interface that manages the registration of the neuromodulation device 1 and the patient 6 for the remote treatment. The patient 6 uses the neuromodulation device 1 and mobile application 2 for treatment. The healthcare provider 7 can be a doctor, nurse, or any other medical provider who assigns and controls the treatment.

The neuromodulation device 1 and the mobile application 2 can maintain a connection for registration of the patient 6 and monitoring of the treatment by the patient 6 and the healthcare provider 7. The web service 3 receives data from the mobile application 2 about whether the patient 6 applied the treatment and the status of the treatment. The mobile application 2 can be in communication with the web service 3 administered by the healthcare provider 7. The mobile application 2 can be in communication with the web service 3 to receive treatment protocol information provided by the healthcare provider 7 via the web application 5. The healthcare provider 7 can use a web application 5 that manages the registration of the patient 6 and the neuromodulation device 1 with the web service 3 to manage the information input and displayed via the web application 5. The connections enable the remote monitoring of the delivery of the treatment at adequate treatment values and ensures the effectiveness of the treatment.

The patient 6 can adhere the neuromodulation device 1 to a location on their body and apply the treatment protocol configured by a healthcare provider 7 but without their presence. The transcutaneous posterior tibial nerve stimulation device 1 can be remotely monitored by the healthcare provider 7 to monitor the course of treatment in the treatment of urinary incontinence, fecal incontinence, and pelvic pain. The mobile application 2 can receive the treatment activity from the neuromodulation device 1 and transmit the treatment activity to the web service 3. The web service 3 saves this information and transmits the information to the web application 5 for presentation to the healthcare provider 7. The healthcare provider 7 can access via the web application 5 to make evaluations about the treatment based on this data.

Figure 10:
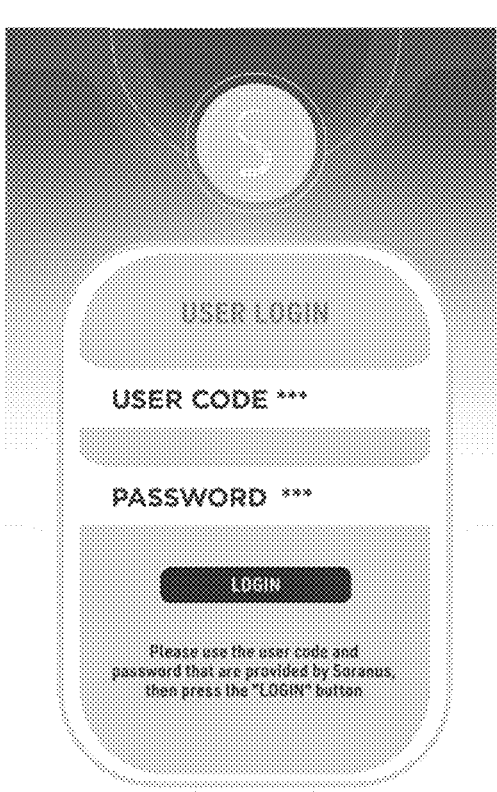
FIG. 10 depicts an interface for the patient to access the system.

FIG. 10 depicts an interface displayed by the mobile application 2 for the patient 6 to access the mobile application 2 to begin the first treatment and subsequent treatments. The mobile application 2 can display a login screen for the patient 6. In some embodiments, the mobile application 2 can receive, from the patient 6 via the login screen, the identifier number and the password assigned to the patient via the login screen will be displayed by the mobile application 2. For example, when the mobile application 2 receives the patient identifier and password from the patient 6 via the login screen. After validating the patient identifier and password, the mobile application 2 can grant the patient 6 permission to begin treatment steps.

Figure 11A:
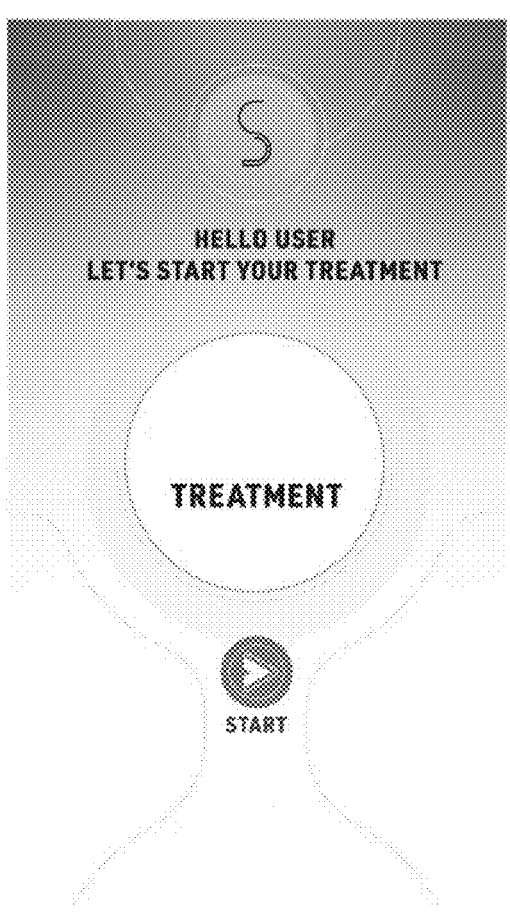
FIGS. 11A-11G depict interfaces displayed by the mobile application for initializing treatment.

FIGS. 11A-11G depict interfaces displayed by the mobile application 2 for initializing treatment. FIG. 11A shows an interface for starting treatment. When the mobile application 2 detects a selection of the "Start" button, the mobile application 2 can display instructions for placement of the neuromodulation device 1.

Figure 11B:
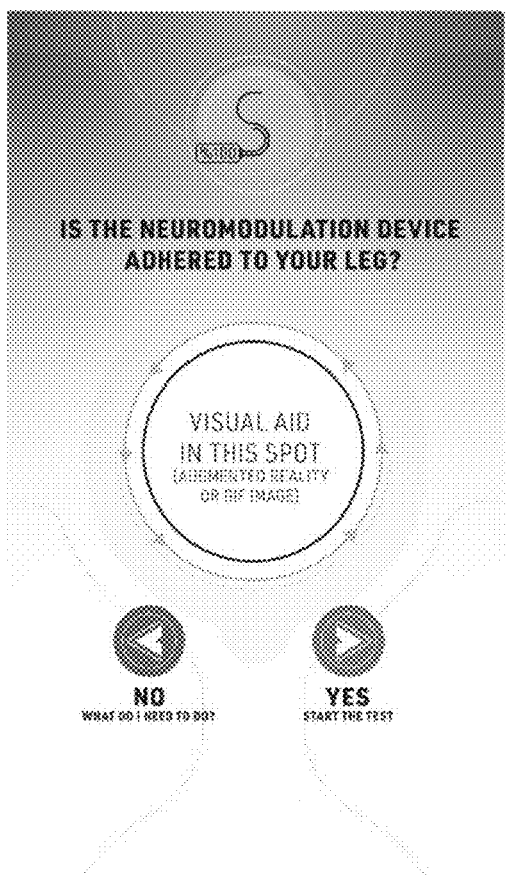
Figure 11C:
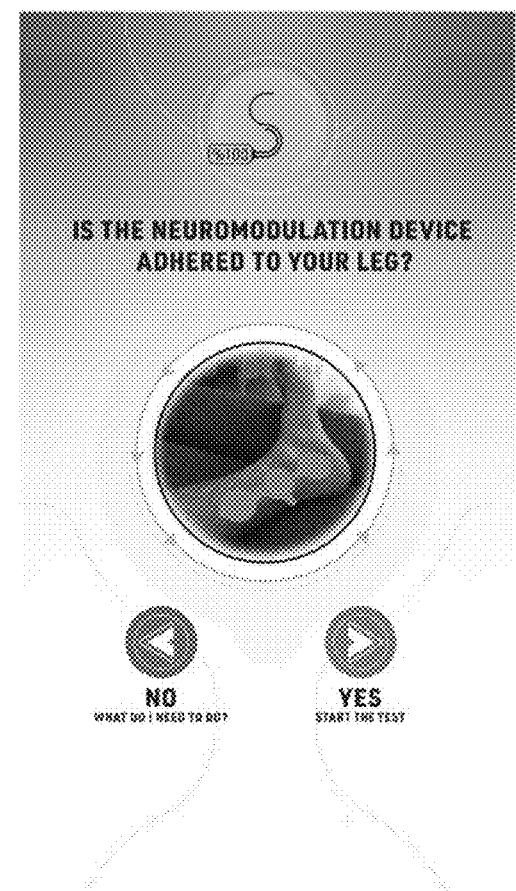

FIG. 11B and FIG. 11C show the interface displayed by the mobile application 2 to describe the location where the neuromodulation device 1 will be placed on the leg. The mobile application 2 can provide augmented reality, video, or animations to help the patient 6 to position the neuromodulation device 1 at the correct location on their leg. The mobile application 2 can generate a visual animation, video, or augmented reality for the patient 6 to verify the proper adherence of the neuromodulation device 1.

As shown in FIG. 11B, augmented reality, video, or animations can be displayed in the area marked "VISUAL AID IN THIS SPOT". In some embodiments, the mobile application 2 can generate virtual marks to indicate the exact anatomical location where the electrodes must be adhered. In some embodiments, to provide augmented reality, the mobile application 2 can cause the camera of the mobile device to turn on. When the mobile application 2 detects the patient's leg in the images generated by the camera, the mobile application 2 can generate a virtual image of the neuromodulation device 1 as it can be worn on the patient's leg in the same area marked "VISUAL AID IN THIS SPOT." The augmented reality engine will run in the background of the mobile application 2.

As shown in FIG. 11C, the mobile application 2 can show the leg and how the neuromodulation device 1 is to be adhered to the leg. Thus, the patient 6 will instantly see how to connect the neuromodulation device 1 on their leg. The mobile application 2 can detect a confirmation (e.g., selection of 'YES') from the patient 6 that the neuromodulation device 1 is positioned.

Figure 11D:
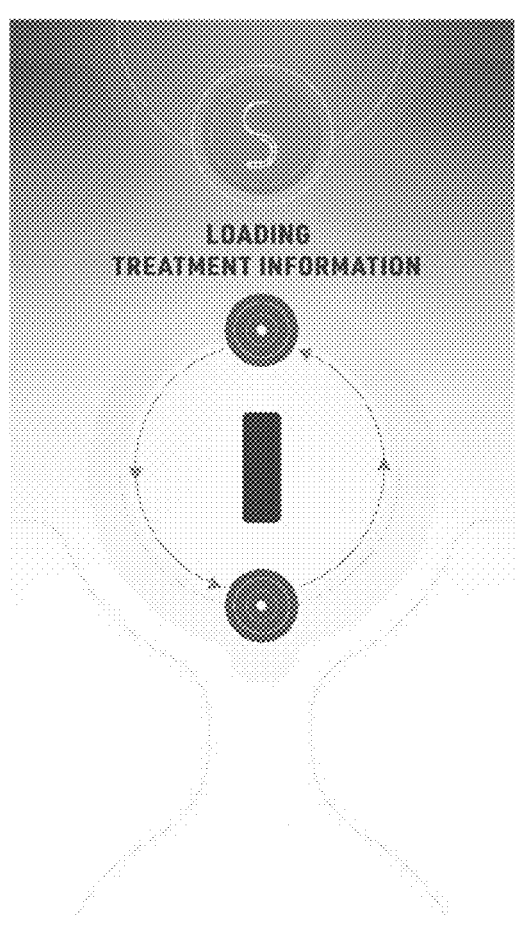

As shown in FIG. 11D, the mobile application 2 can retrieve, from the web service 3 via a connection (e.g., 4B), the treatment protocol assigned in the web service 3 by the healthcare provider 7. The mobile application 2 can start searching for the neuromodulation device 1 via the communication unit 75 such as the Bluetooth circuit.

The mobile application 2 can establish communications with the neuromodulation device 1 responsive to verifying the device identifier of the neuromodulation device 1. For example, when the patient 6 acquires their neuromodulation device 1, the healthcare professional 7 can use the web application 5 to cause the web service to register the device identifier of the neuromodulation device 1 with the patient identifier of the patient 6. When the patient 6 goes home and wants to start their treatment, they can login via the mobile application 2 with their patient identifier. The mobile application 2 can receive, from the web service 3, the device identifier of the neuromodulation device 1 registered for the provided patient identifier and compare it with the device identifier of the neuromodulation device 1 attempting to connect to the mobile application 2. If the mobile application 2 identifiers a match, then the mobile application 2 can establish the communication to begin treatment.

A device identifier of the neuromodulation device 1 can be assigned to the patient 6 by the healthcare provider 7 accessing the web service 3 via the web application 5. The mobile application 2 can receive the assigned device identifier of the neuromodulation device 1 that is assigned from the web service 3. When the neuromodulation device 1 and the mobile application 2 attempt to establish the connection (e.g., Bluetooth), the mobile application 2 can receive a candidate device identifier of the neuromodulation device 1. The mobile application 2 can compare the candidate device identifier of the candidate neuromodulation device 1 attempting to connect to the assigned device identifier of the neuromodulation device 1 that was assigned to the patient 6 by the healthcare provider 7. If the device identifiers match (e.g., the connecting device is the assigned device), then the mobile application 2 can establish the communications and transmit treatment protocol information to the neuromodulation device 1 via the connection (e.g., Bluetooth) between the mobile application 2 and the neuromodulation device 1. The neuromodulation device 1 can receive the treatment protocol information. In some embodiments, if the patient 6 does not start the test stage or the mobile application 2 fails to connect with the neuromodulation device 1 within 5 minutes after the neuromodulation device 1 is turned on, the neuromodulation device 1 turns itself off.

The mobile application 2 can cause a camera of the mobile device to capture a QR code to establish communications with the neuromodulation device 1. In some embodiments, the QR code is disposed on the neuromodulation device 1. In some embodiments, the mobile application 2 receives the candidate device identifier from the patient 6. For example, the patient 6 can type in the candidate device identifier that they see on the neuromodulation device 1. The mobile application 2 can transmit the captured QR code or candidate device identifier to the web service 3 for authentication. Responsive to the mobile application 2 receiving a response from the web service 3 verifying the QR code or candidate device identifier, the mobile application 2 can establish communications with the neuromodulation device 1.

Figure 11E:
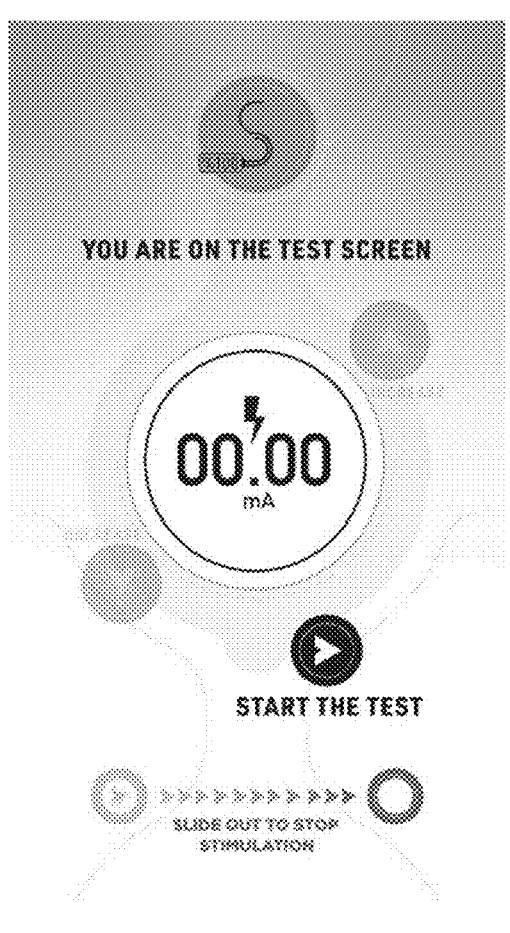

The mobile application 2 can display the "Test Screen" shown in FIG. 11E if the mobile application 2 connects via the communication unit 75 (e.g., Bluetooth) to the neuromodulation device 1 that is online. The mobile application 2 can display the "Test Screen" to prompt the patient 6 to adjust the treatment current. The patient 6 can adjust the treatment current before each treatment session, according to their motor and/or sensory response.

The mobile application 2 can display instructions for the patient 6 to increase the current level until they get a motor (e.g., their toe moves) and/or sensory response (e.g., feel tickling sensation). Some healthcare professionals 7 might instruct patients 6 to keep increasing the current level until tolerable but past motor and/or sensory response level. Even if the patient increases the treatment current to a non-tolerable level, the patient 6 can use the mobile application 2 to decrease the treatment current.

The mobile application 2 can receive inputs to increase current at an intensity tolerable to the patient 6. The mobile application 2 can receive selections of treatment current from the patient 6 to produce a motor and/or sensory response. For example, the electric current value can be set to the value that produced a motor response, and the increase in current can be stopped at an intensity tolerable to the patient 6. The patient 6 can do this without the assistance of the healthcare provider 7 and outside of hospital setting. For example, the patient 6 can apply the treatment at home, at work, or on the go.

Figure 11F:
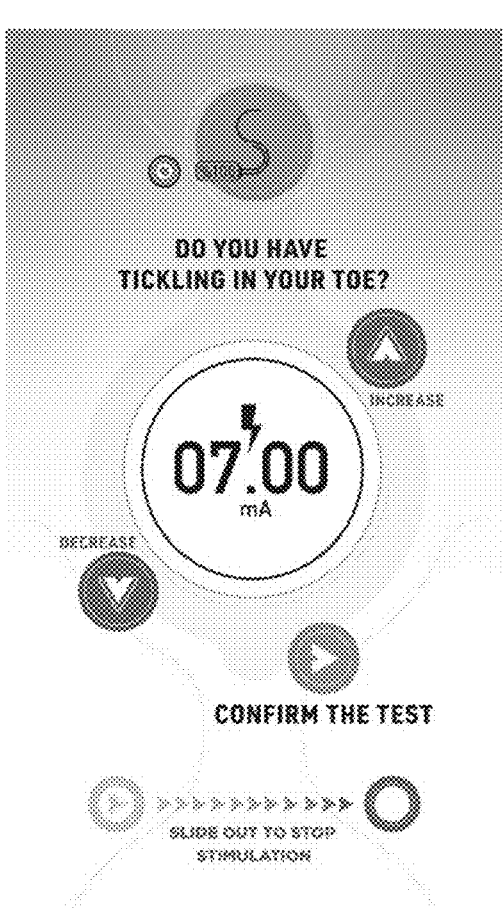

As shown in FIG. 11F, if the mobile application 2 detects that the patient 6 presses the "start test" button on the "Test Screen", the mobile application 2 can display the adjustment screen to prompt the patient 6 to increase or decrease the treatment current. The mobile application 2 can transmit a command to the neuromodulation device 1 to prepare to apply test treatment current. In some embodiments, the test treatment current starts at 0 mA. The mobile application 2 can detect adjustments to the treatment current by detecting presses of the "INCREASE" button to increase the treatment current or "DECREASE" button to decrease the treatment current. For example, the mobile application 2 can change the treatment current in intervals of 0.5 mA for every press of the button.

The mobile application 2 can detect that the patient 6 presses the "Confirm the Test" to indicate that they feel comfortable (provided that the sensory response continues) at that treatment current. The mobile application 2 can display confirmation messages on the "Test Screen" for the convenience of the patient 6. The confirmation messages can ask the patient to confirm the selected treatment current. In some embodiments, once the patient confirms the treatment current, the neuromodulation device stops applying current.

In some embodiments, if the connection is lost while displaying the interfaces in FIGS. 11E and 11F, the neuromodulation device 1 is configured to stop electrical stimulation to make sure the patient 6 does not receive any electrical current prior to setting the treatment current. Preventing electrical current is an advantageous feature because if the connection disconnects before the patient 6 could set the treatment current, then the neuromodulation device 1 would continue providing the set treatment current despite the disconnection. When the connection is restored, the mobile application 2 can display the interfaces of FIGS. 11E and 11F.

The mobile application 2 can optimize the treatment current based on the sensory threshold level at which the patient 6 reacts to the treatment. For example, the mobile application 2 can set the treatment current to 1.5 times the sensory threshold level. For example, for treatments performed by the transcutaneous route, the treatment application current varies between 10 mA and 20 mA on average and can be different at every session for the same patient 6.

The sensory threshold level of the patient 6 can change over time. Based on general observations in nerve stimulation, the excitation energy threshold of the nerve can increase during or after stimulation. Treatment sessions can be scheduled several days apart (e.g., every 2-3 days) to allow the threshold of the nerve to decrease again. To optimize the treatment current for each patient's unique sensory threshold level, the mobile application 2 can set the treatment current to be unique for each patient 6.

The neuromodulation device 1 can use the feedback electrodes 43 to measure the sensory threshold level energy. When the sensory threshold level energy of the nerve decreases to the level measured at the beginning of the previous treatment, the neuromodulation device 1 transmits a notification to the mobile application 2 for next treatment. The mobile application 2 can display a notification to the patient 6 to indicate that the patient 6 can administer their next treatment session as soon as possible. In this way, immediate treatment is possible without the need for standardized or predetermined waiting intervals between sessions, which can advantageously result in a shorter recovery time. On the other hand, this measurement can enable more frequent treatments that are more effective for patient 6 whose treatment interval (e.g., daily basis) is insufficient.

Figure 11G:
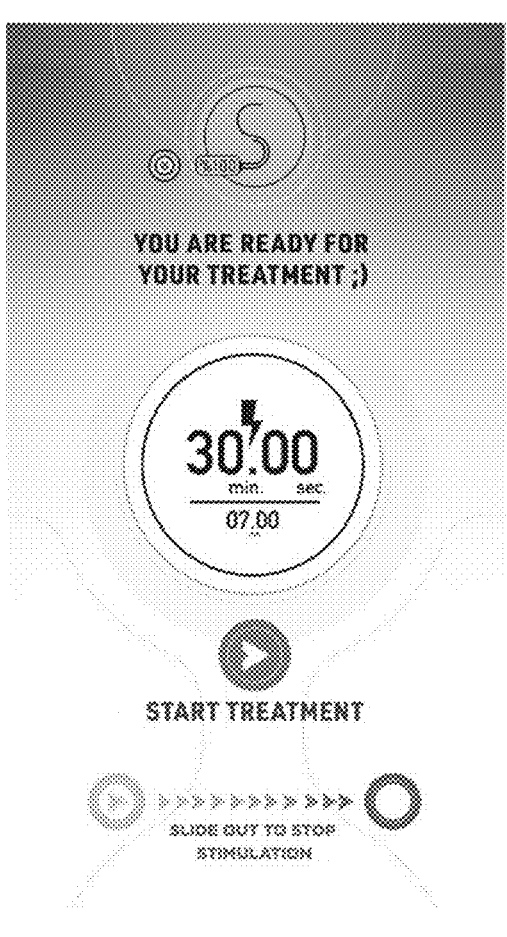

As shown in FIG. 11G, the mobile application 2 can display that the patient 6 is ready to start the treatment and asks the patient 6 to start treatment. In some embodiments, the mobile application 2 displays the treatment interface shown in FIG. 11G after detecting that the patient 6 selected to confirm the treatment current in the interface shown in FIG. 11F. automatically asking the patient to start treatment. Responsive to the mobile application 2 receiving a selection to start treatment, the mobile application 2 can transmit a command to the neuromodulation device 1 to apply the treatment current confirmed by the patient 6 at the test stage.

The mobile application 2 can display the "Start to Treatment" button, and the mobile application 2 can detect the patient 6 pressing the button to start the treatment. When the mobile application 2 detects the press of the "Start" button shown in FIG. 11G, the mobile application 2 can transmit a signal to the neuromodulation device 1 to begin transmitting the current to the location (e.g., leg) to be used (Right and/or Left) based on the treatment protocol information (Pulse Frequency, Pulse Width, Duration) from the treatment current selected on the test page shown in FIG. 11G. The mobile application 2 can cause the neuromodulation to start the treatment based on the prescribed protocol information from the treatment current selected on the "Test Screen". For example, the mobile application 2 can cause the neuromodulation device 1 to start treatment at the treatment current of 7 mA. When the treatment starts, the mobile application 2 can instruct the neuromodulation device 1 to administer the current with 0.5 mA/second increments until the treatment current set at test mode is reached.

Figure 12A:
FIGS. 12A-12E depict interfaces displayed by the mobile application for assessment.

FIGS. 12A-12E depict interfaces displayed by the mobile application 2 for assessment. In some embodiments, the results of these assessments are used for treatment monitoring purposes by the web service 3. FIG. 12A depicts an interface indicating that the neuromodulation device 2 is administering the treatment. The mobile application 2 can receive an acknowledgment from the neuromodulation device 1 that the treatment is being administered.

Figure 12B:

FIG. 12B depicts an interface indicating that the neuromodulation device 2 has completed administering the treatment. The mobile application 2 can receive an acknowledgment from the neuromodulation device 1 that the treatment is complete. As shown in FIG. 12B, the mobile application 2 can display a confirmation of completion of the treatment session while seeing the time from the counter (e.g., 10 seconds) on the screen. After the time expires, an uninterrupted treatment can ensure that the sufficient dose is taken. The neuromodulation device 1 can turn itself off 10 seconds after the completion of the treatment.

Figure 12C:
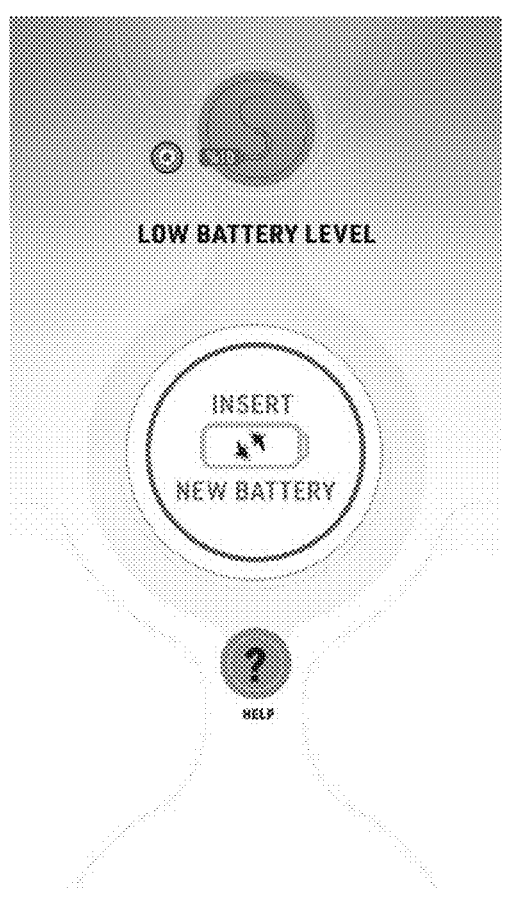

FIG. 12C depicts an interface indicating that the level of the battery 47 is low and that the patient 6 can insert a new battery. The mobile application 2 can receive a level of the battery 47 from the neuromodulation device 1. As shown in FIG. 12C, the mobile application 2 can display a warning screen to indicate that the battery level of the neuromodulation device 1 is low. To determine the battery level of the neuromodulation device 1, the mobile application 2 can transmit a request, to the neuromodulation device 1, for the battery level of the neuromodulation device 1. The mobile application 2 can receive the battery level from the neuromodulation device 1. If the battery level is low, the mobile application 2 can display a request for the patient 6 to replace (or charge) the battery. The mobile application 2 can display a help button. If the mobile application 2 detects that the patient 6 pressed the help button, then the mobile application 2 can display instructions to assist the patient 6 with changing the battery.

Figure 12D:
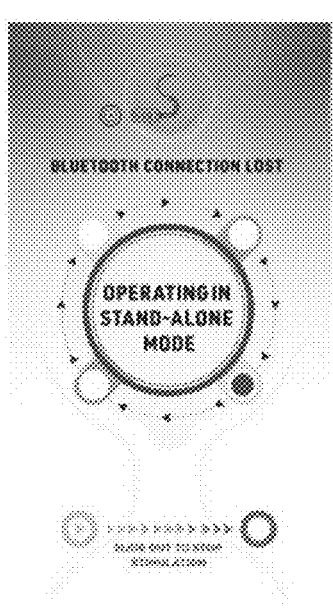

As shown in FIG. 12D, the mobile application 2 can display, during the treatment, even if the connection between the neuromodulation device 1 and the mobile application 2 is disconnected (closure of mobile application 2, the phone's battery runs out, etc.). The neuromodulation device 1 can continue delivering the treatment by operating stand-alone. If the treatment is still ongoing when the mobile application 2 reconnects with the neuromodulation device 1, mobile application 2 resumes. If the treatment has already been completed at the next connection, the mobile application 2 can receive the previously completed treatment activities from the memory unit 74 (e.g., EEPROM—non-volatile memory unit) of the neuromodulation device 1. The mobile application 2 can transmit the treatment activities to the web service 3.

Figure 12E:
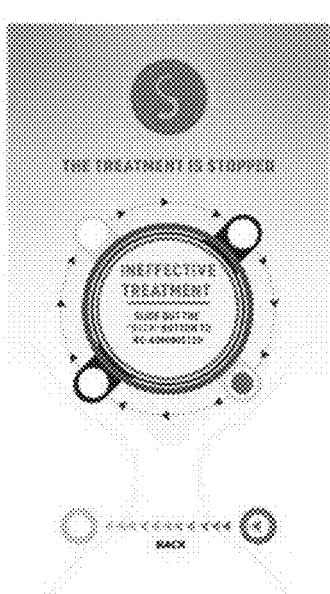

As shown in FIG. 12A, the mobile application 2 can display, during the treatment, a selectable option (e.g., slider or emergency stop slide-out button) to stop the treatment in an emergency. In some embodiments, the mobile application 2 can display a "Stop Test" button for the patient 6 to select when they feel comfortable (provided that the sensory response continues). The mobile application 2 can detect the selection of the selectable option (e.g., patient 6 slides the slider or presses the button) and transmit a request to the neuromodulation device 1 to stop the electrical stimulation. As shown in FIG. 12E, the mobile application 2 can display a confirmation screen indicating that the treatment was stopped. If the electrical stimulation cannot be stopped from the mobile application 2 (e.g., mobile application 2 disconnects from the neuromodulation device 1 as shown in FIG. 12D), the neuromodulation device 1 is configured to be turned off responsive to its button being pressed (e.g., for 3 seconds).

Figure 13A:
FIGS. 13A-13F depict interfaces displayed by the mobile application for navigating the patient for an effectively administered treatment.
Figure 13B:
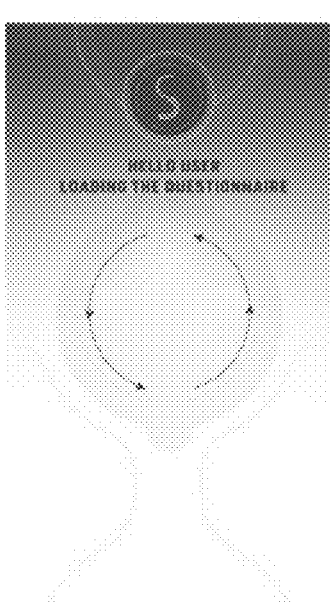
Figure 13C:
Figure 13D:
Figure 13E:
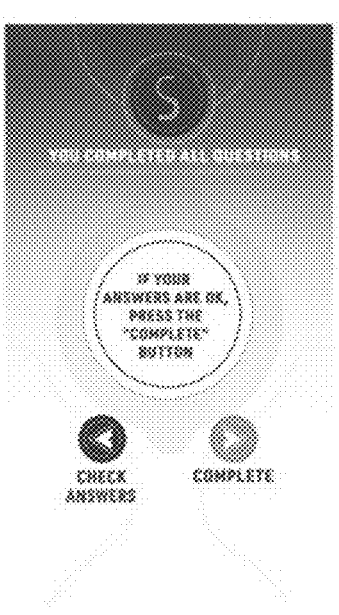
Figure 13F:
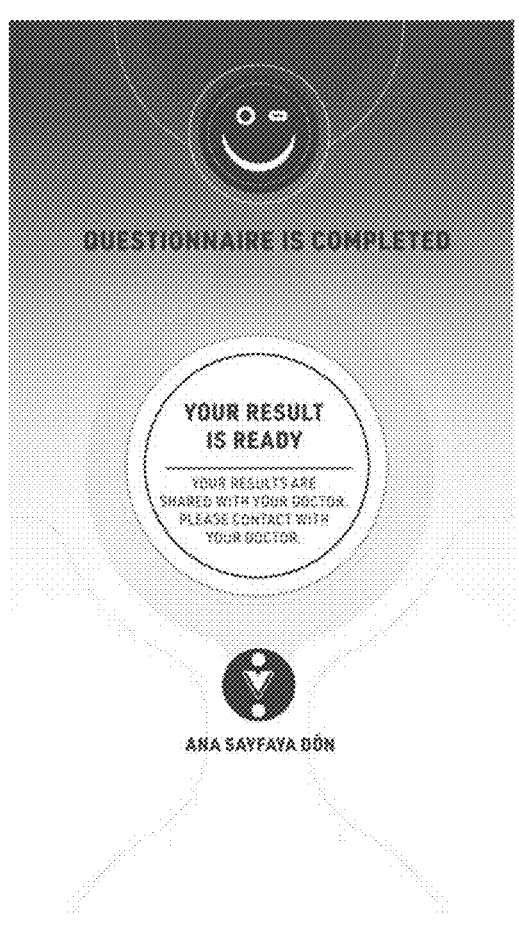

FIGS. 13A-13F depict interfaces displayed by the mobile application 2 for navigating the patient 6 for an effectively administered treatment. FIG. 13A depicts the mobile application 2 displaying a request for the patient 6 to provide responses to a questionnaire to assess the treatment. FIG. 13B depicts the mobile application 2 loading the questionnaire. In some embodiments, the mobile application 2 can retrieve and display the questionnaire responsive to detecting the patient 6 selecting to fill-out the questionnaire as shown in FIG. 13A. The mobile application 2 can receive the questionnaire from the web service 3. FIG. 13C depicts the mobile application 2 displaying a questionnaire about overactive bladder. Throughout the treatment (e.g., beginning, middle and end of the treatment), the mobile application 2 displays questionnaires for feedback on the treatment efficacy in the mobile application 2. FIG. 13D depicts the mobile application 2 displaying a question for the patient 6 to select how often they urinate. The questionnaires can include of questions for measuring the severity of overactive bladder disease. The mobile application 2 can detect selections by the patient 6. The mobile application can transmit the selections to the web service 3 for analysis. FIG. 13E depicts the mobile application 2 displaying a request for the patient 6 to confirm their answers. The mobile application 2 can detect a confirmation from the patient 6, after which the mobile application can transmit the selections to the web service 3 for analysis. FIG. 13F depicts the mobile application 2 displaying that the questionnaire is complete. After completing the questionnaires, the mobile application 2 can display reminder notifications for the patient 6 to remind them of treatment sessions according to the treatment schedule assigned by the healthcare provider 7. The mobile application 2 can receive the reminders from the web service 3.

FIGS. 14A-14G depict interfaces displayed by the mobile application for treatment assessment based on a urinary diary. In some embodiments, the results of these assessments are used for treatment monitoring purposes by the web service 3. The urinary diary is a diary used to list the conditions such as the frequency, amount of liquid consumption of the patient 6, urination times, need to urinate, and urinary incontinence. The urinary diary can be a validated assessment tool and can also be used as a treatment tool. It is up to the healthcare provider 7 accessing the web service 3 via the web application 5 to assess the advantages and disadvantages of treatment length (e.g., days) of use and decide how many days it can be used for their patients. The mobile application 2 can display a request for the patient 6 to provide information to a urinary diary to assess the treatment. The mobile application 2 can display the urinary diary or questionnaires at the beginning, middle and end of the treatment to monitor the treatment efficacy (e.g., monitor overactive bladder disease).

Figure 14A:
FIGS. 14A-14G depict interfaces displayed by the mobile application for assessment.
Figure 14B:
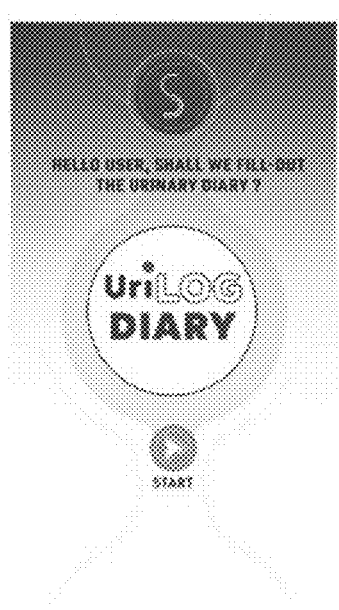

FIG. 14A depicts the mobile application 2 displaying a request for the patient 6 to fill out a urinary diary. FIG. 14B depicts the mobile application 2 displaying a type of urinary diary. In some embodiments, the mobile application 2 can retrieve and display the urinary diary responsive to detecting the patient 6 selecting to fill-out the urinary diary as shown in FIG. 14A. The mobile application 2 can receive the urinary diary from the web service 3. The web service can select a type of urinary diary based on the patient 6 using the mobile application 2.

Figure 14C:
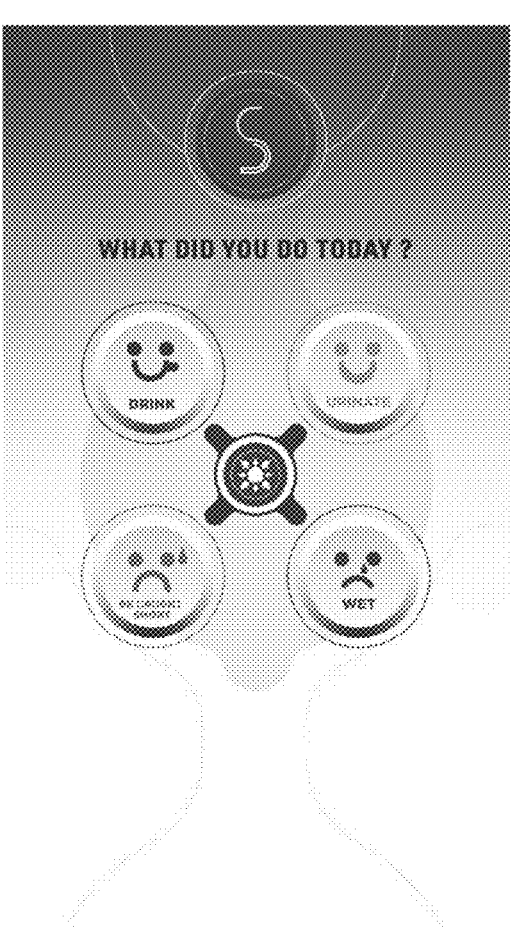
Figure 14D:
Figure 14E:
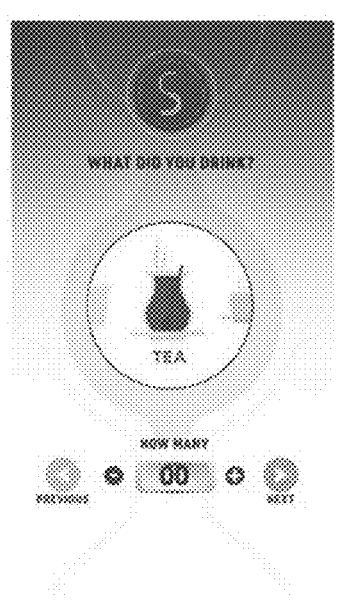
Figure 14F:
Figure 14G:
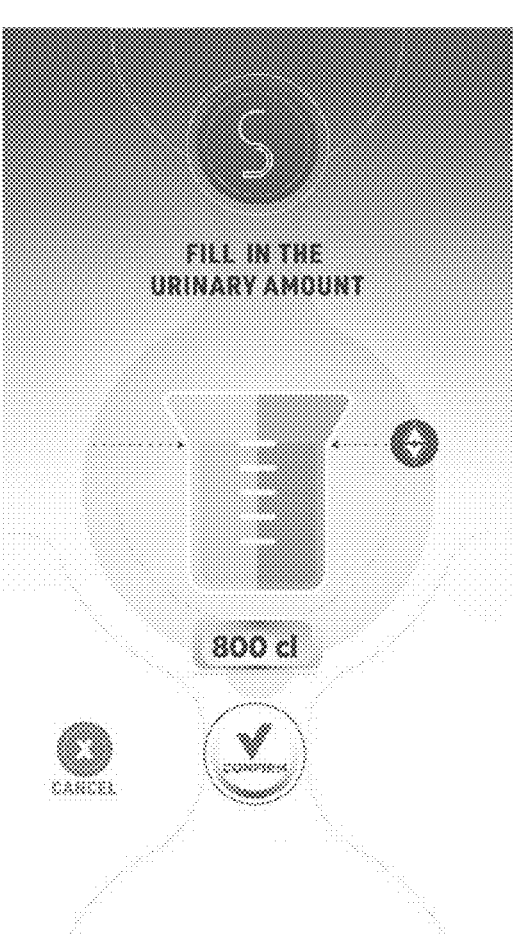

FIG. 14C depicts the mobile application 2 displaying a question for the patient 6 to assess their fluid intake and outtake. FIG. 14D depicts the mobile application 2 displaying a question for the patient 6 to select a type of fluid that they drank. FIG. 14F depicts the mobile application 2 displaying a question for the patient 6 to select a container type in which they drank the fluid. FIG. 14F depicts the mobile application 2 displaying a question for the patient 6 to select a quantity of the fluid that they drank. FIG. 14F depicts the mobile application 2 displaying a question for the patient 6 to select how much urine they excreted. The mobile application 2 can detect selections by the patient 6. The mobile application can transmit the selections to the web service 3 for analysis. After completing the questions for the urinary diary, the mobile application 2 can display reminder notifications for the patient 6 to remind them to continue filling out the urinary diary. The mobile application 2 can receive the reminders from the web service 3.

The use of validated questionnaires and urinary diaries in the mobile application 2 enables the healthcare provider 7 to monitor and analyze the effectiveness of the treatment remotely. The mobile application 2 can transmit treatment activities or feedback to the web service 3. The transmitted treatment activities can include the identifier of the neuromodulation device 1, Firmware Version, Mobile App Version, Result of Treatment Session, Completed Treatment Session Number, Date & Time of Start to Treatment, Error Code if it is available, Treatment Current, Treatment Duration even if interruption occurs, Average, Max. and Min. Impedance during the treatment, Average Treatment Voltage, Activity Level, Results of Urinary Diary, and validated questionnaires.

Section C: Positioning Devices

Figure 15:
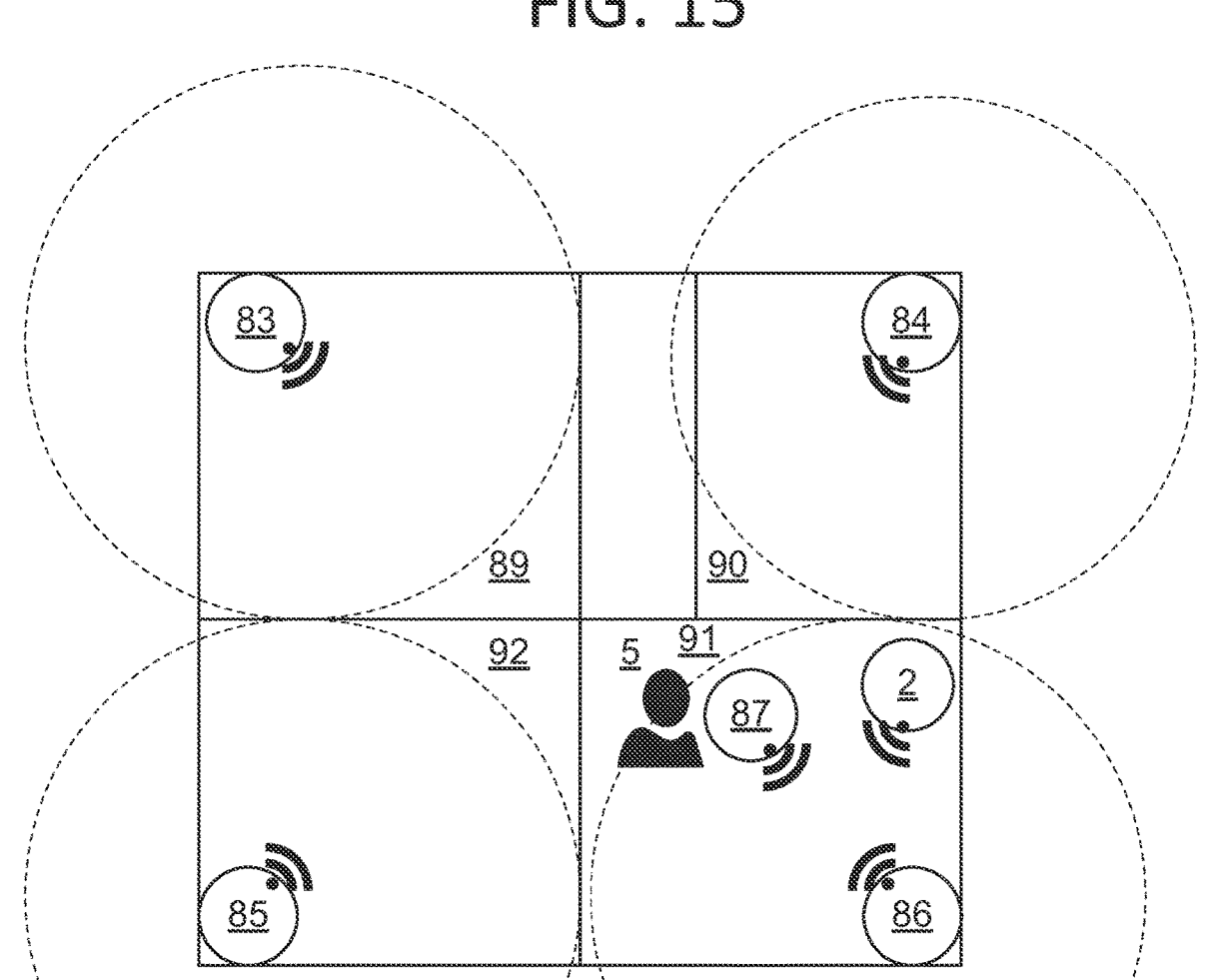
FIG. 15 depicts a patient, the mobile application, tracker device, and positioning devices located in a treatment area and the coverage area of the positioning devices.

FIG. 15 depicts a treatment room with the patient 6, the mobile application 2 used by the patient 6, positioning devices 83-86 (e.g., beacons) and their coverage areas coverage area 89-92, and tracker device 87 (e.g., wristband). In some embodiments, the positioning devices 83-86 can transmit notifications to the mobile application 2 or the web service 3 depending on the transition and stay times between the tracker device 87 connected to the patient 6, the coverage area inside the treatment area (e.g., house), and networks thereof.

The positioning devices 83-86 enable more effective use of the urinary diary. The positioning devices 83-86 can be beacons or indoor positioning sensors. The positioning devices 83-86 include coverage areas that indicate the coverage area of each positioning device. The positioning devices 83-86 can maintain a connection with the mobile application 2 or the web service 3.

The tracker device 87 can be an indoor positioning device that is connected to or worn by the patient 6. The tracker device 87 can be a wristband that is attached to the patient 6 when the urinary diary in the mobile application 2 is tracked (e.g., the urinary diary applied over the course of the treatment at the beginning, middle, end thereof). The tracker device 87 can maintain a connection with the mobile application 2 or the web service 3. For example, the web service 3 can identify a location of the tracker device 87 and thus the location of the patient 6 when the patient 6 leaves their phone (executing the mobile application 2) in a room and moves around.

Section D: Web Service

FIGS. 16-25 depict GUIs generated by the web service 3 for display by the web application 5 for treatment management and monitoring. The web service 3 runs in the background of the web application 5. The transcutaneous posterior tibial nerve stimulation device and the mobile application 2 can be remotely monitored by a web service 3. The web service 3 can monitor the course of treatment in the treatment of urinary incontinence, fecal incontinence, pelvic pain, and sexual dysfunction.

Figure 16:
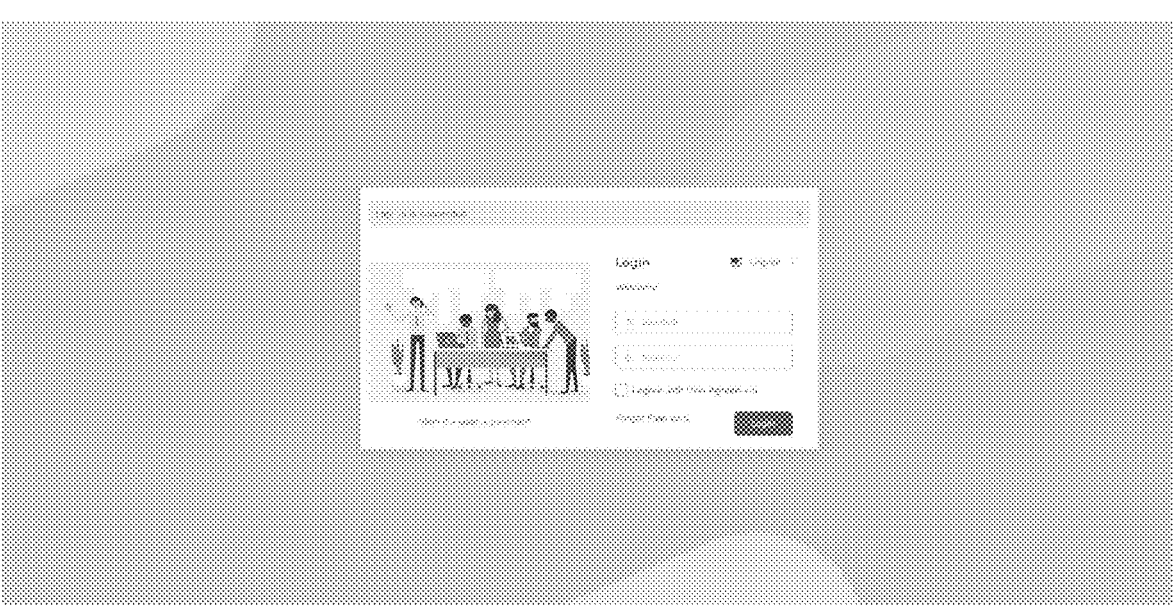

FIG. 16 depicts an interface displayed by the web application 5 for the healthcare provider 7 to configure treatment for the patient 6. The web service 3 can manage the registration of the patient 6, the registration of the neuromodulation device 1, the remote treatment, and the information input and displayed by the web application 5. The web service 3 can cause the web application 5 to display a login screen for the healthcare provider 7. In some embodiments, the web service 3 can receive, from the healthcare professional 7 via the login screen displayed by the web application 5, the identifier number and the password assigned to the healthcare professional 7.

Figure 17:
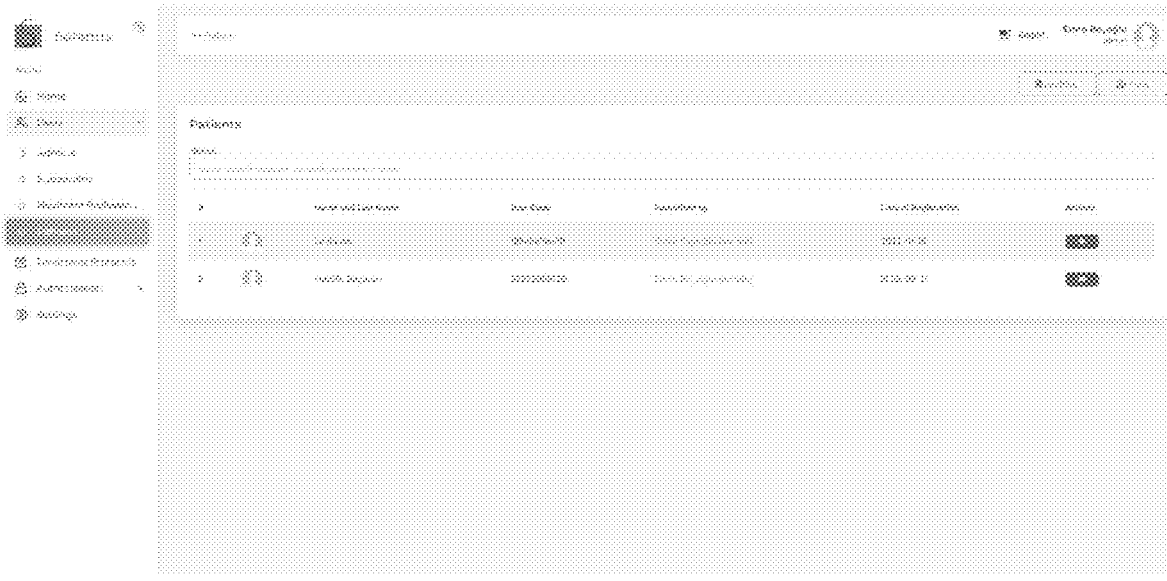

FIG. 17 depicts an interface displayed by the web application 5 for the healthcare provider 7 to manage treatment for the patient 6. In some embodiments, after validating the identifier and password, the web service 3 can cause the web application 5 to display the interface shown in FIG. 17.

Figure 18:
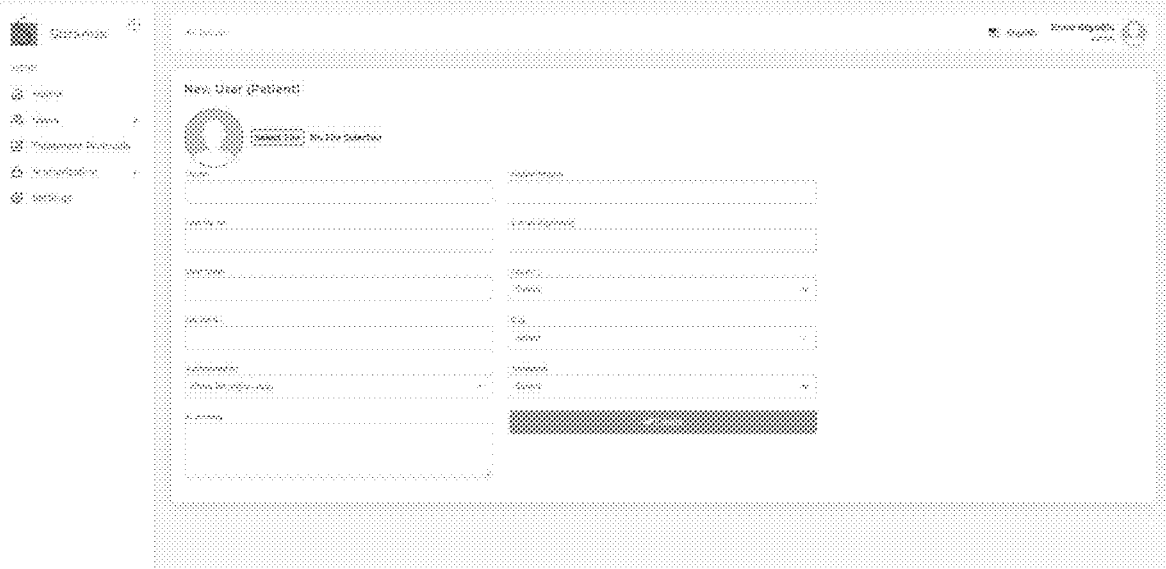

FIG. 18 depicts an interface displayed by the web application 5 for the healthcare provider 7 to configure treatment for the patient 6. The web service 3 can receive patient information provided by the healthcare professional 7 into the web application 5. The web service 3 can store or maintain the patient information provided by the healthcare professional 7 into the web application 5.

Figure 19:
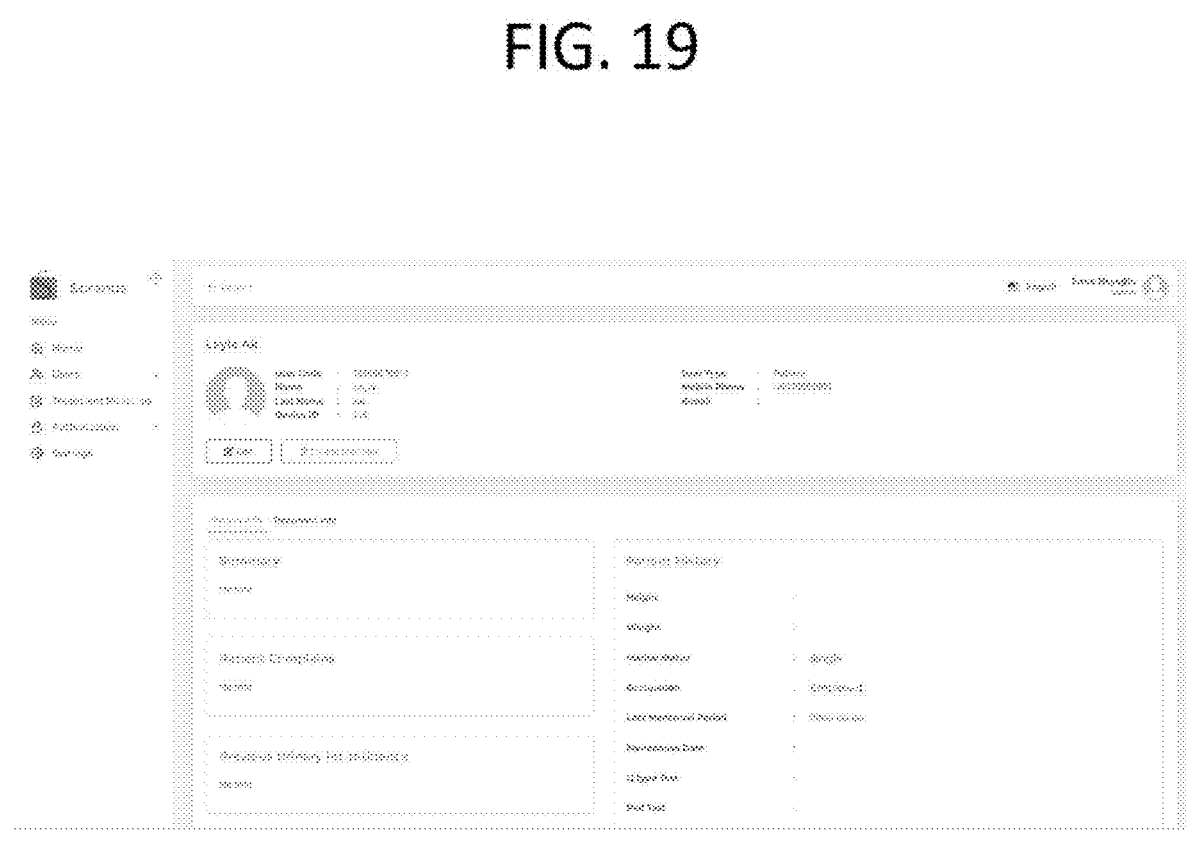

FIG. 19 depicts an interface displayed by the web application 5 for the healthcare provider 7 to view information about the patient 6. The web service 3 can transmit the information to the web application 5 for display to the healthcare professional 7.

Figure 20:
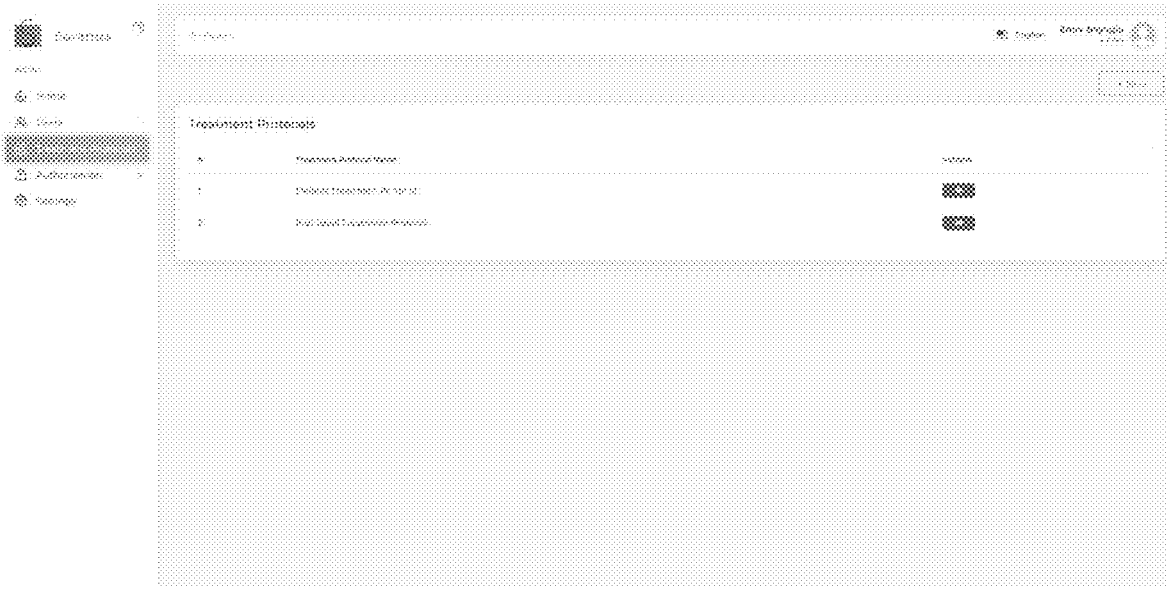
Figure 21:
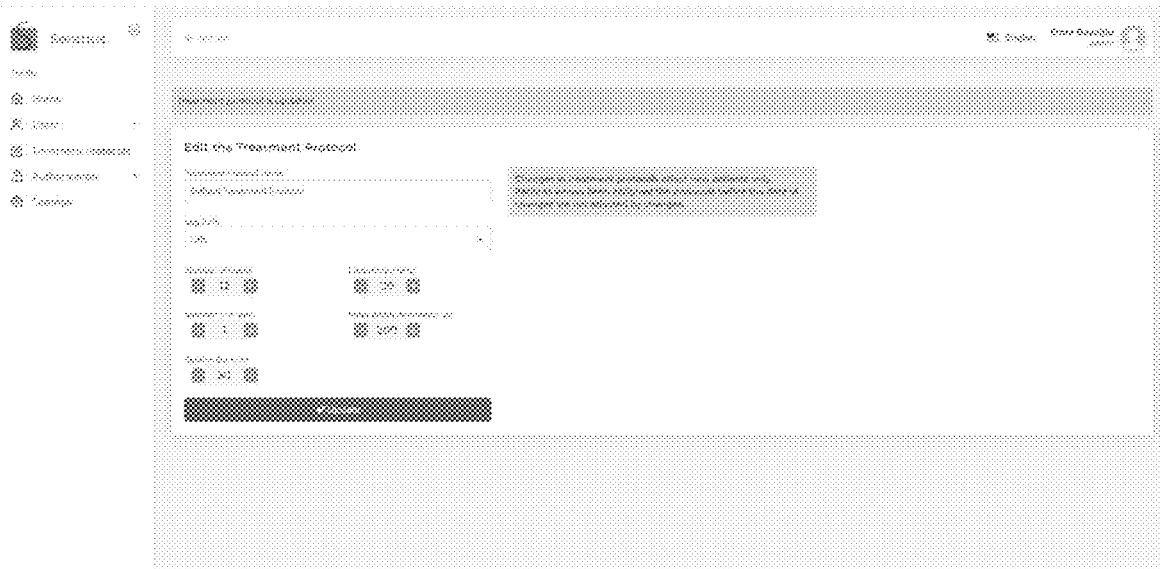

FIG. 20 depicts an interface displayed by the web application 5 for the healthcare provider 7 to view treatments available to assign to the patient 6. FIG. 20 depicts an interface displayed by the web application 5 for the healthcare provider 7 to configure a treatment for the patient 6. The web service 3 can receive, from the healthcare provider 7 via the web application 5, parameters of the treatment protocol such as duration, pulse width and frequency values. For example, the web service 3 can receive a treatment protocol that defines treatment current (e.g., 0-60 mA), pulse width (e.g., 40-400 us), frequency (e.g., 1-50 Hz), duration of each treatment session (e.g., 0-30 minutes), or total treatment duration and treatment intervals (e.g., 1-12 weeks, 1 to 7 times per week, etc.). FIG. 21 shows example reference values for the treatment parameters of the treatment protocol of urinary incontinence such as a treatment duration of 12 sessions in total, applied once or a week, for a session duration of 15 minutes, a pulse width of 200 us, and a pulse frequency of 20 Hz.

Figure 22:
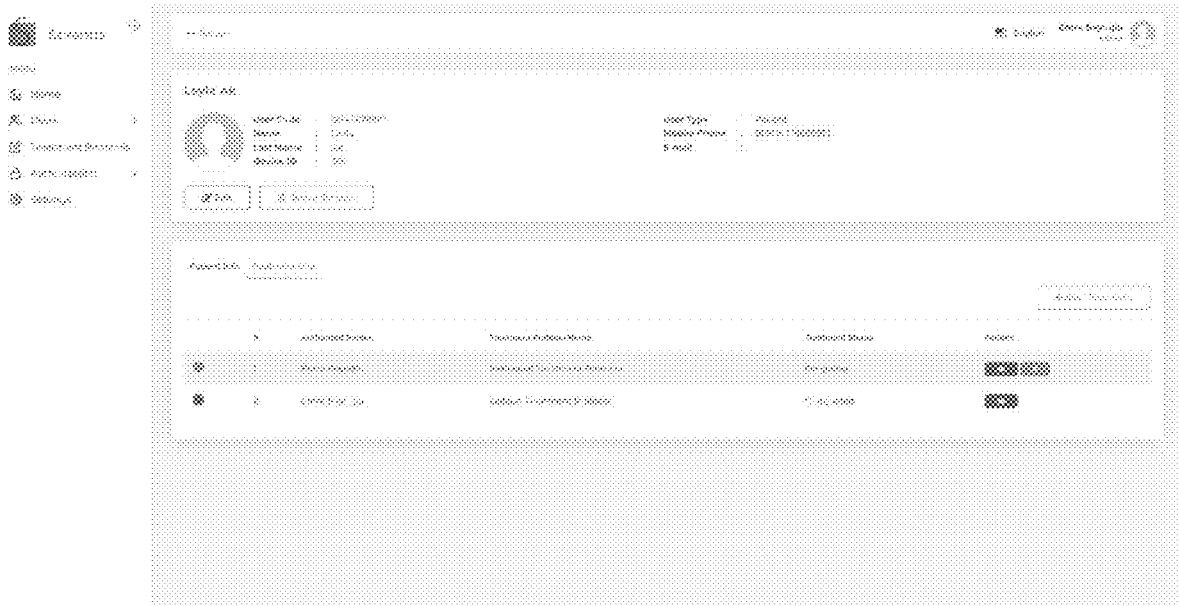
Figure 23:
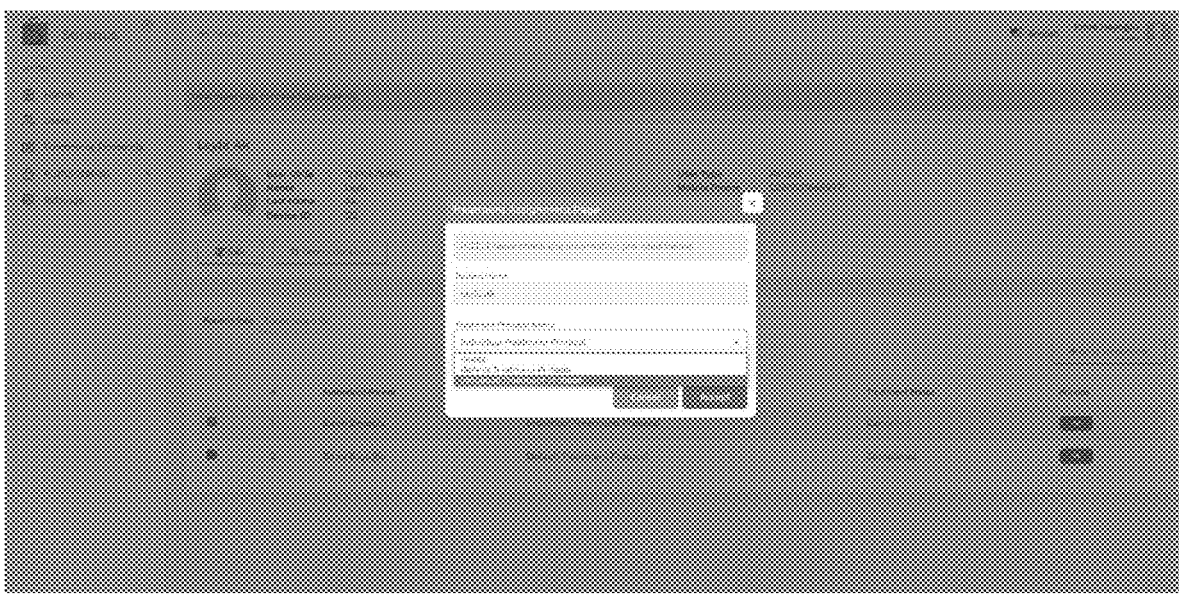

FIG. 22 depicts an interface displayed by the web application 5 for the healthcare provider 7 to view treatments assigned to the patient 6. FIG. 23 depicts an interface displayed by the web application 5 for the healthcare provider 7 to accept an assigned treatment for the patient 6. The web service 3 can transmit the treatment parameters (e.g., schedule, treatment duration, frequency, pulse width, etc.) of the assigned treatment to the neuromodulation device 1 or the mobile application 2 of the patient 6. The web service 3 can provide the treatment to the mobile application 2 for configuring the neuromodulation device 1 to provide treatment to the patient 6 at home without making any additional protocol adjustments. For example, the neuromodulation device 1 can apply mono phasic current pulses up to 60 mA (60 V at 1000-ohm load) for neuromodulation. In some embodiments, the web service 3 controls the neuromodulation device 1 by transmitting the treatment protocol assigned by the healthcare provider 7 via mobile application 2 to the neuromodulation device 1. In some embodiments, the web service 3 controls the mobile application 2 by managing which notification can be sent and when. In some embodiments, the web service 3 transmits notifications (such as e-mails, SMS, etc.) to the healthcare provider 7 regarding the efficacy and details of the treatment.

Figure 24:
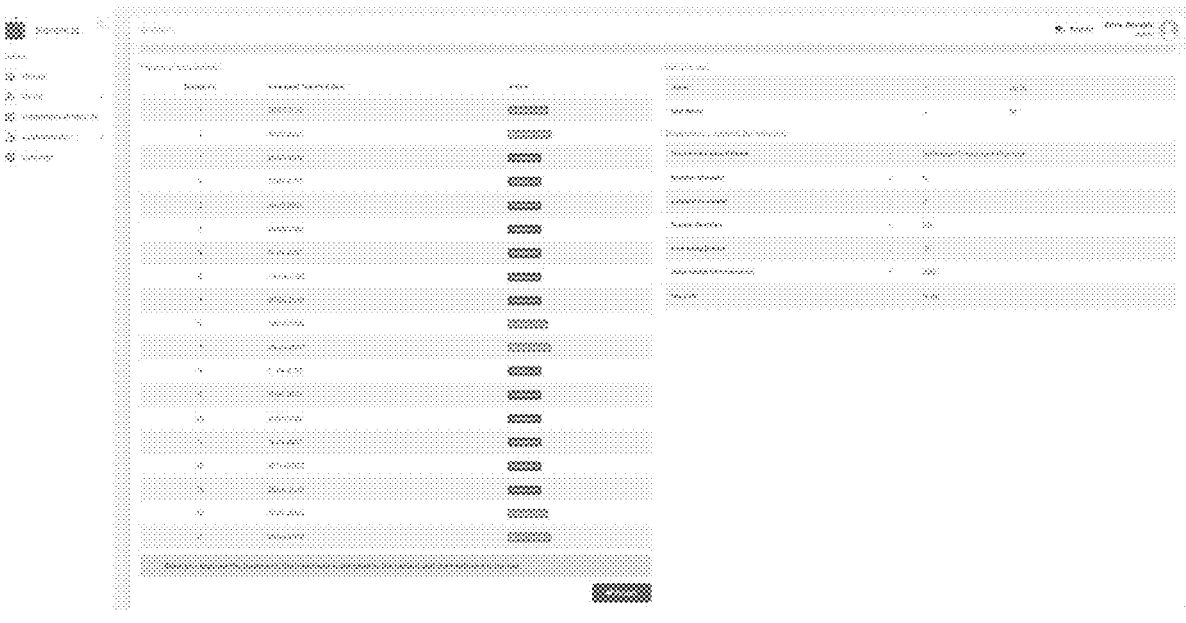

FIG. 24 depicts an interface displayed by the web application 5 for the healthcare provider 7 to view a schedule of the treatment assigned to the patient 6. The web service 3 can receive treatments assigned by the healthcare professional 7 from the web application 5.

Figure 25:
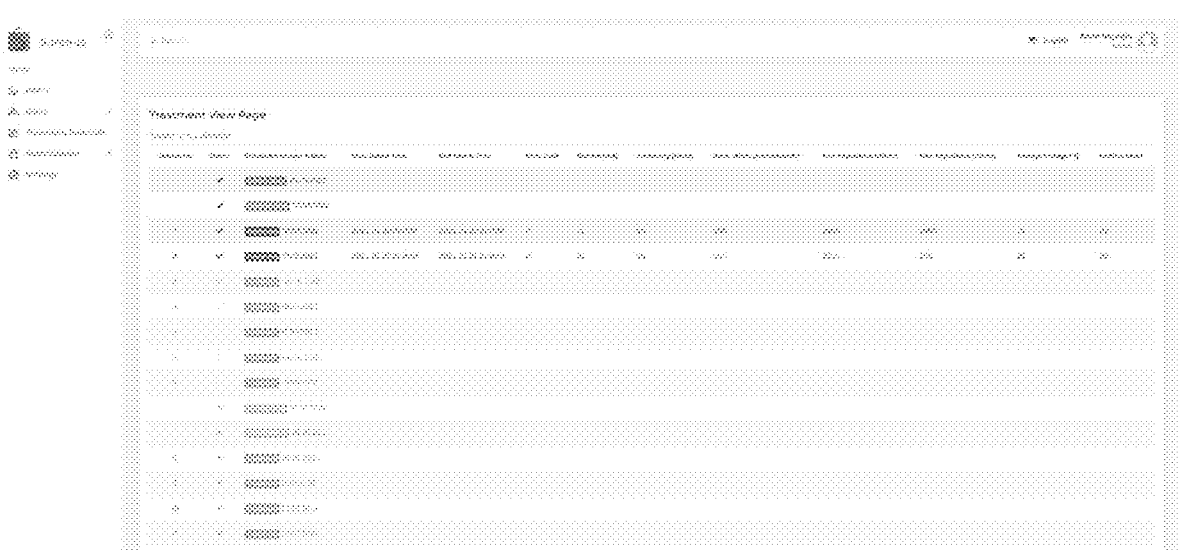

FIG. 25 depicts an interface displayed by the web application 5 for the healthcare provider 7 to view treatment activities associated with the treatment assigned to the patient 6. The web service 3 receives the treatment activities from the neuromodulation device 1 or the mobile application 2. The web service 3 receives treatment activities identified by the neuromodulation device 1 (e.g., location, current, frequency, pulse width, electrical resistance, voltage, mobility, etc.) and treatment activities provided by the patient 6 via the mobile application 2 (e.g., answers to urinary diary or questionnaire). The web service 3 can maintain or store the treatment activities and related functions and in a database. The entered data of the patient 6, and the data from the neuromodulation device 1 after treatment can be stored in the database.

The web service 3 can identify the location of the patient 6 to refine the treatment assessments by prompting the patient 6 to enter more accurate data into their urinary diary and to prompt the patient 6 for self-monitoring of their treatment to increase patient 6 awareness and enhance treatment success. Based on the location of the patient 6, the web service 3 can transmit notifications (e.g., reminders, push notifications, or gamification feedback) to the mobile application 2 for display. The notifications can remind the patient 6 to consume fluids or indicate voiding by the patient 6 (e.g., emptying the bladder and/or the bowls).

For example, if the location identified by the web service 3 indicates that the patient 6 is in a kitchen, then the patient 6 might be drinking fluids. To verify that patient accurately reports their fluid intake into their urinary diary, the web service 3 can transmit a notification to the mobile application 2 to prompt the patient 6 to describe any fluid intake. In another example, if the location identified by the web service 3 indicates that the patient 6 visits the restroom, the web service 3 can improve the tracking process and accuracy of the urinary diary by transmitting questions to the mobile application 2 about whether the patient 6 has urinated.

By means of the positioning devices 83-86 used, depending on the transition and stay times between the tracker device 87, the positioning device coverage area 89-92 inside the house and networks thereof, the web service 3 can identify the location of the patient 6. The web service 3 can communicate with the positioning devices 83-86 and the tracker device 87 to receive location-based treatment activities to identify a location of the mobile application 2 or the tracker device 87 to identify a location of the patient 6. The web service 3 can receive location information from each of the positioning devices 83-86 and the tracker device 87. Based on the received location information, the web service 3 can determine the location of the tracker device 87 and thus the patient 6. In some embodiments, the web service 3 can communicate with the tracker device 87 to identify the location of the patient 6 to continue receiving accurate location information if the patient 6 leaves their mobile device and moves to different locations.

Since the healthcare personnel can remotely monitor all treatment sessions and treatment efficacy, the patient 6 can continue their treatment at home with the applications included in the neuromodulation device 1 without going to the hospital. The patient 56 can use a mobile device such as a smartphone to execute the mobile application 2 to connect to the neuromodulation device 1 via a wired or wireless connection (e.g., Bluetooth connection) for the patient 6 to manage the treatment process in accordance with the associated audible and visual instructions.

The web service 3 can analyze the treatment activities, which can improve and strengthen the effect of the actual treatment, which can be effective especially in overactive bladder, and minimizing the nocebo effect. By providing a personalized treatment experience with the treatment activities collected, the systems and methods described herein provide outputs about the effectiveness and potential of the standard treatment periods.

During the treatment, the web service 3 receives treatment activities in a schedule planned by the healthcare provider 7 and transmits it to the mobile application 2 and neuromodulation device 1. The web service 3 enables the neuromodulation device 1 to be tracked by the patient 6 with the visual and audible notifier that indicates that the treatment has started and continues. If the treatment is disrupted and not performed as planned, or the instructions are not followed, then the web service 3 provides a notification feedback for the healthcare provider 7. The web service 3 can receive data describing the use of the neuromodulation device 1 by the patient 6, the intermittent feedbacks with the urinary diary and validated questionnaires contained therein. The web service 3 can transmit the data and the information in reports about the treatments to the web application 5 for viewing by the healthcare provider 7. The healthcare provider 7 can analyze the treatment activities to optimize the treatment protocol to minimize the problem of dropout of the treatment. For obtaining the urinary diaries, the use of indoor positioning device that support correct input of records, especially in case of elderly patients, increases the effect of the feedbacks.

The patient 6 knowing that their treatment is monitored by the healthcare provider 7 has the effect of strengthening placebo effect and minimizing nocebo effect. For example, the fact that the patient 6 knows that they are receiving treatment can enhance treatment. The enhanced treatment can the OAB and sexual dysfunction patient problem that patients drop out of the treatment. The reminders can help the patient 6 stay with the treatment. The behavioral treatment can be the first line of treatment. For example, for bladder training or going to the restroom at predetermined times. The patient 6 using questionnaires for tracking symptoms can create cognitive awareness and behavioral changes. Such efforts can make sure that the patient still administers treatments. The treatment can be based on objective measures instead of subjective statements by the patient 6.

As a result of the data collected about the treatment, the web service 3 can calculate derived results to primarily monitor the effectiveness of the treatment. Example types of treatment success data are derived to monitor treatment success include success in continuing the treatment and success of treatment. The success of the treatment can be classified as complete recovery, partial and unsuccessful according to the numerical results obtained from the validated questionnaires. The success of continuing the treatment can be measured based on patient's adherence to a treatment calendar. This can be scored from 1 (unsuccessful) to 4 (completely successful). During the total treatment period, the cumulative delay can be scored 4 points if it is between 0-6 days, 3 points between 7-13 days, 2 points between 14-20 days, and 1 point if it is more than 21 days. The mobile application 2 can notify the patient 6 about the success of the treatment, gives points by gamifying the treatment, and increases adherence to the treatment.

The web service 3 can measure treatment success as field-value pairs (e.g., points/scores) based on the result of validated questionnaires conducted at the beginning, middle, and end of the treatment calendar. The web service 3 can display the measurements to the healthcare provider 7 via the web application 5.

The web service 3 can maintain a reference score as baseline reference for treatment success. For example, the web service 3 can generate the reference score after the first assessment done at the beginning of the treatment. The assessment can be repeated at the middle and at the end of treatment, and the scores obtained at the middle and end can be compared to the reference score that was obtained at the beginning of treatment. The web service 3 can address the assessment by verifying if the patient 6 complied with the treatment protocol (e.g., did the patient 6 get their session as scheduled and as many as scheduled) by checking the consistency of treatment current (did the patient 6 apply a consistent treatment current throughout sessions or did the patient vary the treatment current by an interval exceeding a threshold). If the problems occur due non-compliance or wrong administration by the patient 6, then the web service 3 can transmit notifications to the mobile application 2. If the problems occur for other reasons, then the healthcare provider 7 can assign a new treatment protocol via the web application 5.

The web service 3 can generate or assign classifications or categories to the treatment assessments. For example, the web service 3 can categorize the treatment assessment into 3 categories according to the score intervals, as "successful" (cured), "partial" (improvement) and "unsuccessful". The web service 3 can use the OAB-V8 (which is a patient reported outcome questionnaire used to screen for OAB and measures symptom bother) to assign the classifications or categories. For example, if the patient's score is 8 or higher at the beginning of the treatment, and the score is found less than 8 at the middle or end of treatment, the web service 3 can assign "cure". If at the end, the patient's score is between the beginning score and 8, the web service 3 can assign "improvement". If the score at the end is higher than 8, the web service 3 can assign "unsuccessful". For a similar assessment, the web service 3 can assess the urinary diary (e.g., tool to assess symptoms of OAB and provides wider information than OAB-V8) to assign "cure", "improvement", or "unsuccessful". For example, in response to identifying a reduction by half or more in all baseline symptoms, the web service 3 can assign "improvement" to replace previously assigned "unsuccessful."

The web service 3 can generate recommendations and analysis based on the treatment activities to increase adherence to treatment with sustainable, updatable, and digital patient navigation. The web service 3 can detect or identify problems related to applying the treatment (e.g., significant change at the level of the current applied at a session compared to previous sessions, or problems related to session intervals, or session duration). The web service 3 can communicate the problems by transmitting them to the mobile application 2. Data related to such problems is detected by mobile application 2 and communicated to the patient and healthcare provider 7 via the web service 3, using e-mail, or text, or other similar notifications. The web service 3 advantageously ensures that the treatment progresses correctly.

Treatment problems can relate to patient error selecting a treatment current. For example, the patient 6 might fail to adjust the treatment current at the beginning of each session based on their motor response and/or sensory response at each time (since it can be different at each time). The web service 3 can receive the measurements generated by the neuromodulation device 1 and select the treatment current set by the patient 6 based on the measurements. For example, the web service 3 can adjust the treatment current to a comfortable level for the patient 6 based on the oxygen concentration, leg movements, or electrical feedback of the patient's nerve. The web service 3 can further adjust the treatment current based on the patient's selections via the mobile application 2. The web service 3 can transmit the adjusted treatment current to the mobile application 2 for display and confirmation by the patient 6.

Treatment problems can relate to failure of the patient 6 to comply with the treatment calendar and/or session duration. To remedy this problem, the web service 3 can transmit calendar notifications to the mobile application 2 to alert the patient 6. If the web service 3 fails to receive information that the neuromodulation device 1 was activated according to schedule after the notifications (e.g., patient 6 still misses scheduled sessions or cuts the sessions short, etc.), the web service 3 can transmit notifications to the web application to notify the healthcare provider 7. The web application can display information about the neuromodulation device 1 usage and notifications displayed by the mobile application 2 for the healthcare provider 7 to identify reasons of treatment failure/success based-on data.

The web service 3 can receive, via the web application, the diagnosis confirmed by the healthcare provider 7 (via a provided checklist) interacting with the web application. The web service 3 can receive the checklist from the healthcare provider 7. The web service 3 can prompt the web application to require the healthcare provider 7 to fill this checklist during the registration of the patient 6. The checklist can include criteria relating to proven infection or other obvious pathology (such as bladder stone, tumor). For example, overactive bladder syndrome (OAB) is characterized by urinary urgency, with or without urgency urinary incontinence, usually with increased daytime frequency and nocturia, if there is no proven infection or other obvious pathology (such as bladder stone, tumor). The web service 3 can maintain or store the checklist. By storing the checklist, if the patient 6 changes their healthcare provider, the new healthcare provider can access the checklist and associated information. The web service 3 can provide the checklist to the web application for display to the healthcare provider 7 for confirmation or analysis.

The web service 3 can increase adherence to treatment and success of treatment by updating session intervals (once a week, twice a week, etc.), treatment duration (6 weeks, 12 weeks). The web service 3 can maintain or store information related to patient history (including all diagnostic tests, the treatments they are getting, other diseases, and such) to ensure that another healthcare provider 7 can continue treating the patient 6. The web service 3 can apply machine learning or artificial intelligence (e.g., big data) to identify session intervals, session duration, and other patterns or common factors responsive for treatment failure or success. At the beginning of the treatment, the web service 3 can transmit information to the mobile application 2 to inform the patient 6 about the features that increase adherence to treatment to result in a more attentive use of such features by the patient 6. By generating an individual treatment plan (e.g., "individualization of the treatment"), the web service 3 can provide remote monitoring and assessment to increase the patient's adherence to the treatment calendar of which they are made a part of. The web service 3 and mobile application 2 enable ease of monitoring, assessing, and intervention for the healthcare provider 7 to increase their motivation for successfully treating the patient 6. This ease can increase both adherence of the patient 6 and healthcare provider 7 to the treatment.

The data recorded in the database in the web service 3 constitutes the source for analysis of treatment activities. For example, by monitoring the impedance in the treatment sessions, it can provide data on after how many treatments the hydrogel has completed its life, and how often it needs to be changed. The web service 3 can parse protocols (which can include treatment duration (how many weeks long), session duration (how many minutes each session), interval (how apart each session), frequency (Hz), pulse width (microsecond), treatment current (mA)) to generate suggestions regarding which one is best suited for the patient 6 according to the treatment activities. In another example, the web service 3 can analyze, assess, or categorize unsuccessful results according to analysis of the treatment activities. Based on data collected regarding the patient history, patient compliance, the treatment, and treatment protocol, the web service 3 can use machine learning to generate suggested treatment protocols.

According to this data, the mobile application 2 sends notifications to the patient 6. If there is an unexpected impedance change, it reports whether the treatment is effective or not. If during the treatment session, an exceptional treatment current is applied, or impedance or device-related error codes occur, the healthcare provider 7 and or patient 6 are warned by notifications (e-mail, SMS, mobile application 2 notifications, etc.) created from the web service 3. Thus, the missing or incorrect treatment session can be reassigned by the healthcare provider 7 or the artificial intelligence engine. Such reassignments can also be made based on artificial intelligence without the healthcare provider 7.

Since the treatment protocol can be adjusted via the web application and the effects of potential different treatment protocol combinations on treatment can be measured, new treatment protocols that will be recommended to healthcare provider 7 can be created. The web service 3 can generate alternatives to the reference treatment protocols. For example, the web service 3 can generate new treatment protocols (session duration, interval, frequency, pulse width and such) to be studied at clinical trials, and those with successful results can be added to the learning algorithm of the treatment activities.

The web service 3 can optimize the treatment protocols. For example, instead of applying the treatment twice a week for 6 weeks, alternating legs every other day, the web service 3 can identify a treatment plan to increase the effectiveness of the treatment in less than 6 weeks. The web service 3 can generate such recommendations and inferences based on the treatment activities with the artificial intelligence engine operating in the background of the web service 3.

The web service 3 can receive and maintain data related to patient history, treatment compliance data for each patient 6, treatment current, treatment protocol data (pulse width, pulse frequency, session duration, session intervals, the leg used), treatment outcome data, data from the neuromodulation device 1 (both treatment related data and device related data), data from the sensor device 10. The web service 3 can apply machine learning algorithms to take this input data and generate output data that comprises potential treatment protocol suggestions for individualized treatment protocol options.

Figure 26:
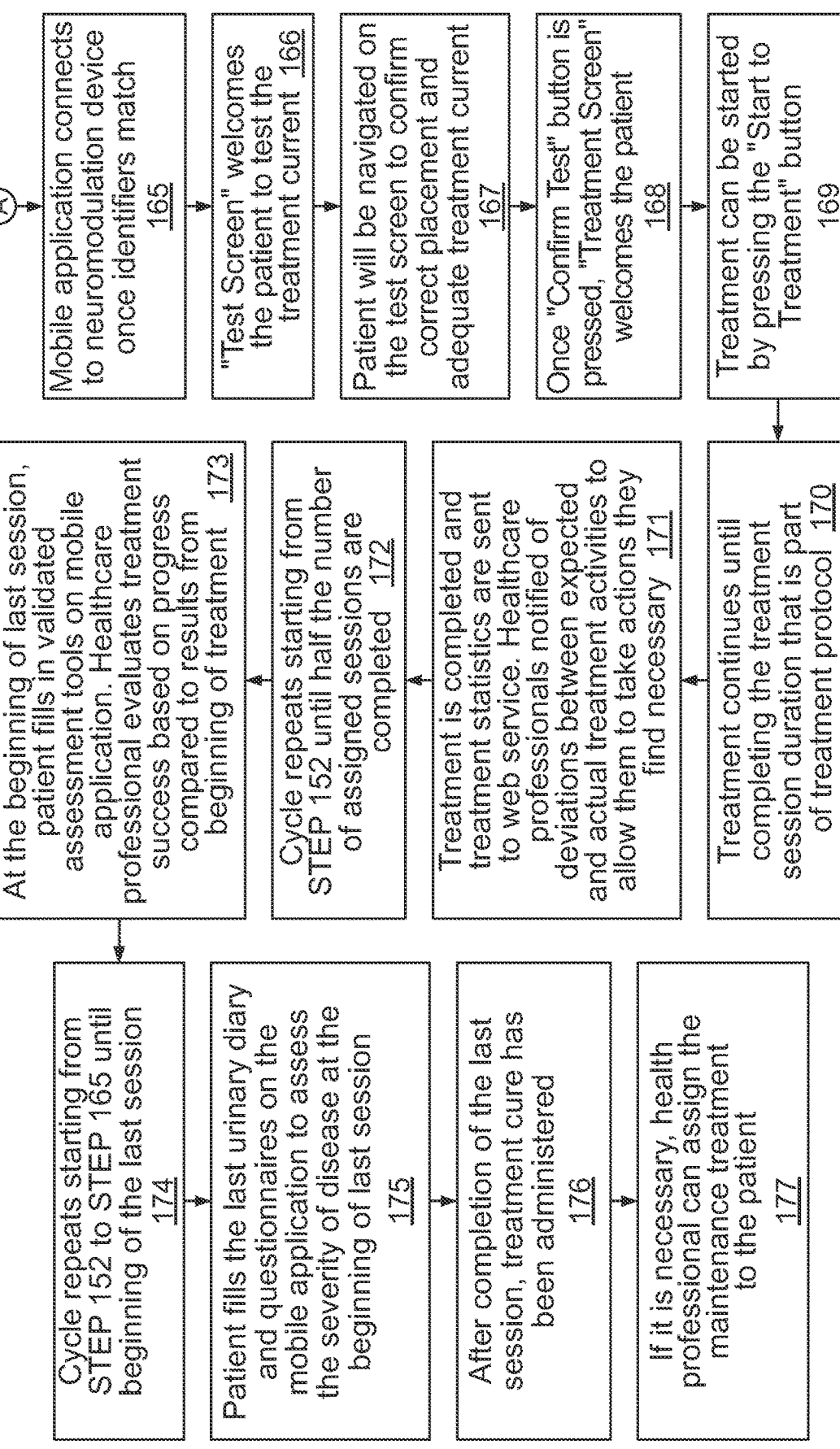
FIG. 26 is a flowchart of operation of the systems described herein.

FIG. 26 is a flowchart of an operation of the systems described herein. The patient 6 can be diagnosed with a syndrome (STEP 151). The patient 6 can purchase the neuromodulation device 1 after the examination by the healthcare provider 7 and the approval for the usage of the patient 6 (STEP 152). The healthcare provider 7 can register the patient identifier and device identifier from the web application 5 (STEP 153). The web service 3 can receive, via the web application, registration information about the patient 6 (with the serial number of the neuromodulation device 1 that belongs to the patient 6). After registering the neuromodulation device 1 in the system, the patient 6 can start their treatment in accordance with the reminder notifications of the mobile application 2 received from the phone (it can be any mobile device that operates applications) via the assigned treatment calendar. The mobile application 2 can receive and display reminder treatment notifications from the web service 3. The neuromodulation device 1 can be configured to be worn by the patient 6.

The healthcare provider can assign a treatment protocol to the patient (STEP 154). The treatment protocol parameters registered in the system can be updated, if necessary, by the healthcare provider 7 via this web service 3. The treatment protocol parameters that can be changed via the web service 3 include number of weeks, Interval (how many times it will be applied in a week), Treatment duration, Treatment Pulse Frequency, Treatment Pulse Width, Leg to be Used (Right and/or Left). The patient 6 can log into the mobile application 2 by using their patient identifier and the mobile application 2 can redirect the patient 6 to the assessment screen (STEP 155). The mobile application 2 can enable the patient 6 to login into the system by entering the patient ID number and the password assigned to them on the login screen. The patient 6 can fill the first urinary diary and questionnaires on the mobile application 2 to assess the severity of their disease (STEP 156). The results can be communicated to healthcare professional and stored on the web service 3 (STEP 157). The mobile application 2 can notify the patient 6 of the treatment session dates (STEP 158). The patient 6 can put batteries into the neuromodulation device 1 and adhere the hydrogels on both electrodes 40 and 41 of the neuromodulation device 1 to the treatment site (STEP 159). The neuromodulation device 1 can be configured to have its "−" electrode placed just above the tarsal tunnel, and the "+" electrode parallel to the orientation of the nerve by the patient 6, which enable the electrical pulses of the neuromodulation device 1 to be transmitted to the skin with hydrogels.

The patient 6 can adhere the neuromodulation device 1 according to instructions provided on the mobile application 2 or the help of augmented reality camera interface that illustrates the neuromodulation device 1 on the patient's treatment site such as their leg (STEP 160). The patient 6 can turn on the neuromodulation device 1 by pressing the button, after which the neuromodulation device 1 is ready to connect with the mobile application 2 (e.g., via Bluetooth) (STEP 161). The LED of the neuromodulation device 1 can flash (e.g., green flash) and the buzzer can make noise or buzz when the neuromodulation device 1 is turning on (STEP 162).

When the patient 6 opens the mobile application 2, a treatment take screen can welcome the patient 6 (STEP 163). When the patient 6 presses the "start" button, the mobile application 2 can try to connect to the web service 3 to receive the treatment protocol assigned by the healthcare provider 7 (STEP 164). In some embodiments, when the patient 6 presses the "receive treatment" button on the application, the confirmation can be received by the mobile application 2 on the notification screen and the treatment protocol input in the web service 3 by the healthcare provider 7 can be retrieved from the web service 3 via the Internet. The mobile application 2 can attempt to connect to the neuromodulation device 1 (STEP 165). The mobile application 2 can establish the connection if the device identifier matches the patient identifier. The "Test Screen" can request that the patient 6 to test and adjust the treatment current (STEP 166). The patient 6 can navigate the "Test Screen" to confirm a treatment current (STEP 167). The mobile application 2 can include automatically switching to the "Test Screen" with the mobile application 2 and connecting with the neuromodulation via the communication circuit. The mobile application 2 can display, after establishing the connection, the "Test Screen" on the mobile application 2. The method can include the patient 6 pressing the "start test" button by when appropriate and adjusting the current. The method can include the patient 6 pressing the "Stop Test" button by the patient 6 at the point where they feel comfortable (provided that the sensory response continues). When the patient 6 presses the "confirm test" button, the "treatment screen" can welcome the patient 6 (STEP 168).

The treatment can be started when the patient 6 presses the "Start Treatment button (STEP 169). The method can include the neuromodulation device 1 transmitting, as soon as pressing the "start" button in the mobile application 2, the current to the leg to be used (right and/or left) based on the assigned treatment protocol (pulse frequency, pulse width, and duration) from the treatment current determined on the test page, while seeing the time from the counter on the screen. The treatment can continue until completing the treatment session duration that is part of the treatment protocol (STEP 170). The treatment can be completed and treatment statistics such as data can be sent to the web service 3 (STEP 171). In some embodiments, the method can include using positioning devices to send the notifications to the mobile device via the mobile application 2 depending on the transition and stay times between the beacon connected to the wristband of the patient, the positioning devices coverage area inside the house, and networks thereof. If any deviation occurs between expected and received treatment activities, notifications can be sent to the health care professional to let them check the treatment efficacy. The treatment cycle can continue from STEP 152 until half of the number of assigned sessions are completed (STEP 172).

The patient 6 can fill the second urinary diary in questionnaires on the mobile application 2 to assess the severity of disease in the middle of treatment schedule (STEP 173). The cycle can repeat from STEP 152 to STEP 165 until the beginning of the last session (STEP 174). The patient 6 can fill the last urinary diarrhea and questionnaires on the mobile application 2 to assess the severity of disease at the beginning of the last session (STEP 175). After completion of the last session, the treatment cure has been administered from (STEP 176). If it is necessary, the healthcare provider 7 can assign the maintenance treatment to the patient 6 (STEP 177).

Figure 27:
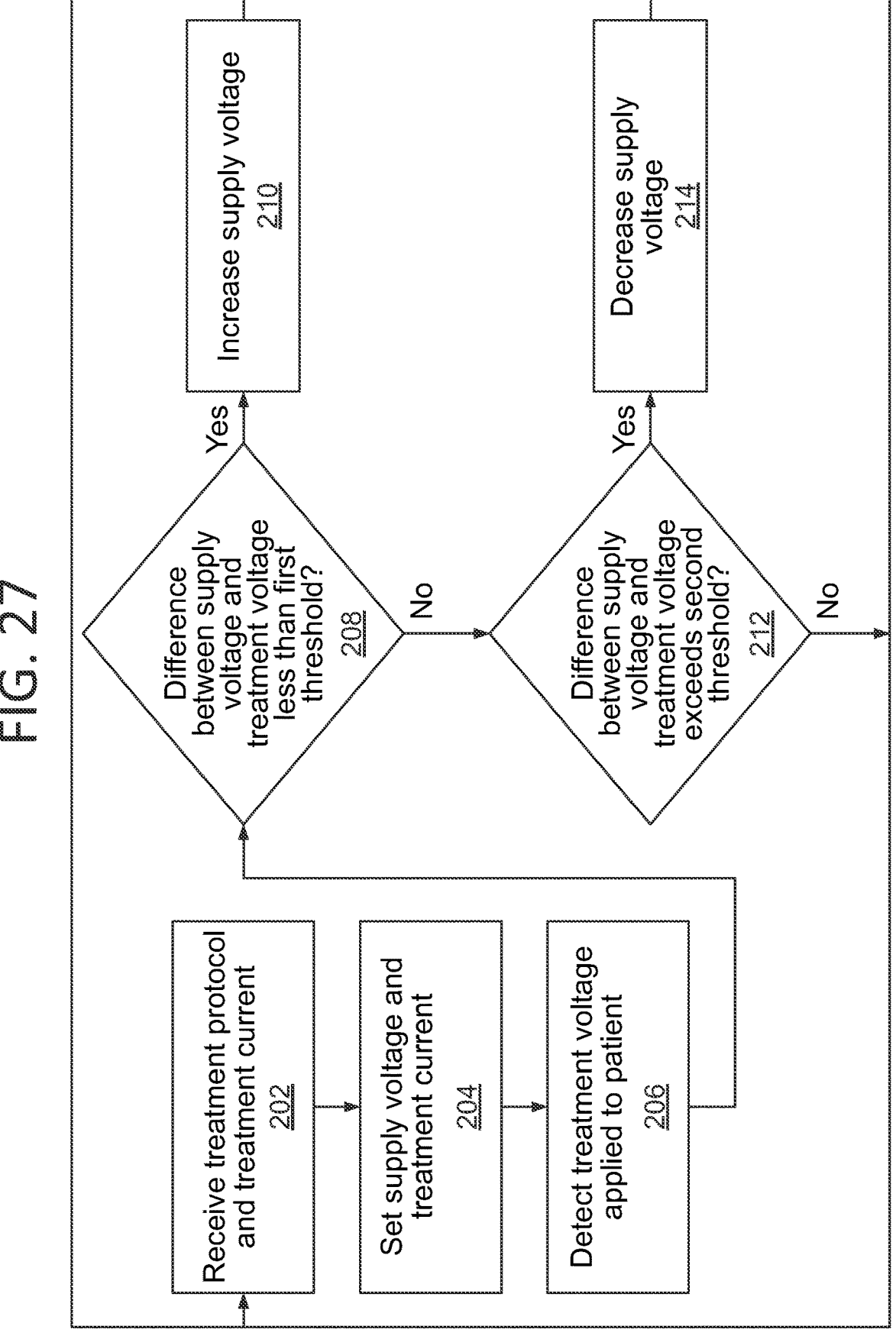
FIG. 27 is a flowchart of a method for applying neuromodulation by a neuromodulation device.

FIG. 27 is a flowchart of a method for applying neuromodulation by a neuromodulation device 1. The method can include receiving treatment protocol and treatment current (STEP 202). The communication unit 75 allows the neuromodulation device 1 to be used as an indoor positioning device and/or data exchange with a mobile application 2.

The method can include setting a supply voltage and treatment current (STEP 204). The microcontroller can extract the voltage and current parameters from the treatment protocol information received via the communication unit 75 from the mobile application 2. The microcontroller can generate a signal for the constant current source based on the voltage and current parameters. The microcontroller can transmit the signal to the constant current source to apply the treatment current to the patient.

The neuromodulation device 1 causes the DC/DC step-up converter 66 to output a supply voltage ($V_{supplied}$). For example, the supplied voltage can be set to a minimum ($V_{min}$) of 15 V. The output voltage of the DC/DC step-up converter 66 can be increased from the minimum level according to the voltage requirement as the treatment current is increased, and vice versa. The neuromodulation device 1 identifies the treatment current of (beat). In some embodiments, the neuromodulation device 1 identifies the treatment current to the treatment current selected by the patient 6 via the mobile application 2.

The method can include detecting a treatment voltage applied to the patient (STEP 206). The neuromodulation device 1 can identify the treatment voltage ($V_{treat}$) for providing the treatment current to the patient 6. The neuromodulation device 1 can identify the treatment voltage by multiplying the treatment current by the impedance (e.g., $V=I*R$). The neuromodulation device 1 can identify the impedance (according to equation 2) of the electrode impedance 80A and 80B, hydrogel 81A and 81B, and skin impedance 78 connected between the electrodes 40 and 41. In some embodiments, the equivalent average impedance value and treatment current can be defined by selections received from the patient 6 via the mobile application 2. In some embodiments, the neuromodulation device 1 or the mobile application 2 calculates the equivalent average impedance value. For example, if the patient set the treatment current value to 15 mA and the value corresponding to the equivalent impedance (equation 2) is 2000 ohms. The voltage value to be created between the positive electrode terminal 41 and the negative electrode 40 terminal through a constant current source 60, according to equation 2, would be 30V.

The neuromodulation device 1 can select the supplied voltage to minimize power loss and maximize efficient use of the battery 47 while providing the selected treatment current to the patient. The regulation of the supply voltage reduces consumption can reduce power consumption and improve energy efficiency. For example, if the supply voltage of the DC/DC step-up converter 66, and thus the supplied voltage to the input of the constant current source 60, remained constant at 60V while the treatment voltage was 30V, there would be power loss, which means additional consumption from the battery 47. The power loss is calculated in equation 3:

$$P_{loss}=P_{supplied}-P_{treatment}$$

$$P_{loss}=(I_{supplied}*V_{supplied})-(I_{treatment}*V_{treatment})$$

$$P_{loss}=(15 \text{ mA}*60 \text{ V})-(15 \text{ mA}*30 \text{ V})$$

$$P_{loss}=450 \text{ mW} \quad\quad\quad \text{Equation 3:}$$

The closer the supplied voltage of the DC/DC step-up converter 66 is to the treatment voltage between the positive treatment electrode 41 and the negative treatment electrode 40 of the constant current source 60, the smaller the power loss while providing the treatment current, which enables efficient use of the battery 47.

The method can include determining if a difference between treatment voltage and supply voltage exceeds a first threshold (STEP 208). In some embodiments, the neuromodulation device 1 can subtract the treatment voltage from the supplied voltage. If the result is less than a lower voltage threshold ($V_{threshold1}$), then the flow can proceed to STEP 210. For example, if the supplied voltage is 45V and the treatment voltage is 50V, then the result of –5V is less than a lower voltage threshold of –1V and the supplied voltage can be increased to provide the desired treatment current to the patient 6. If the result is not less than the lower voltage threshold, then the flow can proceed to STEP 212. For example, if the supplied voltage is 55V and the treatment voltage is 50V, then the result of 5V is not less than the lower voltage threshold of –1V and the supplied voltage can be decreased to minimize power loss while providing the selected treatment current to the patient 6.

The neuromodulation device 1 can compare the supplied voltage to the maximum voltage ($V_{max}$) that can be output by the DC/DC step-up converter 66. For example, the neuromodulation device 1 and the DC/DC step-up converter 66 might be able to output a max voltage of 60V (e.g., maximum safe voltage for neuromodulation). If the supplied voltage is already at the max voltage, then the flow proceeds to STEP 202 because the supplied voltage cannot be further increased. For example, if the supplied voltage is 60V and the max voltage is 60V, then the supplied voltage is at the max value and cannot be increased. If the supplied voltage is less than the max voltage, then the flow can proceed to STEP 210 because the supplied voltage can be increased. For example, if the supplied voltage is 45V and the max voltage is 60V, then the supplied voltage can be increased to provide the selected treatment current to the patient 6.

If the difference exceeds the first threshold, the method can increase the supply voltage (STEP 210). The neuromodulation device 1 can cause the DC/DC step-up converter 66 to increase the supply voltage. For example, if the supplied voltage is 45V and the treatment voltage is 50V, then the neuromodulation device 1 can cause the DC/DC step-up converter 66 to increase the supply voltage to 50V to provide the desired treatment current to the patient 6. The method can proceed to STEP 202 to check for updates to the treatment current, supply voltage, and treatment voltage.

If the difference does not exceed the first threshold, the method can determine if a difference between treatment voltage and supply voltage exceeds a second threshold (STEP 212). The neuromodulation device 1 can subtract the treatment voltage from the supplied voltage. If the result is greater than an upper voltage threshold ($V_{threshold2}$), then the flow can proceed to STEP 214. For example, if the supplied voltage is 55V and the treatment voltage is 50V, then the result of 5V is greater than the upper voltage threshold of 1V and the supplied voltage can be decreased to minimize power loss. If the result is not greater than the upper voltage threshold, then the flow can proceed to STEP 202. For example, if the supplied voltage is 50V and the treatment voltage is 50V, then the result of 0V is not less than the upper voltage threshold of –1V (STEP 208) and not greater than the upper voltage threshold of 1V, so the supplied voltage can remain unchanged while providing the desired treatment current to the patient 6.

The neuromodulation device 1 can compare the supplied voltage to the minimum voltage ($V_{min}$) that can be output by the DC/DC step-up converter 66. For example, the neuromodulation device 1 and the DC/DC step-up converter 66 might be able to output a minimum voltage of 15V (e.g., minimum voltage that can be output because of inherent impedance). If the supplied voltage is already at the minimum voltage, then the flow proceeds to STEP 202 because the supplied voltage cannot be further decreased. For example, if the supplied voltage is 15V and the minimum voltage is 15V, then the supplied voltage is at the minimum value and cannot be decreased. If the supplied voltage is greater than the minimum voltage, then the flow can proceed to STEP 214 because the supplied voltage can be decreased. For example, if the supplied voltage is 45V and the minimum voltage is 15V, then the supplied voltage can be decreased to minimize power loss while providing the selected treatment current to the patient 6.

If the difference exceeds the second threshold, the method can decrease the supply voltage (STEP 214). The neuromodulation device 1 can cause the DC/DC step-up converter 66 to decrease the supply voltage. For example, if the supplied voltage is 50V and the treatment voltage is 45V, then the neuromodulation device 1 can cause the DC/DC step-up converter 66 to decrease the supply voltage to 45V to minimize power loss while providing the selected treatment current to the patient 6.

The method can proceed to STEP 202 to check for updates to the treatment current, supply voltage, and treatment voltage. If the difference does not exceed the second threshold, the method can proceed to STEP 202 to check for updates to the treatment current, supply voltage, and treatment voltage.

Figure 28A:
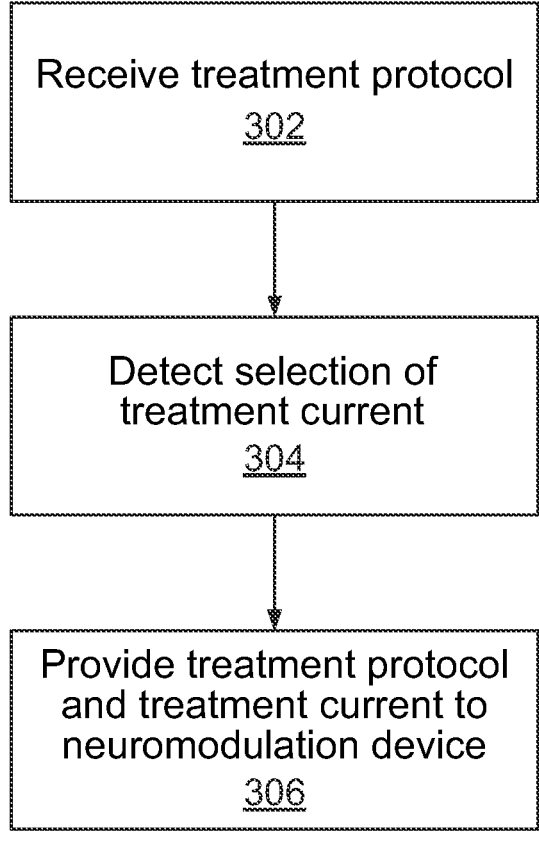
FIG. 28A is a flowchart of a method for managing neuromodulation on a mobile application.

FIG. 28A is a flowchart of a method for managing neuromodulation on a mobile application. The method can include receiving a treatment protocol (STEP 302). The mobile application 2 can monitor the patient 6 by managing the neuromodulation device 1 and receiving treatment activities from the patient 6. The mobile application 2 can transmit the treatment activities to the web service 3. The mobile application 2 can be executed by a mobile device, such as a phone or tablet that belongs to the patient 6. The web service 3 manages the information exchanged with the mobile application 2 and displayed via the web application 5. The web service 3 can communicate with the web application 5 via a connection 4D, such as the internet. The web application 5 is an interface that manages the registration of the neuromodulation device 1 and the patient 6 for the remote treatment. The patient 6 uses the neuromodulation device 1 and mobile application 2 for treatment. The healthcare provider 7 can be a doctor, nurse, or any other medical provider who assigns and controls the treatment.

The neuromodulation device 1 and the mobile application 2 can maintain a connection for registration of the patient 6 and monitoring of the treatment by the patient 6 and the healthcare provider 7. The web service 3 receives data from the mobile application 2 about whether the patient 6 applied the treatment and the status of the treatment. The mobile application 2 can be in communication with the web service 3 administered by the healthcare provider 7. The mobile application 2 can be in communication with the web service 3 to receive treatment protocol information provided by the healthcare provider 7 via the web application 5. The healthcare provider 7 can use a web application 5 that manages the registration of the patient 6 and the neuromodulation device 1 with the web service 3 to manage the information input and displayed via the web application 5. The connections enable the remote monitoring of the delivery of the treatment at adequate treatment values and ensures the effectiveness of the treatment.

The patient 6 can adhere the neuromodulation device 1 to a location on their body and apply the treatment protocol configured by a healthcare provider 7 but without their presence. The transcutaneous posterior tibial nerve stimulation device 1 can be remotely monitored by the healthcare provider 7 to monitor the course of treatment in the treatment of urinary incontinence, fecal incontinence, and pelvic pain. The mobile application 2 can receive the treatment activity from the neuromodulation device 1 and transmit the treatment activity to the web service 3. The web service 3 saves this information and transmits the information to the web application 5 for presentation to the healthcare provider 7. The healthcare provider 7 can access via the web application 5 to make evaluations about the treatment based on this data.

FIG. 10 depicts an interface displayed by the mobile application 2 for the patient 6 to access the mobile application 2 to begin the first treatment and subsequent treatments. The mobile application 2 can display a login screen for the patient 6. In some embodiments, the mobile application 2 can receive, from the patient 6 via the login screen, the identifier number and the password assigned to the patient via the login screen will be displayed by the mobile application 2. For example, when the mobile application 2 receives the patient identifier and password from the patient 6 via the login screen. After validating the patient identifier and password, the mobile application 2 can grant the patient 6 permission to begin treatment steps.

FIGS. 11A-11G depict interfaces displayed by the mobile application 2 for initializing treatment. FIG. 11A shows an interface for starting treatment. When the mobile application 2 detects a selection of the "Start" button, the mobile application 2 can display instructions for placement of the neuromodulation device 1.

FIG. 11B and FIG. 11C show the interface displayed by the mobile application 2 to describe the location where the neuromodulation device 1 will be placed on the leg. The mobile application 2 can provide augmented reality, video, or animations to help the patient 6 to position the neuromodulation device 1 at the correct location on their leg. The mobile application 2 can generate a visual animation, video, or augmented reality for the patient 6 to verify the proper adherence of the neuromodulation device 1.

As shown in FIG. 11B, augmented reality, video, or animations can be displayed in the area marked "VISUAL AID IN THIS SPOT". In some embodiments, the mobile application 2 can generate virtual marks to indicate the exact anatomical location where the electrodes must be adhered. In some embodiments, to provide augmented reality, the mobile application 2 can cause the camera of the mobile device to turn on. When the mobile application 2 detects the patient's leg in the images generated by the camera, the mobile application 2 can generate a virtual image of the neuromodulation device 1 as it can be worn on the patient's leg in the same area marked "VISUAL AID IN THIS SPOT." The augmented reality engine will run in the background of the mobile application 2.

As shown in FIG. 11C, the mobile application 2 can show the leg and how the neuromodulation device 1 is to be adhered to the leg. Thus, the patient 6 will instantly see how to connect the neuromodulation device 1 on their leg. The mobile application 2 can detect a confirmation (e.g., selection of 'YES') from the patient 6 that the neuromodulation device 1 is positioned.

As shown in FIG. 11D, the mobile application 2 can retrieve, from the web service 3 via a connection (e.g., 4B), the treatment protocol assigned in the web service 3 by the healthcare provider 7. The mobile application 2 can start searching for the neuromodulation device 1 via the communication unit 75 such as the Bluetooth circuit.

The mobile application 2 can establish communications with the neuromodulation device 1 responsive to verifying the device identifier of the neuromodulation device 1. For example, when the patient 6 acquires their neuromodulation device 1, the healthcare professional 7 can use the web application 5 to cause the web service to register the device identifier of the neuromodulation device 1 with the patient identifier of the patient 6. When the patient 6 goes home and wants to start their treatment, they can login via the mobile application 2 with their patient identifier. The mobile application 2 can receive, from the web service 3, the device identifier of the neuromodulation device 1 registered for the provided patient identifier and compare it with the device identifier of the neuromodulation device 1 attempting to connect to the mobile application 2. If the mobile application 2 identifiers a match, then the mobile application 2 can establish the communication to begin treatment.

A device identifier of the neuromodulation device 1 can be assigned to the patient 6 by the healthcare provider 7 accessing the web service 3 via the web application 5. The mobile application 2 can receive the assigned device identifier of the neuromodulation device 1 that is assigned from the web service 3. When the neuromodulation device 1 and the mobile application 2 attempt to establish the connection (e.g., Bluetooth), the mobile application 2 can receive a candidate device identifier of the neuromodulation device 1. The mobile application 2 can compare the candidate device identifier of the candidate neuromodulation device 1 attempting to connect to the assigned device identifier of the neuromodulation device 1 that was assigned to the patient 6 by the healthcare provider 7. If the device identifiers match (e.g., the connecting device is the assigned device), then the mobile application 2 can establish the communications and transmit treatment protocol information to the neuromodulation device 1 via the connection (e.g., Bluetooth) between the mobile application 2 and the neuromodulation device 1. The neuromodulation device 1 can receive the treatment protocol information. In some embodiments, if the patient 6 does not start the test stage or the mobile application 2 fails to connect with the neuromodulation device 1 within 5 minutes after the neuromodulation device 1 is turned on, the neuromodulation device 1 turns itself off.

The mobile application 2 can cause a camera of the mobile device to capture a QR code to establish communications with the neuromodulation device 1. In some embodiments, the QR code is disposed on the neuromodulation device 1. In some embodiments, the mobile application 2 receives the candidate device identifier from the patient 6. For example, the patient 6 can type in the candidate device identifier that they see on the neuromodulation device 1. The mobile application 2 can transmit the captured QR code or candidate device identifier to the web service 3 for authentication. Responsive to the mobile application 2 receiving a response from the web service 3 verifying the QR code or candidate device identifier, the mobile application 2 can establish communications with the neuromodulation device 1.

The method can include detecting a selection of treatment current (STEP 304). The mobile application 2 can display the "Test Screen" shown in FIG. 11E if the mobile application 2 connects via the communication unit 75 (e.g., Bluetooth) to the neuromodulation device 1 that is online. The mobile application 2 can display the "Test Screen" to prompt the patient 6 to adjust the treatment current. The patient 6 can adjust the treatment current before each treatment session, according to their motor and/or sensory response.

The mobile application 2 can display instructions for the patient 6 to increase the current level until they get a motor (e.g., their toe moves) and/or sensory response (e.g., feel tickling sensation). Some healthcare professionals 7 might instruct patients 6 to keep increasing the current level until tolerable but past motor and/or sensory response level. Even if the patient increases the treatment current to a non-tolerable level, the patient 6 can use the mobile application 2 to decrease the treatment current.

The mobile application 2 can receive inputs to increase current at an intensity tolerable to the patient 6. The mobile application 2 can receive selections of treatment current from the patient 6 to produce a motor and/or sensory response. For example, the electric current value can be set to the value that produced a motor response, and the increase in current can be stopped at an intensity tolerable to the patient 6. The patient 6 can do this without the assistance of the healthcare provider 7 and outside of hospital setting.

As shown in FIG. 11F, if the mobile application 2 detects that the patient 6 presses the "start test" button on the "Test Screen", the mobile application 2 can display the adjustment screen to prompt the patient 6 to increase or decrease the treatment current. The mobile application 2 can transmit a command to the neuromodulation device 1 to prepare to apply test treatment current. In some embodiments, the test treatment current starts at 0 mA. The mobile application 2 can detect adjustments to the treatment current by detecting presses of the "INCREASE" button to increase the treatment current or "DECREASE" button to decrease the treatment current. For example, the mobile application 2 can change the treatment current in intervals of 0.5 mA for every press of the button.

The mobile application 2 can detect that the patient 6 presses the "Confirm the Test" to indicate that they feel comfortable (provided that the sensory response continues) at that treatment current. The mobile application 2 can display confirmation messages on the "Test Screen" for the convenience of the patient 6. The confirmation messages can ask the patient to confirm the selected treatment current. In some embodiments, once the patient confirms the treatment current, the neuromodulation device stops applying current.

In some embodiments, if the connection is lost while displaying the interfaces in FIGS. 11E and 11F, the neuromodulation device 1 is configured to stop electrical stimulation to make sure the patient 6 does not receive any electrical current prior to setting the treatment current. Preventing electrical current is an advantageous feature because if the connection disconnects before the patient 6 could set the treatment current, then the neuromodulation device 1 would continue providing the set treatment current despite the disconnection. When the connection is restored, the mobile application 2 can display the interfaces of FIGS. 11E and 11F.

The mobile application 2 can optimize the treatment current based on the sensory threshold level at which the patient 6 reacts to the treatment. For example, the mobile application 2 can set the treatment current to 1.5 times the sensory threshold level. For example, for treatments performed by the transcutaneous route, the treatment application current varies between 10 mA and 20 mA on average and can be different at every session for the same patient 6.

The sensory threshold level of the patient 6 can change over time. Based on general observations in nerve stimulation, the excitation energy threshold of the nerve can increase during or after stimulation. Treatment sessions can be scheduled several days apart (e.g., every 2-3 days) to allow the threshold of the nerve to decrease again. To optimize the treatment current for each patient's unique sensory threshold level, the mobile application 2 can set the treatment current to be unique for each patient 6.

The neuromodulation device 1 can use the feedback electrodes 43 to measure the sensory threshold level energy. When the threshold level energy of the nerve decreases to the level measured at the beginning of the previous treatment, the neuromodulation device 1 transmits a notification to the mobile application 2 for next treatment. The mobile application 2 can display a notification to the patient 6 to indicate that the patient 6 can administer their next treatment session as soon as possible. In this way, immediate treatment is possible without the need for standardized or predetermined waiting intervals between sessions, which can advantageously result in a shorter recovery time. On the other hand, this measurement can enable more frequent treatments that are more effective for patient 6 whose treatment interval (e.g., daily basis) is insufficient.

The method can include providing treatment protocol and treatment current to the neuromodulation device 1 (STEP 306). As shown in FIG. 11G, the mobile application 2 can display that the patient 6 is ready to start the treatment and asks the patient 6 to start treatment. In some embodiments, the mobile application 2 displays the treatment interface shown in FIG. 11G after detecting that the patient 6 selected to confirm the treatment current in the interface shown in FIG. 11F. automatically asking the patient to start treatment. Responsive to the mobile application 2 receiving a selection to start treatment, the mobile application 2 can transmit a command to the neuromodulation device 1 to apply the treatment current confirmed by the patient 6 at the test stage.

The mobile application 2 can display the "Start to Treatment" button, and the mobile application 2 can detect the patient 6 pressing the button to start the treatment. When the mobile application 2 detects the press of the "Start" button shown in FIG. 11G, the mobile application 2 can transmit a signal to the neuromodulation device 1 to begin transmitting the current to the location (e.g., leg) to be used (Right and/or Left) based on the treatment protocol information (Pulse Frequency, Pulse Width, Duration) from the treatment current selected on the test page shown in FIG. 11G. The mobile application 2 can cause the neuromodulation to start the treatment based on the prescribed protocol information from the treatment current selected on the "Test Screen". For example, the mobile application 2 can cause the neuromodulation device 1 to start treatment at the treatment current of 7 mA. When the treatment starts, the mobile application 2 can instruct the neuromodulation device 1 to administer the current with 0.5 mA/second increments until the treatment current set at test mode is reached.

Figure 28B:
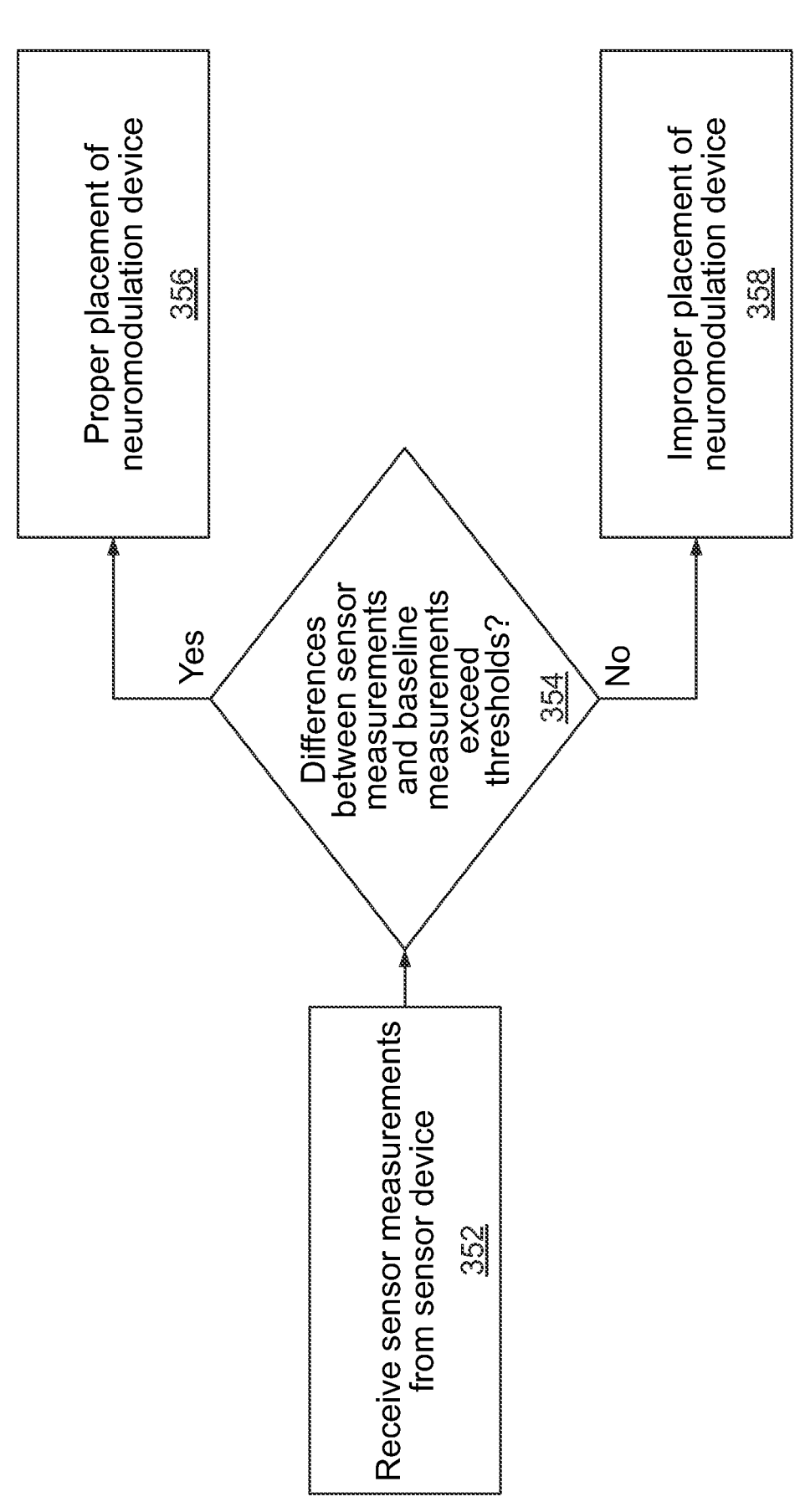
FIG. 28B is a flowchart of a method for verifying placement of the neuromodulation device.

FIG. 28B is a flowchart of a method for verifying placement of the neuromodulation device. The method can include receiving sensor measurements from sensor device 10 (STEP 352). The sensor device 10 can generate measurements of the patient. The sensor device 10 can generate measurements such as electrical signals, oxygen concentration, and tickling movements. The measurements can be indicative of the changes in blood flow and transmit the measurements to the mobile application 2. For example, a neuromodulation device 1 that is correctly positioned on the patient will causes changes in the patient's blood flow by stimulating the tibial nerve. The sensor device 10 can transmit the measurements to the mobile application 2, which can analyze the measurements to verify correct placement of the neuromodulation device 1. The sensor device 10 is configured to be attached to the patient's extremity 12. For example, the sensor device 10 can be attached to the patient's toe of the leg to which the neuromodulation device 1 is adhered.

The sensor device 10 and the neuromodulation device 1 can establish and maintain a connection 4C for communications. For example, the neuromodulation device 1 and the sensor device 10 can establish a Bluetooth connection. It is contemplated that the sensor device 10 can be connected to the neuromodulation device 1 via a wired connection.

The sensor device 10 and the mobile application 2 can establish and maintain a connection (e.g., connection 4B) for communications. For example, the mobile device executing the mobile application 2 and the sensor device 10 can establish a Bluetooth connection or an NFC connection. It is contemplated that the sensor device 10 can be connected to the mobile device via a wired connection. In some embodiments, the sensor device 10 communicates with the mobile device via the neuromodulation device 1. For example, the sensor device 10 can transmit packets to the neuromodulation device 1, which forwards the packets to the mobile application 2. In some embodiments, the sensor device 10 communicates with the neuromodulation device 1 via the mobile device. For example, the sensor device 10 can transmit packets to the mobile device, which forwards the packets to the neuromodulation device 1. Such communications via an intermediary device can be beneficial when one of the devices is unavailable (e.g., too far away) for a direct connection.

The sensor device 10 can include sensing electrodes 14A and 14B to be attached to the patient's toe. The sensing electrodes 14A and 14B can be a pair of electrodes such that sensing electrode 14A is the negative (−) terminal and the sensing electrode 14B is the positive (+) terminal. The sensor device 10 can detect electrical signals via the electrodes coupled to the patient. The sensor device 10 can detect the frequency and amplitude of the electrical signals. The sensor device 10 can generate packets identifying the detected frequency and amplitude of the electric signals. The sensor device 10 can transmit the packets to the mobile application 2 or the neuromodulation device 1 via the connection.

The sensor device 10 can include a pulse oximeter for measuring oxygen concentration of the patient. The pulse oximeter can include a red LED 16 and an infra-red LED 18 that faces a photo sensor 20. The pulse oximeter can cause the red LED 16 to emit red light (e.g., wavelength of 660 nm), and the infra-red LED 18 to emit infra-red light (e.g., wavelength of 940 nm). The absorption of light at these wavelengths differs between blood loaded with oxygen and blood lacking oxygen: oxygenated blood absorbs infrared light and allows red light to pass whereas deoxygenated blood allows infrared light to pass through while absorbing red light. The pulse oximeter can cause the photo sensor 20 to measure the light that is passed through the patient's blood. Based on the light measurements, the pulse oximeter can distinguish oxyhemoglobin to calculate the oxygen concentration of the patient. The pulse oximeter can identify pulse sequences in the light measurements to identify the pulse of the patient. The sensor device 10 can generate packets identifying the calculated oxygen concentration and pulse. For example, the sensor device 10 can generate packets identifying an oxygen concentration of 99% and a pulse of 65 BPM. The sensor device 10 can transmit the packets via the connection to the mobile application 2 or the neuromodulation device 1.

The sensor device 10 can include an accelerometer 22 for measuring acceleration to detect movements of the patient. For example, the accelerometer can be a micro-electro-mechanical system (MEMS). The sensor device 10 can use the accelerometer to detect movements of the patient. For example, the sensor device 10 can use the accelerometer to detect a motor response such as toe movements caused by tingling or tickling sensations from neuromodulation. The sensor device 10 can generate packets identifying the detected movements. For example, the sensor device 10 can generate packets identifying that the patient moved their toe towards the leg. The sensor device 10 can transmit the packets via the connection. The sensor device 10 can transmit the packets via the connection to the mobile application 2 or the neuromodulation device 1.

The method can include identifying if differences between sensor measurements and baseline measurements satisfy thresholds (STEP 354). The neuromodulation device 1 or the mobile application 2 can identify or verify proper placement of the neuromodulation device 1 based on the measurements generated by the sensor device 10. The neuromodulation device 1 or the mobile application 2 can receive the packets that include the measurements from the electrodes, accelerometer, and pulse oximeter of the sensor device 10. The neuromodulation device 1 or the mobile application 2 can identify the frequency and amplitude values, movement values, pulse value, and oxygen concentration of the patient 6 from the measurements in the packets. The neuromodulation device 1 or the mobile application 2 can identify or verify proper placement if the measurements indicate that the patient 6 is moving their toe or if the electrical frequency and amplitude, pulse, or oxygen concentration are elevated.

The neuromodulation device 1 or the mobile application 2 can maintain threshold values indicative of proper placement of the neuromodulation device 1. The mobile application 2 can maintain a threshold oxygen concentration, threshold pulse value, threshold movement values, or a threshold frequency and threshold amplitude that indicate that the neuromodulation device 1 is properly positioned on the patient to provide neuromodulation. For example, the threshold movement values can be indicative of movements caused by tingling or tickling caused by a neuromodulation device 1 that is properly positioned on the patient. In another example, the threshold oxygen concentration can be indicative of increased oxygen concentration caused by a neuromodulation device 1 that is properly positioned on the patient. In another example, the threshold pulse value can be indicative of increased pulse caused by a neuromodulation device 1 that is properly positioned. In another example, the threshold frequency and amplitude value can be indicative of the frequency and amplitude of electrical signals (e.g., treatment current) output by the neuromodulation device 1. In some embodiments, the threshold amplitude value can be indicative of the amplitude of electrical signals (e.g., treatment current) output by the neuromodulation device 1. In some embodiments, the mobile application 2 can receive, from the neuromodulation device 1, the frequency and amplitude of the treatment current applied by the neuromodulation device 1 to the patient. In some embodiments, the mobile application 2 can store the frequency and amplitude of the treatment current applied by the neuromodulation device 1 to the patient. In some embodiments, the mobile application 2 can identify (e.g., from a stored lookup table) the frequency and amplitude of the treatment current based on the treatment current selected by the patient via the mobile application 2.

The neuromodulation device 1, the mobile application 2, or the web service 3 can modify or update the threshold values. The mobile application 2 or the web service 3 can receive updates to the threshold values. In some embodiments, the neuromodulation device 1 or the mobile application 2 can receive the updates from the web service 3. In some embodiments, the neuromodulation device 1, the mobile application 2, or the web service 3 can receive the updates via selections made by the patient on the mobile application 2. In some embodiments, the mobile application 2 or the web service 3 can generate the updates based on historical measurements. The mobile application 2 or the web service 3 can use machine learning or artificial learning techniques to update or modify the threshold values. For example, the mobile application 2 or the web service 3 can identify that the patient has a lower-than-average increase in oxygen concentration level caused by neuromodulation, and the mobile application 2 or the web service 3 can decrease the threshold oxygen concentration level accordingly.

In some embodiments, the measured movement values might be caused by the patient 6 moving around or walking around. To avoid falsely classifying walking movements as tingling caused by neuromodulation, the neuromodulation device 1 or the mobile application 2 can compare movements of the toe (e.g., likely caused by neuromodulation) to the movements of the leg (e.g., likely caused by the patient 6 moving around).

The neuromodulation device 1 or the mobile application 2 can compare movement measurements generated by the accelerometer 22 of the sensor device 10 and movement measurements generated by the accelerometer 71 of the neuromodulation device 1. The neuromodulation device 1 or the mobile application 2 can receive, from the sensor device 10, the movement measurements generated by the accelerometer 22. In some embodiments, the sensor device 10 can transmit the movement measurements generated by the accelerometer 22 to the neuromodulation device 1. The neuromodulation device 1 can forward the movement measurements generated by the accelerometer 22 to the mobile application 2. In some embodiments, the neuromodulation device 1 can transmit the movement measurements generated by the accelerometer 71 to the mobile application 2. In some embodiments, the mobile application 2 can receive, from the neuromodulation device 1 or the sensor device 10, the movement measurements generated by the accelerometer 22. In some embodiments, the mobile application 2 can receive, from the neuromodulation device 1, the movement measurements generated by the accelerometer 71.

If the differences exceed the thresholds, the method can verify proper placement of the neuromodulation device 1 (STEP 356). The neuromodulation device 1 or the mobile application 2 can compare the movement measurements from the accelerometer 22 and the accelerometer 71. If the difference between both movement measurements is less than a threshold (e.g., the movements are similar since the patient 6 is moving their leg and thus their toe), then the neuromodulation device 1 or the mobile application 2 can generate a request for the patient 6 to keep their leg still for the measurement of their toe movements to be more accurate. If the neuromodulation device 1 generated the comparison, then the neuromodulation device 1 can transmit the comparison to the mobile application 2 or the web service 3. The mobile application 2 can receive the request and generate an interface requesting the patient 6 to keep their leg still for the measurement of their toe movements to be more accurate. If the mobile application 2 generated the comparison, then the mobile application 2 can generate an interface to request the patient 6 to keep their leg still for the measurement of their toe movements to be more accurate. In some embodiments, the mobile application 2 can transmit, to the web service 3, an indication that the interface was generated.

The neuromodulation device 1 or the mobile application 2 can identify or verify proper placement of the neuromodulation device 1 by identifying that the received measurements satisfy the threshold values. The neuromodulation device 1 or the mobile application 2 can identify that the measured movement values satisfy the threshold movement values by comparing the measured movement values and the threshold movement values. For example, the mobile application 2 can identify that measured movements caused by tickling or tingling sensations satisfy the threshold movement values. The mobile application 2 can identify that the measured oxygen concentration satisfies the threshold oxygen concentration by comparing the measured oxygen concentration and the threshold oxygen concentration. For example, the mobile application 2 can identify that a measured oxygen concentration that is elevated due to increased oxygen saturation in the blood satisfies the threshold oxygen concentration. The mobile application 2 can identify that the measured pulse value satisfies the threshold pulse value by comparing the measured pulse value and the threshold pulse value. For example, the mobile application 2 can identify that a measured pulse value that is elevated due to increased blood flow satisfies the threshold pulse value. The mobile application 2 can compare the measured frequency and amplitude values to the frequency and amplitude of the treatment current applied by the neuromodulation device 1 to the patient. The mobile application 2 can identify, based on the comparison, that the measured frequency and amplitude values are within a threshold frequency and amplitude value of the frequency and amplitude of the treatment current applied by the neuromodulation device 1 to the patient.

The mobile application 2 can identify or verify proper placement of the neuromodulation device 1 responsive to identifying that several of the received measurements satisfy the threshold values. For example, the mobile application 2 can identify or verify proper placement of the neuromodulation device 1 responsive to identifying that both the measured oxygen concentration and measured pulse value satisfy the threshold oxygen concentration and threshold pulse value. In another example, the mobile application 2 can identify or verify proper placement of the neuromodulation device 1 responsive to identifying that the measured oxygen concentration, measured pulse value, measured movement values, and measured voltage values all satisfy their respective thresholds.

The web service 3 can identify or verify proper placement of the neuromodulation device 1 by identifying that the measurements received from the neuromodulation device 1 satisfy the threshold values. The mobile application 2 can transmit the received measurements to the web service 3. The web service 3 can receive the measurements and compare them to the threshold values to identify or verify proper placement of the neuromodulation device 1.

If the differences do not exceed the thresholds, the method can identify improper placement of the neuromodulation device 1 (STEP 358). In some embodiments, the neuromodulation device 1, mobile application 2, or the web service 3 can set a flag indicating that the neuromodulation device 1 is not properly positioned if the difference between both movement measurements is less than the threshold.

In some embodiments, the nerve threshold is based on the measurements from the sensor device 10 and the feedback electrodes 43. In some embodiments, the neuromodulation device 1, mobile application 2, or the web services 3 identifies the nerve threshold based on the measurements from the sensor device 10. In some embodiments, the neuromodulation device 1, mobile application 2, or the web services 3 can identify the changing sensitivity based on the measurements from the sensor device 10 satisfying their respective measurement thresholds. For example, as described herein, the measurements from the sensor device 10 can indicate when the toe of the patient 6 starts moving. The neuromodulation device 1, mobile application 2, or the web services 3 can update the nerve threshold to the treatment current at which measurements from the sensor device 10 indicate that the patient 6 is moving their toe in a tickling movement.

The mobile application 2 or the web service 3 can use the nerve threshold to generate treatment schedules for the patient 6. The neuromodulation device 1, mobile application 2, or the web services 3 can identify changes in the nerve threshold to optimize the treatment schedules and treatment current. For example, the patient 6 can become more sensitive to neuromodulation over time and the nerve threshold would decrease, so the neuromodulation device 1 could apply less treatment current. In another example, the patient 6 can become less sensitive to neuromodulation over time and the nerve threshold would increase, so the neuromodulation device 1 could apply increased treatment current.

The web service 3 can use the nerve threshold to modify the treatment protocol regarding session duration and the time interval set between sessions. For example, by measuring it for each patient 6, the web service 3 can identify that a patient A benefits from neuromodulation best, if he/she gets a 20-minute session followed by a 10-minute break then another 20 minutes of neuromodulation. Another change might be about the time between 2 sessions. For example, for a patient A this period may be 2 days (because their nerve's threshold level is returning to rest level in 2 days-time) but for a patient B it might be 4 days. The web service 3 can generate individualized treatment protocols based on each patient's specific assessment, data from the neuromodulation device 1, sensor device 10, urinary diary, or feedback electrodes.

Figure 29:
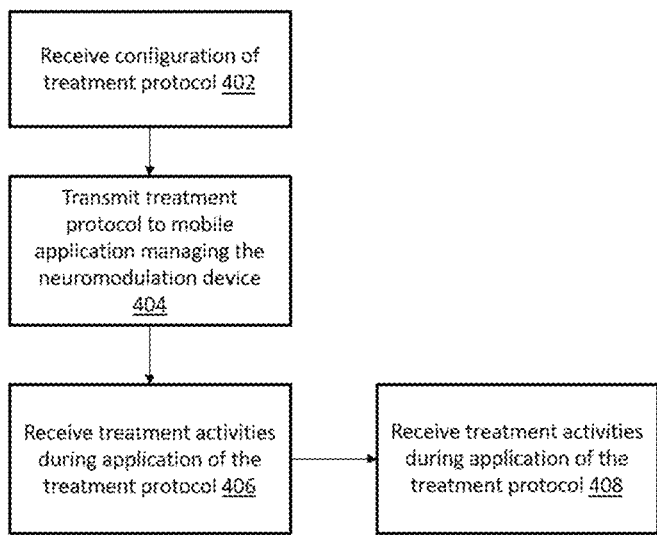
FIG. 29 is a flowchart of a method for administering neuromodulation.

FIG. 29 is a flowchart of a method for administering neuromodulation. The method can include receiving configuration of a treatment protocol (STEP 402). FIG. 16 depicts an interface displayed by the web application 5 for the healthcare provider 7 to configure treatment for the patient 6. The web service 3 can manage the registration of the patient 6, the registration of the neuromodulation device 1, the remote treatment, and the information input and displayed by the web application 5. The web service 3 can cause the web application 5 to display a login screen for the healthcare provider 7. In some embodiments, the web service 3 can receive, from the healthcare professional 7 via the login screen displayed by the web application 5, the identifier number and the password assigned to the healthcare professional 7.

FIG. 17 depicts an interface displayed by the web application 5 for the healthcare provider 7 to manage treatment for the patient 6. In some embodiments, after validating the identifier and password, the web service 3 can cause the web application 5 to display the interface shown in FIG. 17.

FIG. 18 depicts an interface displayed by the web application 5 for the healthcare provider 7 to configure treatment for the patient 6. The web service 3 can receive patient information provided by the healthcare professional 7 into the web application 5. The web service 3 can store or maintain the patient information provided by the healthcare professional 7 into the web application 5.

FIG. 19 depicts an interface displayed by the web application 5 for the healthcare provider 7 to view information about the patient 6. The web service 3 can transmit the information to the web application 5 for display to the healthcare professional 7.

FIG. 20 depicts an interface displayed by the web application 5 for the healthcare provider 7 to view treatments available to assign to the patient 6. FIG. 20 depicts an interface displayed by the web application 5 for the healthcare provider 7 to configure a treatment for the patient 6. The web service 3 can receive, from the healthcare provider 7 via the web application 5, parameters of the treatment protocol such as duration, pulse width and frequency values. For example, the web service 3 can receive a treatment protocol that defines treatment current (e.g., 0-60 mA), pulse width (e.g., 40-400 us), frequency (e.g., 1-50 Hz), duration of each treatment session (e.g., 0-30 minutes), or total treatment duration and treatment intervals (e.g., 1-12 weeks, 1 to 7 times per week, etc.). FIG. 21 shows example reference values for the parameters of the treatment protocol of urinary incontinence such as a treatment duration of 12 sessions in total, applied once or a week, for a session duration of 15 minutes, a pulse width of 200 us, and a pulse frequency of 20 Hz.

The method can include transmitting the treatment protocol to the mobile application 2 managing the neuromodulation device 1 (STEP 404). FIG. 22 depicts an interface displayed by the web application 5 for the healthcare provider 7 to view treatments assigned to the patient 6. FIG. 23 depicts an interface displayed by the web application 5 for the healthcare provider 7 to accept an assigned treatment for the patient 6. The web service 3 can transmit the treatment parameters (e.g., schedule, treatment duration, frequency, pulse width, etc.) of the assigned treatment to the neuromodulation device 1 or the mobile application 2 of the patient 6. The web service 3 can provide the treatment to the mobile application 2 for configuring the neuromodulation device 1 to provide treatment to the patient 6 at home without making any additional protocol adjustments. For example, the neuromodulation device 1 can apply mono phasic current pulses up to 60 mA (60 V at 1000-ohm load) for neuromodulation. In some embodiments, the web service 3 controls the neuromodulation device 1 by transmitting the treatment protocol assigned by the healthcare provider 7 via mobile application 2 to the neuromodulation device 1. In some embodiments, the web service 3 controls the mobile application 2 by managing which notification can be sent and when. In some embodiments, the web service 3 transmits notifications (such as e-mails, SMS, etc.) to the healthcare provider 7 regarding the efficacy and details of the treatment.

FIG. 24 depicts an interface displayed by the web application 5 for the healthcare provider 7 to view a schedule of the treatment assigned to the patient 6. The web service 3 can receive treatments assigned by the healthcare professional 7 from the web application 5.

The method can include receiving treatment activities during the treatment protocol (STEP 406). FIG. 25 depicts an interface displayed by the web application 5 for the healthcare provider 7 to view treatment activities associated with the treatment assigned to the patient 6. The web service 3 receives the treatment activities from the neuromodulation device 1 or the mobile application 2. The web service 3 receives treatment activities identified by the neuromodulation device 1 (e.g., location, current, frequency, pulse width, electrical resistance, voltage, mobility, etc.) and treatment activities provided by the patient 6 via the mobile application 2 (e.g., answers to urinary diary or questionnaire). The web service 3 can maintain or store the treatment activities and related functions and in a database. The entered data of the patient 6, and the data from the neuromodulation device 1 after treatment can be stored in the database.

The web service 3 can identify the location of the patient 6 to refine the treatment assessments by prompting the patient 6 to enter more accurate data into their urinary diary and to prompt the patient 6 for self-monitoring of their treatment to increase patient 6 awareness and enhance treatment success. Based on the location of the patient 6, the web service 3 can transmit notifications (e.g., reminders, push notifications, or gamification feedback) to the mobile application 2 for display. The notifications can remind the patient 6 to consume fluids or indicate voiding by the patient 6 (e.g., emptying the bladder and/or the bowls).

For example, if the location identified by the web service 3 indicates that the patient 6 is in a kitchen, then the patient 6 might be drinking fluids. To verify that patient accurately reports their fluid intake into their urinary diary, the web service 3 can transmit a notification to the mobile application 2 to prompt the patient 6 to describe any fluid intake. In another example, if the location identified by the web service 3 indicates that the patient 6 visits the restroom, the web service 3 can improve the tracking process and accuracy of the urinary diary by transmitting questions to the mobile application 2 about whether the patient 6 has urinated.

By means of the positioning devices 83-86 used, depending on the transition and stay times between the tracker device 87, the positioning device coverage area 89-92 inside the house and networks thereof, the web service 3 can identify the location of the patient 6. The web service 3 can communicate with the positioning devices 83-86 and the tracker device 87 to receive location-based treatment activities to identify a location of the mobile application 2 or the tracker device 87 to identify a location of the patient 6. The web service 3 can receive location information from each of the positioning devices 83-86 and the tracker device 87. Based on the received location information, the web service 3 can determine the location of the tracker device 87 and thus the patient 6. In some embodiments, the web service 3 can communicate with the tracker device 87 to identify the location of the patient 6 to continue receiving accurate location information if the patient 6 leaves their mobile device and moves to different locations.

The method can include transmitting an updated treatment protocol based on analysis of the treatment activities (STEP 408). Since the healthcare personnel can remotely monitor all treatment sessions and treatment efficacy, the patient 6 can continue their treatment at home with the applications included in the neuromodulation device 1 without going to the hospital. The patient 56 can use a mobile device such as a smartphone to execute the mobile application 2 to connect to the neuromodulation device 1 via a wired or wireless connection (e.g., Bluetooth connection) for the patient 6 to manage the treatment process in accordance with the associated audible and visual instructions.

The web service 3 can analyze the treatment activities, which can improve and strengthen the effect of the actual treatment, which can be effective especially in overactive bladder, and minimizing the nocebo effect. By providing a personalized treatment experience with the treatment activities collected, the systems and methods described herein provide outputs about the effectiveness and potential of the standard treatment periods.

During the treatment, the web service 3 receives treatment activities in a schedule planned by the healthcare provider 7 and transmits it to the mobile application 2 and neuromodulation device 1. The web service 3 enables the neuromodulation device 1 to be tracked by the patient 6 with the visual and audible notifier that indicates that the treatment has started and continues. If the treatment is disrupted and not performed as planned, or the instructions are not followed, then the web service 3 provides a notification feedback for the healthcare provider 7. The web service 3 can receive data describing the use of the neuromodulation device 1 by the patient 6, the intermittent feedbacks with the urinary diary and validated questionnaires contained therein. The web service 3 can transmit the data and the information in reports about the treatments to the web application 5 for viewing by the healthcare provider 7. The healthcare provider 7 can analyze the treatment activities to optimize the treatment protocol to minimize the problem of dropout of the treatment. For obtaining the urinary diaries, the use of indoor positioning device that support correct input of records, especially in case of elderly patients, increases the effect of the feedbacks. The patient 6 knowing that their treatment is monitored by the healthcare provider 7 has the effect of strengthening placebo effect and minimizing nocebo effect.

As a result of the data collected about the treatment, the web service 3 can calculate derived results to primarily monitor the effectiveness of the treatment. Example types of treatment success data are derived to monitor treatment success include success in continuing the treatment and success of treatment. The success of the treatment can be classified as complete recovery, partial and unsuccessful according to the numerical results obtained from the validated questionnaires. The success of continuing the treatment can be measured based on patient's adherence to a treatment calendar. This can be scored from 1 (unsuccessful) to 4 (completely successful). During the total treatment period, the cumulative delay can be scored 4 points if it is between 0-6 days, 3 points between 7-13 days, 2 points between 14-20 days, and 1 point if it is more than 21 days. The mobile application 2 can notify the patient 6 about the success of the treatment, gives points by gamifying the treatment, and increases adherence to the treatment.

The web service 3 can measure treatment success as field-value pairs (e.g., points/scores) based on the result of validated questionnaires conducted at the beginning, middle, and end of the treatment calendar. The web service 3 can display the measurements to the healthcare provider 7 via the web application 5.

The web service 3 can maintain a reference score as baseline reference for treatment success. For example, the web service 3 can generate the reference score after the first assessment done at the beginning of the treatment. The assessment can be repeated at the middle and at the end of treatment, and the scores obtained at the middle and end can be compared to the reference score that was obtained at the beginning of treatment. The web service 3 can address the assessment by verifying if the patient 6 complied with the treatment protocol (e.g., did the patient 6 get their session as scheduled and as many as scheduled) by checking the consistency of treatment current (did the patient 6 apply a consistent treatment current throughout sessions or did the patient vary the treatment current by an interval exceeding a threshold). If the problems occur due non-compliance or wrong administration by the patient 6, then the web service 3 can transmit notifications to the mobile application 2. If the problems occur for other reasons, then the healthcare provider 7 can assign a new treatment protocol via the web application 5.

The web service 3 can generate or assign classifications or categories to the treatment assessments. For example, the web service 3 can categorize the treatment assessment into 3 categories according to the score intervals, as "successful" (cured), "partial" (improvement) and "unsuccessful". The web service 3 can use the OAB-V8 (which is a patient reported outcome questionnaire used to screen for OAB and measures symptom bother) to assign the classifications or categories. For example, if the patient's score is 8 or higher at the beginning of the treatment, and the score is found less than 8 at the middle or end of treatment, the web service 3 can assign "cure". If at the end, the patient's score is between the beginning score and 8, the web service 3 can assign "improvement". If the score at the end is higher than 8, the web service 3 can assign "unsuccessful". For a similar assessment, the web service 3 can assess the urinary diary (e.g., tool to assess symptoms of OAB and provides wider information than OAB-V8) to assign "cure", "improvement", or "unsuccessful". For example, in response to identifying a reduction by half or more in all baseline symptoms, the web service 3 can assign "improvement" to replace previously assigned "unsuccessful."

The web service 3 can generate recommendations and analysis based on the treatment activities to increase adherence to treatment with sustainable, updatable, and digital patient navigation. The web service 3 can detect or identify problems related to applying the treatment (e.g., significant change at the level of the current applied at a session compared to previous sessions, or problems related to session intervals, or session duration). The web service 3 can communicate the problems by transmitting them to the mobile application 2. Data related to such problems is detected by mobile application 2 and communicated to the patient and healthcare provider 7 via the web service 3, using e-mail, or text, or other similar notifications. The web service 3 advantageously ensures that the treatment progresses correctly.

Treatment problems can relate to patient error selecting a treatment current. For example, the patient 6 might fail to adjust the treatment current at the beginning of each session based on their motor response and/or sensory response at each time (since it can be different at each time). The web service 3 can receive the measurements generated by the neuromodulation device 1 and select the treatment current set by the patient 6 based on the measurements. For example, the web service 3 can adjust the treatment current to a comfortable level for the patient 6 based on the oxygen concentration, leg movements, or electrical feedback of the patient's nerve. The web service 3 can further adjust the treatment current based on the patient's selections via the mobile application 2. The web service 3 can transmit the adjusted treatment current to the mobile application 2 for display and confirmation by the patient 6.

Treatment problems can relate to failure of the patient 6 to comply with the treatment calendar and/or session duration. To remedy this problem, the web service 3 can transmit calendar notifications to the mobile application 2 to alert the patient 6. If the web service 3 fails to receive information that the neuromodulation device 1 was activated according to schedule after the notifications (e.g., patient 6 still misses scheduled sessions or cuts the sessions short, etc.), the web service 3 can transmit notifications to the web application to notify the healthcare provider 7. The web application can display information about the neuromodulation device 1 usage and notifications displayed by the mobile application 2 for the healthcare provider 7 to identify reasons of treatment failure/success based-on data.

The web service 3 can receive, via the web application, the diagnosis confirmed by the healthcare provider 7 (via a provided checklist) interacting with the web application. The web service 3 can receive the checklist from the healthcare provider 7. The web service 3 can prompt the web application to require the healthcare provider 7 to fill this checklist during the registration of the patient 6. The checklist can include criteria relating to proven infection or other obvious pathology (such as bladder stone, tumor). For example, overactive bladder syndrome (OAB) is characterized by urinary urgency, with or without urgency urinary incontinence, usually with increased daytime frequency and nocturia, if there is no proven infection or other obvious pathology (such as bladder stone, tumor). The web service 3 can maintain or store the checklist. By storing the checklist, if the patient 6 changes their healthcare provider, the new healthcare provider can access the checklist and associated information. The web service 3 can provide the checklist to the web application for display to the healthcare provider 7 for confirmation or analysis.

The web service 3 can increase adherence to treatment and success of treatment by updating session intervals (once a week, twice a week, etc.), treatment duration (6 weeks, 12 weeks). The web service 3 can maintain or store information related to patient history (including all diagnostic tests, the treatments they are getting, other diseases, and such) to ensure that another healthcare provider 7 can continue treating the patient 6. The web service 3 can apply machine learning or artificial intelligence (e.g., big data) to identify session intervals, session duration, and other patterns or common factors responsive for treatment failure or success. At the beginning of the treatment, the web service 3 can transmit information to the mobile application 2 to inform the patient 6 about the features that increase adherence to treatment to result in a more attentive use of such features by the patient 6. By generating an individual treatment plan (e.g., "individualization of the treatment"), the web service 3 can provide remote monitoring and assessment to increase the patient's adherence to the treatment calendar of which they are made a part of. The web service 3 and mobile application 2 enable ease of monitoring, assessing, and intervention for the healthcare provider 7 to increase their motivation for successfully treating the patient 6. This ease can increase both adherence of the patient 6 and healthcare provider 7 to the treatment.

The data recorded in the database in the web service 3 constitutes the source for analysis of treatment activities. For example, by monitoring the impedance in the treatment sessions, it can provide data on after how many treatments the hydrogel has completed its life, and how often it needs to be changed. The web service 3 can parse protocols (which can include treatment duration (how many weeks long), session duration (how many minutes each session), interval (how apart each session), frequency (Hz), pulse width (microsecond), treatment current (mA)) to generate suggestions regarding which one is best suited for the patient 6 according to the treatment activities. In another example, the web service 3 can analyze, assess, or categorize unsuccessful results according to analysis of the treatment activities. Based on data collected regarding the patient history, patient compliance, the treatment, and treatment protocol, the web service 3 can use machine learning to generate suggested treatment protocols.

According to this data, the mobile application 2 sends notifications to the patient 6. If there is an unexpected impedance change, it reports whether the treatment is effective or not. If during the treatment session, an exceptional treatment current is applied, or impedance or device-related error codes occur, the healthcare provider 7 and or patient 6 are warned by notifications (e-mail, SMS, mobile application 2 notifications, etc.) created from the web service 3. Thus, the missing or incorrect treatment session can be reassigned by the healthcare provider 7 or the artificial intelligence engine. Such reassignments can also be made based on artificial intelligence without the healthcare provider 7.

Since the treatment protocol can be adjusted via the web application and the effects of potential different treatment protocol combinations on treatment can be measured, new treatment protocols that will be recommended to healthcare provider 7 can be created. The web service 3 can generate alternatives to the reference treatment protocols. For example, the web service 3 can generate new treatment protocols (session duration, interval, frequency, pulse width and such) to be studied at clinical trials, and those with successful results can be added to the learning algorithm of the treatment activities.

The web service 3 can optimize the treatment protocols. For example, instead of applying the treatment twice a week for 6 weeks, alternating legs every other day, the web service 3 can identify a treatment plan to increase the effectiveness of the treatment in less than 6 weeks. The web service 3 can generate such recommendations and inferences based on the treatment activities with the artificial intelligence engine operating in the background of the web service 3.

The web service 3 can receive and maintain data related to patient history, treatment compliance data for each patient 6, treatment current, treatment protocol data (pulse width, pulse frequency, session duration, session intervals, the leg used), treatment outcome data, data from the neuromodulation device 1 (both treatment related data and device related data), data from the sensor device 10. The web service 3 can apply machine learning algorithms to take this input data and generate output data that comprises potential treatment protocol suggestions for individualized treatment protocol options.

In some embodiments, the systems and methods described herein can implement a metaverse to provide remote treatment applications. In some embodiments, the system may include VR/AR glasses or headsets, feedback devices, and wearable, monitorable treatment systems that enable patients 6 and healthcare professionals 7 to be in one-to-one contact. The healthcare professionals 7 will be able to visit their patient 6 in a virtual environment and will be able to provide their suggestions, or vice versa. Health and treatment activities can provide more effective and sustainable treatments. In addition, the purchase of treatment devices can be made from a virtual market in the metaverse. For example, by a digital healthcare professional (without a real healthcare professional), the first diagnosis and registration of the patient will be made in a virtual examination. The patient 6 would pay with their digital wallet and be included in the treatment system. The neuromodulation device 1 and its peripheral equipment (beacons, positioning devices 83-86, tracker device 87, wristband, feedback devices) would be delivered to the patient's home by cargo. At initial applications, the digital assistant will describe the patient 6, by virtual reality glasses, how to place the neuromodulation device 1 and how to use the interface of the mobile application 2.

Section E: Example Computing/Network Architecture

Figure 30:
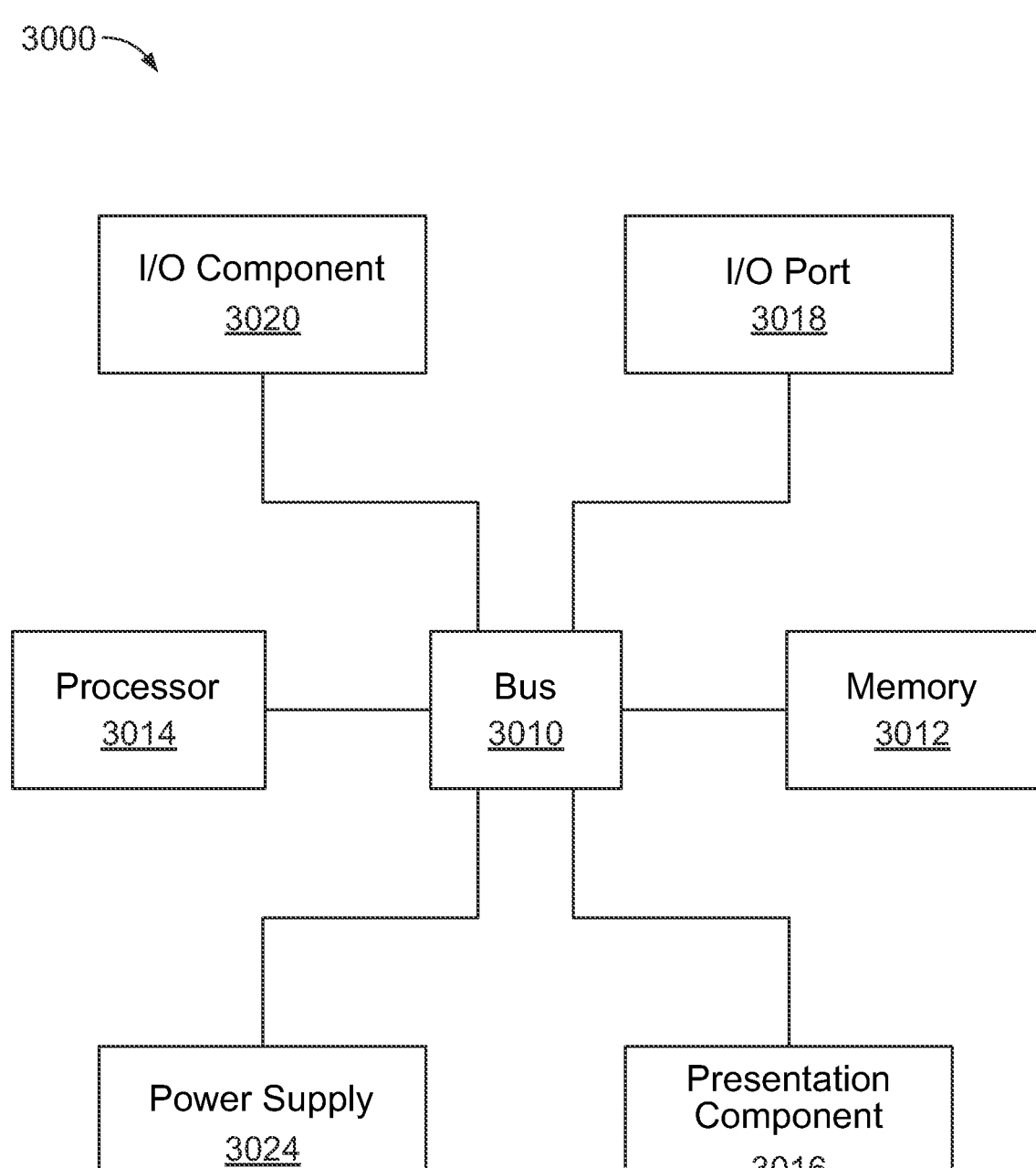
FIG. 30 is a diagrammatic illustration of a high-level architecture for implementing processes in accordance with aspects of embodiments of the present disclosure.

Any suitable computing device can be used to implement the computing devices and methods/functionality described herein and be converted to a specific system for performing the operations and features described herein through modification of hardware, software, and firmware, in a manner significantly more than mere execution of software on a generic computing device, as would be appreciated by those of skill in the art. One illustrative example of such a computing device 3000 is depicted in FIG. 30. The computing device 3000 is merely an illustrative example of a suitable computing environment and in no way limits the scope of the present disclosure. A "computing device," as represented by FIG. 30, can include a "workstation," a "server," a "laptop," a "desktop," a "hand-held device," a "mobile device," a "tablet computer," or other computing devices, as would be understood by those of skill in the art. Given that the computing device 3000 is depicted for illustrative purposes, embodiments of the present disclosure may utilize any number of computing devices 3000 in any number of different ways to implement a single embodiment of the present disclosure. Accordingly, embodiments of the present disclosure are not limited to a single computing device 3000, as would be appreciated by one with skill in the art, nor are they limited to a single type of implementation or configuration of the example computing device 3000.

The computing device 3000 can include a bus 3010 that can be coupled to one or more of the following illustrative components, directly or indirectly: a memory 3012, one or more processors 3014, one or more presentation components 3016, input/output ports 30130, input/output components 3020, and a power supply 3024. One of skill in the art will appreciate that the bus 3010 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 30 is merely illustrative of an exemplary computing device that can be used to implement one or more embodiments of the present disclosure, and in no way limits the disclosure.

The computing device 3000 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CD-ROM, digital versatile disks (DVD) or other optical or holographic media; magnetic cassettes, magnetic tape, magnetic disk storage or other magnetic storage devices that can be used to encode information and can be accessed by the computing device 3000.

The memory 3012 can include computer-storage media in the form of volatile and/or nonvolatile memory. The memory 3012 may be removable, non-removable, or any combination thereof. Exemplary hardware devices are devices such as hard drives, solid-state memory, optical-disc drives, and the like. The computing device 3000 can include one or more processors that read data from components such as the memory 3012, the various I/O components 3016, etc. Presentation component(s) 3016 present data indications to a user or other device. Exemplary presentation components include a display device, speaker, printing component, vibrating component, etc.

The I/O ports 3018 can enable the computing device 3000 to be logically coupled to other devices, such as I/O components 3020. Some of the I/O components 3020 can be built into the computing device 3000. Examples of such I/O components 3020 include a microphone, joystick, recording device, VR glasses, scanner, printer, wireless device, networking device, and the like.

Figure 31:
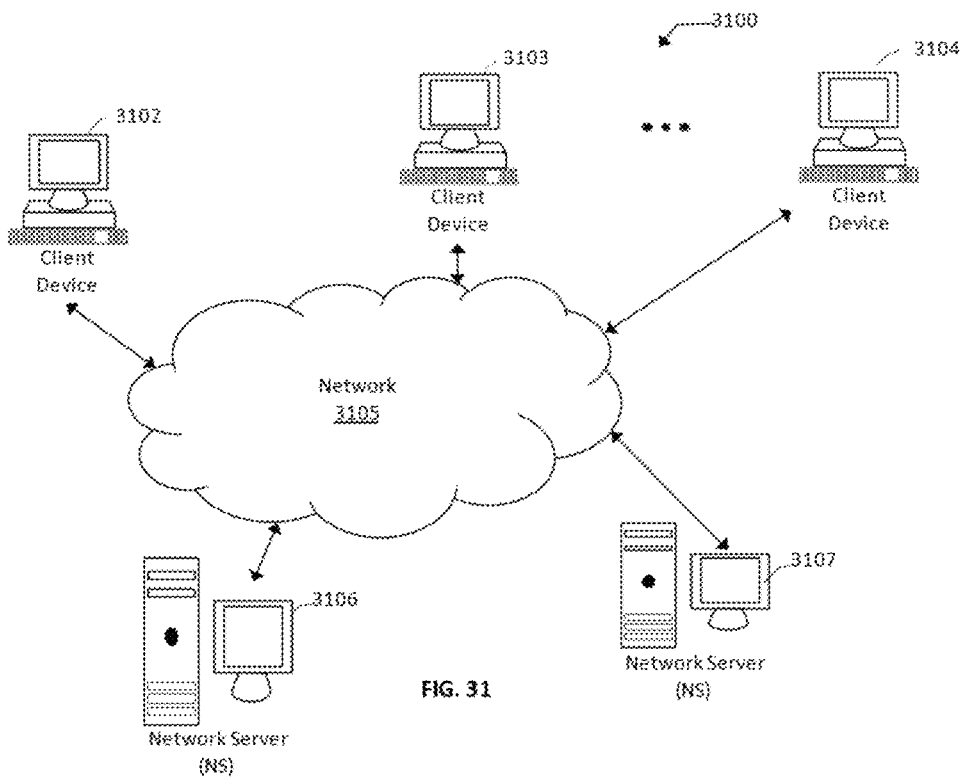
FIG. 31 is a diagrammatic illustration of a high-level connected systems architecture for implementing processes in accordance with aspects of the present disclosure.

FIG. 31 depicts a block diagram of an exemplary computer-based system and platform 3100 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 3100 may be configured to manage a large number of members and concurrent transactions, as detailed herein. In some embodiments, the exemplary computer-based system and platform 3100 may be based on a scalable computer and network architecture that incorporates varies strategies for assessing the data, caching, searching, and/or database connection pooling. An example of the scalable architecture is an architecture that is capable of operating multiple servers.

In some embodiments, referring to FIG. 31, member computing device 3102, member computing device 3103 through member computing device 3104 (e.g., clients) of the exemplary computer-based system and platform 3100 may include virtually any computing device capable of receiving and sending a message over a network (e.g., cloud network), such as network 3105, to and from another computing device, such as servers 3106 and 3107, each other, and the like. In some embodiments, the member devices 3102-3104 may be personal computers, multiprocessor systems, microprocessor-based or programmable consumer electronics, network PCs, and the like. In some embodiments, one or more member devices within member devices 3102-3104 may include computing devices that typically connect using a wireless communications medium such as cell phones, smart phones, pagers, walkie talkies, radio frequency (RF)

devices, infrared (IR) devices, citizens band radio, integrated devices combining one or more of the preceding devices, or virtually any mobile computing device, and the like. In some embodiments, one or more member devices within member devices 3102-3104 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMAX, CDMA, OFDM, OFDMA, LTE, satellite, ZigBee, etc.). In some embodiments, one or more member devices within member devices 3102-3104 may include may run one or more applications, such as Internet browsers, mobile applications, voice calls, video games, videoconferencing, and email, among others. In some embodiments, one or more member devices within member devices 3102-3104 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 3102-3104 may be specifically programmed by either Java, .Net, QT, C, C++, Python, PHP and/or other suitable programming language. In some embodiment of the device software, device control may be distributed between multiple standalone applications. In some embodiments, software components/applications can be updated and redeployed remotely as individual units or as a full software suite. In some embodiments, a member device may periodically report status or send alerts over text or email. In some embodiments, a member device may contain a data recorder which is remotely downloadable by the user using network protocols such as FTP, SSH, or other file transfer mechanisms. In some embodiments, a member device may provide several levels of user interface, for example, advance user, standard user. In some embodiments, one or more member devices within member devices 3102-3104 may be specifically programmed include or execute an application to perform a variety of possible tasks, such as, without limitation, messaging functionality, browsing, searching, playing, streaming, or displaying various forms of content, including locally stored or uploaded messages, images and/or video, and/or games.

In some embodiments, the exemplary network 3105 may provide network access, data transport and/or other services to any computing device coupled to it. In some embodiments, the exemplary network 3105 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 3105 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 3105 may include and implement, as an alternative or in conjunction with one or more of the above, a WiMAX architecture defined by the WiMAX forum. In some embodiments and, optionally, in combination of any embodiment described above or below, the exemplary network 3105 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 3105 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMAX, CDMA, OFDM, OFDMA, LTE, satellite and any combination thereof. In some embodiments, the exemplary network 3105 may also include mass storage, such as network attached storage (NAS), a storage area network (SAN), a content delivery network (CDN) or other forms of computer or machine-readable media.

In some embodiments, the exemplary server 3106 or the exemplary server 3107 may be a web server (or a series of servers) running a network operating system, examples of which may include but are not limited to Apache on Linux or Microsoft IIS (Internet Information Services). In some embodiments, the exemplary server 3106 or the exemplary server 3107 may be used for and/or provide cloud and/or network computing. Although not shown in FIG. 31, in some embodiments, the exemplary server 3106 or the exemplary server 3107 may have connections to external systems like email, SMS messaging, text messaging, ad content providers, etc. Any of the features of the exemplary server 3106 may be also implemented in the exemplary server 3107 and vice versa.

In some embodiments, one or more of the exemplary servers 3106 and 3107 may be specifically programmed to perform, in non-limiting example, as authentication servers, search servers, email servers, social networking services servers, Short Message Service (SMS) servers, Instant Messaging (IM) servers, Multimedia Messaging Service (MMS) servers, exchange servers, photo-sharing services servers or any similarly suitable service-base servers for users of the member computing devices 3101-3104.

In some embodiments and, optionally, in combination of any embodiment described above or below, for example, one or more exemplary computing member devices 3102-3104, the exemplary server 3106, and/or the exemplary server 3107 may include a specifically programmed software module that may be configured to send, process, and receive information using a scripting language, a remote procedure call, an email, a tweet, Short Message Service (SMS), Multimedia Message Service (MMS), instant messaging (IM), an application programming interface, Simple Object Access Protocol (SOAP) methods, Common Object Request Broker Architecture (CORBA), HTTP (Hypertext Transfer Protocol), REST (Representational State Transfer), SOAP (Simple Object Transfer Protocol), MLLP (Minimum Lower Layer Protocol), or any combination thereof. In some embodiments, the messages can be received on cell phone or tablet applications written to improve user experience.

Figure 32:
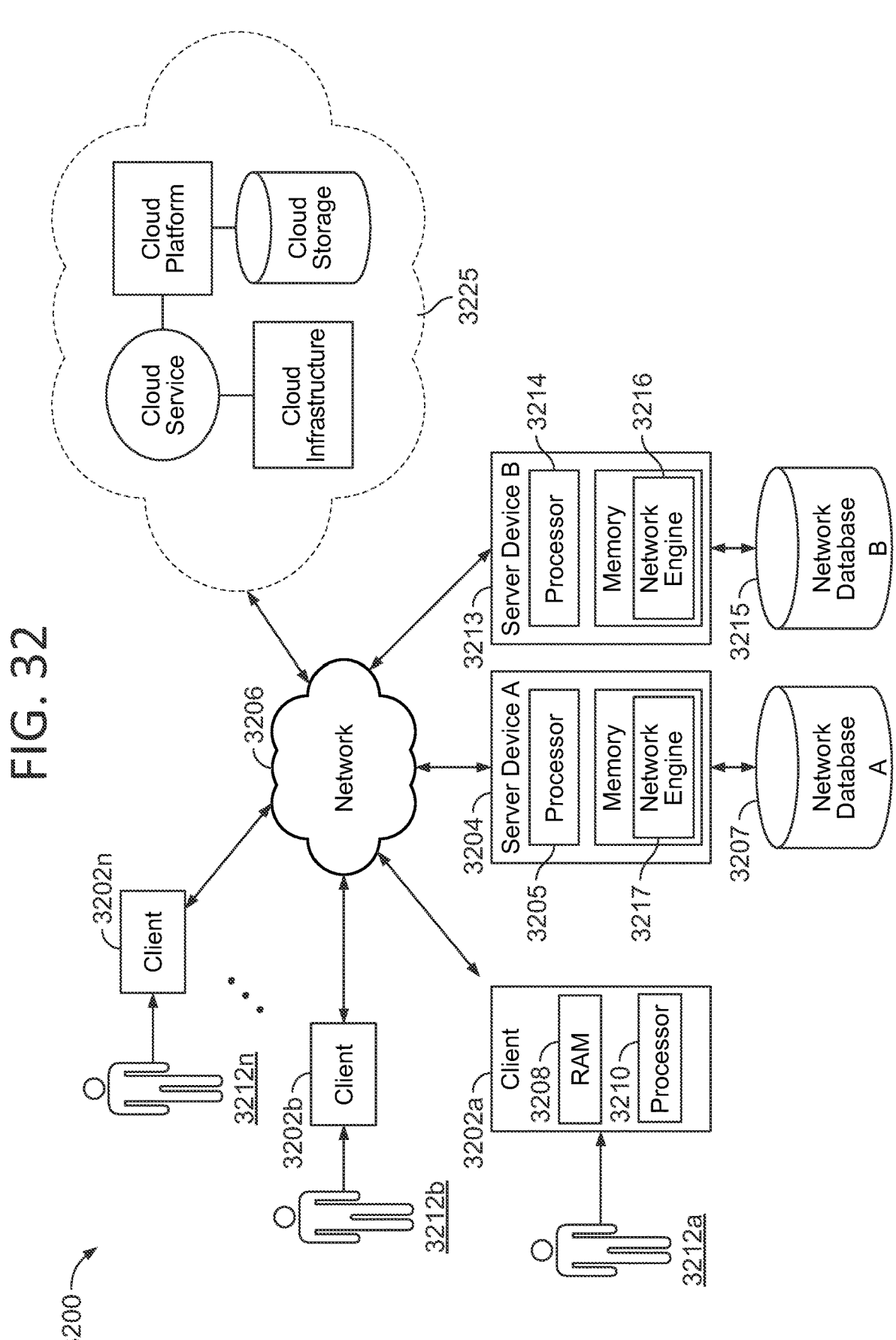
FIG. 32 is a diagrammatic illustration of another high-level connected systems architecture for implementing processes in accordance with aspects of the present disclosure.

FIG. 32 depicts a block diagram of another exemplary computer-based system and platform 3200 in accordance with one or more embodiments of the present disclosure.

However, not all of these components may be required to practice one or more embodiments, and variations in the arrangement and type of the components may be made without departing from the spirit or scope of various embodiments of the present disclosure. In some embodiments, the member computing device 3202a, member computing device 3202b through member computing device 3202n shown each at least includes a computer-readable medium, such as a random-access memory (RAM) 3208 coupled to a processor 3210 or FLASH memory. In some embodiments, the processor 3210 may execute computer-executable program instructions stored in memory 1008. In some embodiments, the processor 3210 may include a microprocessor, an ASIC, and/or a state machine. In some embodiments, the processor 3210 may include, or may be in communication with, media, for example computer-readable media, which stores instructions that, when executed by the processor 3210, may cause the processor 3210 to perform one or more steps described herein. In some embodiments, examples of computer-readable media may include, but are not limited to, an electronic, optical, magnetic, or other storage or transmission device capable of providing a processor, such as the processor 3210 of client 3202a, with computer-readable instructions. In some embodiments, other examples of suitable media may include, but are not limited to, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, PHP, HTML, JavaScript, and etc.

In some embodiments, member computing devices 3202a through 3202n may also comprise a number of external or internal devices such as a mouse, a CD-ROM, DVD, a physical or virtual keyboard, a display, or other input or output devices. In some embodiments, examples of member computing devices 3202a through 3202n (e.g., clients) may be any type of processor-based platforms that are connected to a network 3206 such as, without limitation, personal computers, digital assistants, personal digital assistants, smart phones, pagers, digital tablets, laptop computers, Internet appliances, and other processor-based devices. In some embodiments, member computing devices 3202a through 3202n may be specifically programmed with one or more application programs in accordance with one or more principles/methodologies detailed herein. In some embodiments, member computing devices 3202a through 3202n may operate on any operating system capable of supporting a browser or browser-enabled application, such as Microsoft™, Windows™, and/or Linux. In some embodiments, member computing devices 3202a through 3202n shown may include, for example, personal computers executing a browser application program such as Google Chrome browser, Internet Explorer™ or Edge, Apple Computer, Inc.'s Safari™, Mozilla Firefox, Opera, etc. In some embodiments, through the member computing client devices 3202a through 3202n, user 3212a, user 3212b through user 3212n, may communicate over the exemplary network 3206 with each other and/or with other systems and/or devices coupled to the network 3206. As shown in FIG. 32, exemplary server devices 3204 and 3213 may include processor

3205 and processor 3214, respectively, as well as memory 3217 and memory 3216, respectively. In some embodiments, the server devices 3204 and 3213 may be also coupled to the network 3206. In some embodiments, one or more member computing devices 3202a through 3202n may be mobile clients.

In some embodiments, at least one database of exemplary databases 3207 and 3215 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 33:
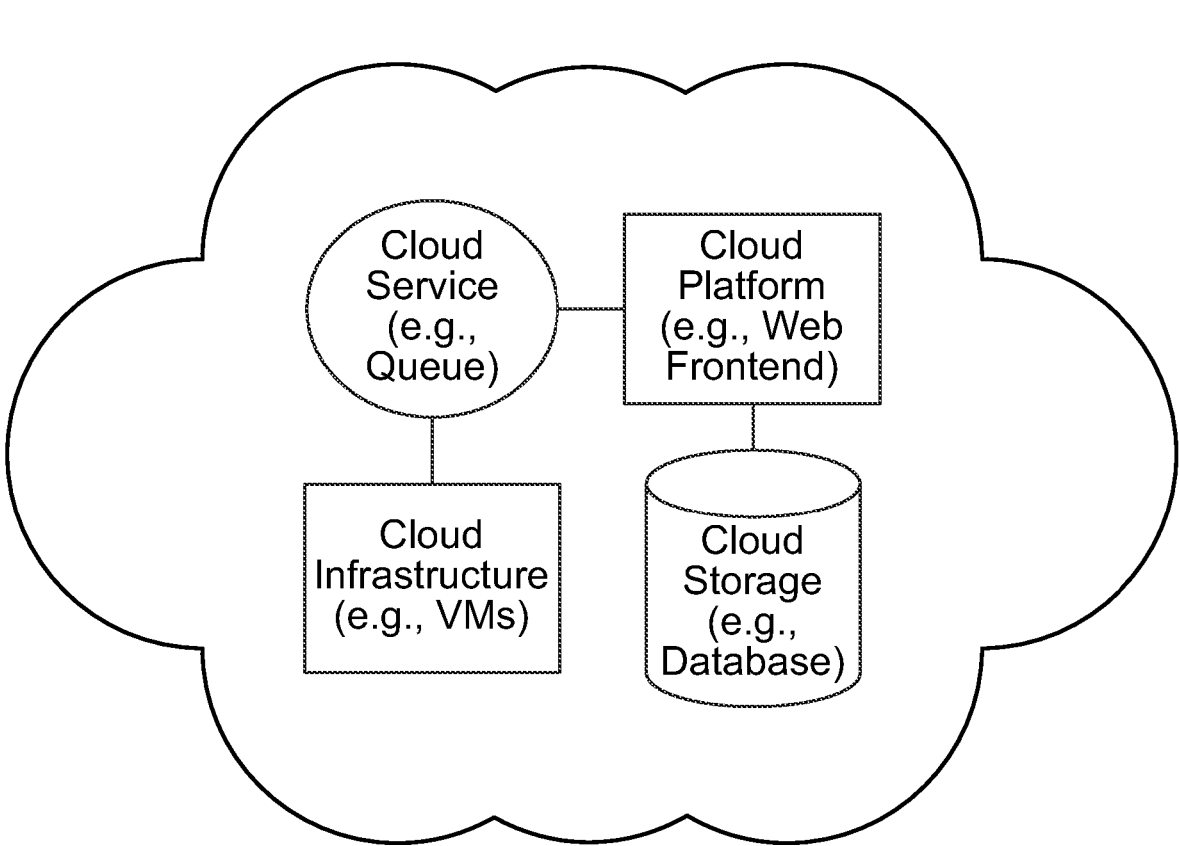
FIG. 33 is a diagrammatic illustration of another high-level connected systems architecture for implementing processes in accordance with aspects of the present disclosure.
Figure 34:
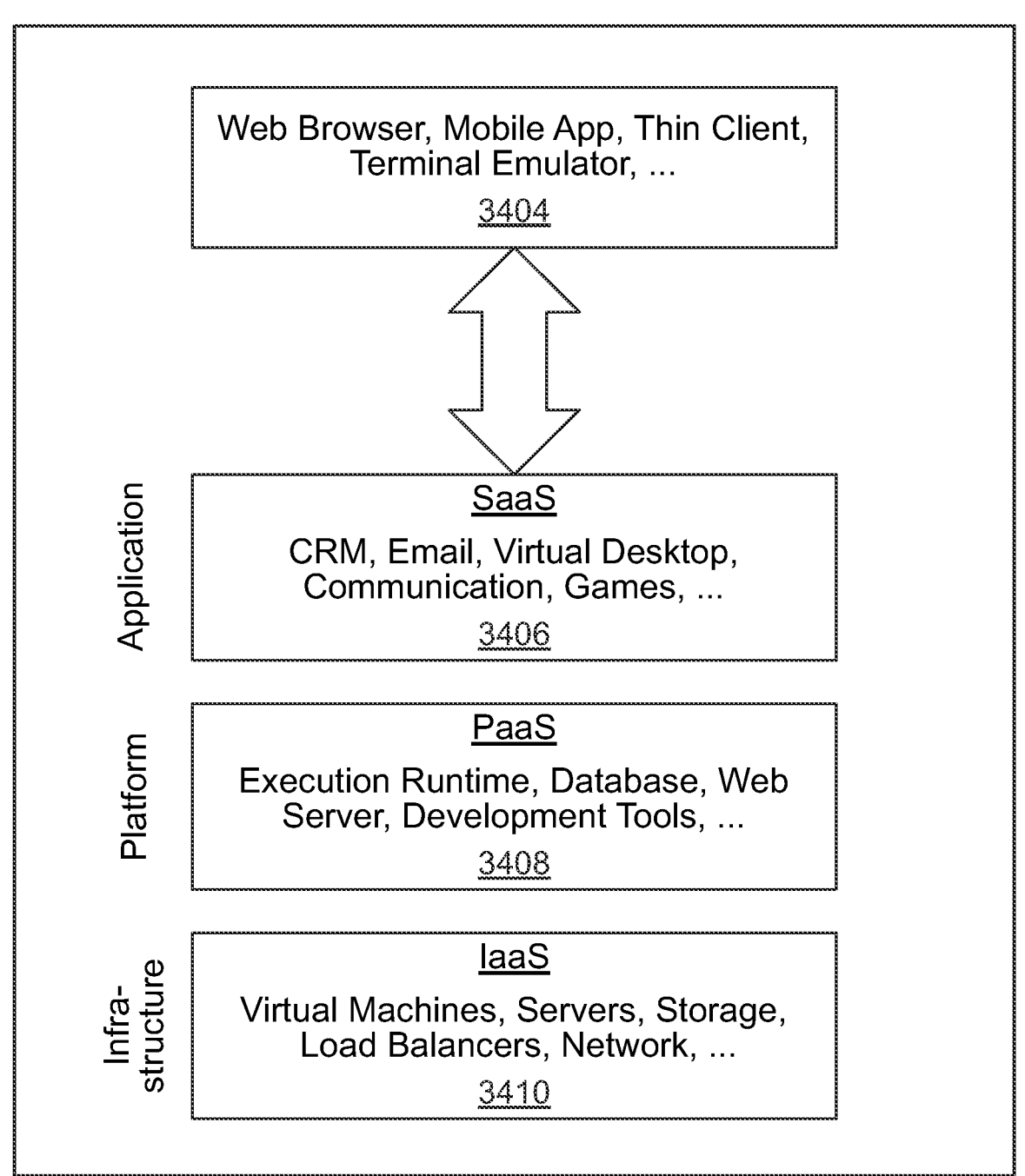
FIG. 34 is a diagrammatic illustration of another high-level connected systems architecture for implementing processes in accordance with aspects of the present disclosure.

In some embodiments, the exemplary inventive computer-based systems/platforms, the exemplary inventive computer-based devices, and/or the exemplary inventive computer-based components of the present disclosure may be specifically configured to operate in a cloud computing/architecture 3225 such as, but not limiting to: infrastructure a service (IaaS) 3410, platform as a service (PaaS) 3408, and/or software as a service (SaaS) 3406 using a web browser, mobile app, thin client, terminal emulator or other endpoint 3404. FIGS. 33 and 34 illustrate schematics of exemplary implementations of the cloud computing/architecture(s) in which the exemplary inventive computer-based systems/platforms, the exemplary inventive computer-based devices, and/or the exemplary inventive computer-based components of the present disclosure may be specifically configured to operate.

Various detailed embodiments of the present disclosure, taken in conjunction with the accompanying FIGs., are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., an analysis of the treatment activities during neuromodulation) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments, exemplary inventive, specially programmed computing systems and platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMAX, CDMA, OFDM, OFDMA, LTE, satellite, ZigBee, and other suitable communication modes.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, PHP, HTML, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, hand-held computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

In some embodiments, as detailed herein, one or more of the computer-based systems of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a message, a map, an entire application (e.g., a calculator), data points, and other suitable data. In some embodiments, as detailed herein, one or more of the computer-based systems of the present disclosure may be implemented across one or more of various computer platforms such as, but not limited to: (1) Linux, (2) Microsoft Windows, (3) OS X (Mac OS), (4) Solaris, (5) UNIX (6) VMWare, (7) Android, (8) Java Platforms, (9) Open Web Platform, (10) Kubernetes or other suitable computer platforms. In some embodiments, illustrative computer-based systems or platforms of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, illustrative computer-based systems or platforms of the present disclosure may be configured to handle numerous concurrent users and/or concurrent neuromodulation systems that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), and so on.

In some embodiments, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application such as Virtual Reality (VR) googles.

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RCS, CAST and Skipjack), cryptographic hash algorithms (e.g., MDS, RIPEMD-160, RTRO, SHA-1, SHA-2, Tiger (TTH), WHIRLPOOL, RNGs).

As used herein, the term "user" shall have a meaning of at least one user. In some embodiments, the terms "user", "subscriber" "consumer" or "customer" should be understood to refer to a user of an application or applications as described herein, and/or a consumer of data supplied by a data provider. By way of example, and not limitation, the terms "user" or "subscriber" can refer to a person who receives data provided by the data or service provider over the Internet in a browser session or can refer to an automated software application which receives the data and stores or processes the data.

The aforementioned examples are, of course, illustrative and not restrictive.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added, and/or any desired steps may be eliminated).

What is claimed is:

1. A system for nerve stimulation, the system comprising:
   a neuromodulation device configured to be worn and adhered to a patient in proximity to a tibial nerve of the patient, the neuromodulation device configured for transcutaneous delivery of electrical stimulation to the tibial nerve for posterior tibial neuromodulation (PTNS) treatment;
   a mobile application executing on a mobile device in communication with the neuromodulation device, the mobile application configured to monitor the transcutaneous delivery of the electrical stimulation by the neuromodulation device and cause the mobile device to display information about the transcutaneous delivery of the electrical stimulation to the tibial nerve and to display assessment tools to receive user feedback to measure and monitor effectiveness of the neuromodulation device and the PTNS treatment as it relates to urinary incontinence; and
   a web service in communication with the mobile application, the web service configured to monitor the neuromodulation device and the mobile application, and configured to transmit, to the mobile application, a treatment protocol to control the neuromodulation device and notifications defining the transcutaneous delivery of the electrical stimulation to the tibial nerve and receive, from the mobile application, the information about the transcutaneous delivery of the electrical stimulation to the tibial nerve,
   wherein the mobile application is configured to verify proper placement of the neuromodulation device on the patient based on one or more measured parameters related to blood flow in the patient to ensure PTNS treatment.

2. The system of claim 1, further comprising a plurality of positioning devices positioned in a treatment area and a tracker device worn by the patient, the web service configured to communicate with the plurality of positioning devices and the tracker device to identify a location of the tracker device for the web service to modify the treatment protocol based on the location of the tracker device.

3. The system of claim 2, wherein the mobile application is further configured to:
   identify, based on communications received from the tracker device or the plurality of positioning devices positioned in the treatment area, the location of the mobile device;
   generate, based on the location of the mobile device or the tracker device, a prompt for input of treatment activities;
   detect selected treatment activities associated with the treatment protocol responsive to the prompt; and
   transmit the location and the selected treatment activities to the web service.

4. The system of claim 1, wherein the neuromodulation device further comprises at least one light-emitting diode (LED) configured to emit light responsive to the transcutaneous delivery of the electrical stimulation to the tibial nerve.

5. The system of claim 1, wherein the neuromodulation device further comprises a buzzer configured to generate audio signals responsive to the transcutaneous delivery of the electrical stimulation to the tibial nerve.

6. The system of claim 1, wherein the neuromodulation device further comprises a voltage controller configured to modulate supply voltage for the transcutaneous delivery of the electrical stimulation to the tibial nerve.

7. The system of claim 1, wherein the neuromodulation device further comprising:
   a first electrode and a second electrode configured for the transcutaneous delivery of the electrical stimulation to the tibial nerve; and
   a strap configured to couple to strap connectors extending from the neuromodulation device to secure the neuromodulation device to the patient.

8. The system of claim 1, wherein the neuromodulation device is further configured to:

store, responsive to termination of communications with the mobile device executing the mobile application, treatment activities to a memory of the neuromodulation device; and transmit, to the mobile device, the treatment activities upon re-establishing communications with the mobile device.

9. The system of claim 1, wherein the mobile application is further configured to:

receive an assigned device identifier of the neuromodulation device of the patient responsive to validating a patient identifier of the patient;

receive a candidate device identifier of the neuromodulation device attempting to establish communications with the mobile application; and establish the communications with the neuromodulation device responsive to matching the assigned device identifier of the neuromodulation device to the candidate device identifier of the neuromodulation device.

10. The system of claim 1, wherein the neuromodulation device further comprises an accelerometer configured to measure mobility and activity of the patient.

11. The system of claim 1, wherein the neuromodulation device further comprises memory configured to store treatment activities about the transcutaneous delivery of the electrical stimulation to the tibial nerve.

12. The system of claim 1, further comprising a sensor device configured to be worn by the patient, the sensor device further configured to:

generate sensor measurements of the one or more measured parameters, the one or more measured parameters comprising oxygen concentration, pulse, electrical frequency, electrical voltage, and accelerometer movements; and transmit the sensor measurements to the mobile application or to the neuromodulation device.

13. The system of claim 12, wherein the mobile application is further configured to:

receive the sensor measurements from the sensor device; and generate a comparison between the sensor measurements and threshold measurements to verify proper placement of the neuromodulation device.

14. The system of claim 1, wherein the mobile application is further configured to:

generate an interface comprising a patient image of an extremity of the patient to which to apply the neuromodulation device;

identify, in the patient image, a treatment site on the extremity to which to apply the neuromodulation device; and generate a virtual image of the neuromodulation device overlayed on the treatment site in the patient image of the extremity for display in the interface to indicate where to position the neuromodulation device.

15. The system of claim 14, wherein the mobile application is further configured to:

communicate with a virtual reality headset; and generate a metaverse of the interface for display by the virtual reality headset.

16. The system of claim 15, wherein the mobile application is further configured to:

receive, from the virtual reality headset, modifications to the treatment protocol.

17. The system of claim 1, wherein the neuromodulation device further comprises feedback electrodes configured to generate electrical measurements for identifying a nerve threshold at which the patient reacts to neuromodulation; and wherein the neuromodulation device is further configured to transmit the electrical measurements to the mobile application.

18. The system of claim 17, wherein the mobile application is further configured to adjust a treatment current based on the electrical measurements received from the feedback electrodes of the neuromodulation device.

19. The system of claim 17, wherein the mobile application is further configured to modify the treatment protocol based on the electrical measurements received from the feedback electrodes of the neuromodulation device.

20. A method for a patient to apply neuromodulation with a neuromodulation device worn by the patient, the method comprising:

establishing, by one or more processors, communications with a mobile device executing a mobile application for managing a treatment protocol applied by the neuromodulation device to the patient;

receiving, by the one or more processors, the treatment protocol to apply to the patient;

verifying, using the mobile application, proper placement of the neuromodulation device on the patient based on one or more measured parameters related to blood flow in the patient; and causing, by the one or more processors, responsive to receiving a signal from the mobile application to begin applying the treatment protocol, the neuromodulation device to begin transcutaneous delivery to apply the neuromodulation to a tibial nerve of the patient for posterior tibial neuromodulation (PTNS) treatment.

21. A method for managing neuromodulation on a mobile application to improve adherence to treatment, the method comprising:

receiving, by one or more processors, from a web service, a treatment protocol to be applied by a neuromodulation device to a tibial nerve of a patient;

detecting, by the one or more processors, a selection to increase a treatment current for applying the treatment protocol; and transmitting, by the one or more processors, treatment parameters included in the treatment protocol and the treatment current to the neuromodulation device.

22. A method for administering neuromodulation by a web service, the method comprising:

generating, by one or more processors, a selectable menu for a healthcare provider to configure treatment parameters defining a treatment protocol to be applied to a patient by a neuromodulation device;

transmitting, by the one or more processors, the selectable menu to a web application for display to the healthcare provider;

receiving, by the one or more processors, the treatment parameters from the web application;

transmitting, by the one or more processors, the treatment parameters to a mobile device executing a mobile application associated with the neuromodulation device, the mobile application causing the neuromodulation device to apply the treatment protocol; and verifying, using the mobile application, proper placement of the neuromodulation device on the patient.

* * * * *